US012737884B2

(12) United States Patent
Sjöstrand et al.

(10) Patent No.: US 12,737,884 B2
(45) Date of Patent: Sep. 15, 2026

(54) SYSTEMS AND METHODS FOR AI-ASSISTED ANALYSIS OF PRIMARY TUMOR IMAGES FOR PREDICTION OF METASTASES

(71) Applicants: Progenics Pharmaceuticals, Inc., N. Billerica, MA (US); EXINI Diagnostics AB, Lund (SE)

(72) Inventors: Karl Vilhelm Sjöstrand, Atlantic Highlands, NJ (US); Kamil Rzechowski, Warsaw (PL)

(73) Assignees: Progenics Pharmaceuticals, Inc., N. Billerica, MA (US); EXINI Diagnostics AB, Lund (SE)

( * ) Notice: Subject to any disclaimer, the term of this patent is extended or adjusted under 35 U.S.C. 154(b) by 242 days.

(21) Appl. No.: 18/667,972

(22) Filed: May 17, 2024

(65) Prior Publication Data

US 2025/0104225 A1 Mar. 27, 2025

Related U.S. Application Data

(60) Provisional application No. 63/606,794, filed on Dec. 6, 2023, provisional application No. 63/540,339, filed on Sep. 25, 2023.

(51) Int. Cl.
*G06T 15/00* (2011.01)
*G06T 7/00* (2017.01)
(Continued)

(52) U.S. Cl.
CPC ............ *G06T 7/0012* (2013.01); *G06T 15/00* (2013.01); *G06V 10/25* (2022.01); *G16H 50/20* (2018.01);
(Continued)

(58) Field of Classification Search
None
See application file for complete search history.

(56) References Cited

U.S. PATENT DOCUMENTS 5,762,608 A 6/1998 Warne et al.
6,944,330 B2 9/2005 Novak et al.
(Continued)

FOREIGN PATENT DOCUMENTS

CN 1200520 A 12/1998
CN 1518719 A 8/2004
(Continued)

OTHER PUBLICATIONS

Ali, A et al., The Automated Bone Scan Index as a Predictor of Response to Prostate Radiotherapy in Men with Newly Diagnosed Metastatic Prostate Cancer: An Exploratory Analysis of STAMPEDE's "M1 |RT Comparison", European Urology Oncology 3:412-419, (2020).

(Continued)

*Primary Examiner* — Idowu O Osifade
(74) *Attorney, Agent, or Firm* — Choate, Hall & Stewart LLP; Ronen Adato

(57) ABSTRACT

Presented herein are systems and methods for the use of automatically-identified suspect regions (e.g., hotspots) within the prostate as imaged in one or more medical images (e.g., PET, CT, or PET/CT image(s)) to predict metastases (e.g., to predict whether localized disease has developed or will develop into metastatic cancer) using a convolutional neural network (CNN).

29 Claims, 22 Drawing Sheets

(51) Int. Cl.
*G06V 10/25* (2022.01)
*G16H 50/20* (2018.01)

(52) U.S. Cl.
CPC ............... *G06T 2207/10081* (2013.01); *G06T 2207/10104* (2013.01); *G06T 2207/30081* (2013.01); *G06T 2207/30096* (2013.01)

(56) References Cited

U.S. PATENT DOCUMENTS 7,450,747 B2 11/2008 Jabri et al.
7,751,605 B2 7/2010 Gündel et al.
7,876,938 B2 1/2011 Huang et al.
7,935,055 B2 5/2011 Burckhardt
7,970,194 B2 6/2011 Kimura
8,199,985 B2 6/2012 Jakobsson et al.
8,211,401 B2 7/2012 Babich et al.
8,467,856 B2 6/2013 Renisch et al.
8,538,166 B2 9/2013 Gordon et al.
8,606,349 B2 12/2013 Rousso et al.
8,705,887 B2 4/2014 Ma et al.
8,778,305 B2 7/2014 Pomper et al.
8,855,387 B2 10/2014 Hamadeh et al.
8,962,799 B2 2/2015 Babich et al.
8,995,736 B2 3/2015 Kaufman et al.
9,002,081 B2 4/2015 Brown
9,028,800 B2 5/2015 D'Souza et al.
9,466,133 B2 10/2016 Sowards-Emmerd et al.
9,710,915 B2 7/2017 Firouzian et al.
9,721,340 B2 8/2017 Gillies et al.
10,058,393 B2 8/2018 Bonutti et al.
10,089,752 B1 10/2018 Bronkalla et al.
10,112,974 B2 10/2018 Neumaier et al.
10,140,544 B1 11/2018 Zhao et al.
10,223,610 B1 3/2019 Akselrod-Ballin et al.
10,311,971 B2 6/2019 Opfer et al.
10,330,763 B2 6/2019 James et al.
10,339,653 B2 7/2019 Gillies et al.
10,340,044 B2 7/2019 Yao et al.
10,340,046 B2 7/2019 Baker
RE47,609 E 9/2019 Hamadeh et al.
10,492,723 B2 12/2019 Madabhushi et al.
10,600,184 B2 3/2020 Golden et al.
10,665,346 B2 5/2020 Baker
10,748,652 B2 8/2020 Yao et al.
10,762,993 B2 9/2020 Baker
10,815,200 B2 10/2020 Cardinale et al.
10,818,386 B2 10/2020 Yao et al.
10,943,681 B2 3/2021 Yao et al.
10,973,486 B2 4/2021 Sjöstrand et al.
11,011,257 B2 5/2021 Lints et al.
11,094,066 B2 8/2021 Nie et al.
11,321,844 B2 5/2022 Johnsson et al.
11,386,988 B2 7/2022 Johnsson et al.
11,424,035 B2 8/2022 Baker
11,508,059 B2 11/2022 Wang et al.
11,534,125 B2 12/2022 Sjöstrand et al.
11,564,621 B2 1/2023 Anand et al.
11,657,508 B2 5/2023 Richter et al.
11,721,428 B2 8/2023 Brynolfsson et al.
11,894,141 B2 2/2024 Baker
11,900,597 B2 2/2024 Anand et al.
11,937,962 B2 3/2024 Sjöstrand et al.
11,941,817 B2 3/2024 Richter et al.
12,224,067 B1 2/2025 Baker
12,243,236 B1 3/2025 Richter et al.
12,243,637 B2 3/2025 Brynolfsson et al.
12,414,748 B2 9/2025 Sjöstrand et al.
12,417,533 B2 9/2025 Anand et al.
2003/0215120 A1 11/2003 Uppaluri et al.
2005/0065421 A1 3/2005 Burckhardt
2005/0281381 A1 12/2005 Guendel
2006/0062425 A1 3/2006 Shen et al.
2006/0064396 A1 3/2006 Wei et al.
2006/0078183 A1 4/2006 deCharms
2007/0081712 A1 4/2007 Huang et al.
2007/0081713 A1 4/2007 Jerebko
2007/0100225 A1 5/2007 Maschke
2007/0115204 A1 5/2007 Budz et al.
2007/0265230 A1 11/2007 Rousso et al.
2008/0027315 A1 1/2008 McGinnis
2008/0214933 A1 9/2008 Von Busch et al.
2009/0213034 A1 8/2009 Wu et al.
2009/0309874 A1 12/2009 Salganicoff et al.
2009/0311182 A1 12/2009 Wang et al.
2010/0032575 A1 2/2010 Lagaru et al.
2010/0080434 A1 4/2010 Seifert et al.
2010/0215581 A1 8/2010 Hoffmann
2010/0266170 A1 10/2010 Khamene et al.
2010/0322488 A1 12/2010 Virtue et al.
2011/0007954 A1 1/2011 Suehling et al.
2011/0063288 A1 3/2011 Valadez
2011/0126159 A1 5/2011 Ko et al.
2011/0255763 A1 10/2011 Bogoni et al.
2012/0123253 A1 5/2012 Renisch et al.
2013/0038707 A1 2/2013 Cunningham et al.
2013/0094704 A1 4/2013 Hamadeh et al.
2013/0129168 A1 5/2013 Ross
2013/0211231 A1 8/2013 Sundarapandian et al.
2013/0281841 A1 10/2013 Everett et al.
2014/0105471 A1 4/2014 Brown
2014/0193336 A1 7/2014 Rousso et al.
2015/0003703 A1 1/2015 Franz et al.
2015/0063667 A1 3/2015 Sprencz et al.
2015/0110716 A1 4/2015 Armor
2015/0119704 A1 4/2015 Roth et al.
2015/0221083 A1 8/2015 Berker
2015/0287188 A1 10/2015 Gazit et al.
2015/0331995 A1 11/2015 Zhao et al.
2015/0356730 A1 12/2015 Grove et al.
2016/0012604 A1 1/2016 Firouzian et al.
2016/0180042 A1 6/2016 Menon et al.
2016/0203263 A1 7/2016 Maier et al.
2016/0275674 A1 9/2016 Rivet-Sabourin et al.
2016/0335395 A1 11/2016 Wu et al.
2016/0350947 A1 12/2016 Kelly
2017/0083682 A1 3/2017 McNutt et al.
2017/0112577 A1 4/2017 Bonutti et al.
2017/0178266 A1 6/2017 Schmidt
2018/0140260 A1 5/2018 Taguchi et al.
2018/0144828 A1 5/2018 Baker
2018/0259608 A1 9/2018 Golden et al.
2018/0360402 A1 12/2018 Carmi
2019/0038239 A1 2/2019 Flohr et al.
2019/0105009 A1 4/2019 Siemionow et al.
2019/0105200 A1 4/2019 Hipsley
2019/0209116 A1 7/2019 Sjostrand et al.
2019/0333623 A1 10/2019 Hibbard
2019/0388049 A1 12/2019 Gupta et al.
2020/0027559 A1 1/2020 Baker
2020/0051238 A1 2/2020 El Harouni et al.
2020/0074634 A1 3/2020 Kecskemethy et al.
2020/0085382 A1 3/2020 Taerum et al.
2020/0090328 A1 3/2020 Takei et al.
2020/0097701 A1 3/2020 Chukka et al.
2020/0126666 A1 4/2020 Baker
2020/0170604 A1 6/2020 Yildirim et al.
2020/0193594 A1 6/2020 Georgescu et al.
2020/0193603 A1 6/2020 Golden et al.
2020/0245960 A1 8/2020 Richter et al.
2020/0311919 A1 10/2020 Grimmer et al.
2020/0315455 A1 10/2020 Lee et al.
2020/0337658 A1 10/2020 Sjostrand et al.
2020/0342600 A1 10/2020 Sjostrand et al.
2020/0352518 A1 11/2020 Lyman et al.
2020/0357117 A1 11/2020 Lyman et al.
2020/0357118 A1 11/2020 Yao et al.
2020/0357521 A1 11/2020 Baker
2020/0410672 A1 12/2020 Katscher et al.
2021/0032206 A1 2/2021 Neumaier et al.
2021/0082547 A1 3/2021 Yao et al.
2021/0093249 A1 4/2021 Anand et al.
2021/0183485 A1 6/2021 Yao et al.
2021/0233633 A1 7/2021 Lints et al.
2021/0334974 A1 10/2021 Johnsson et al.

(56) References Cited

U.S. PATENT DOCUMENTS

| | | | | |
|---|---|---|---|---|
| 2021/0335480 | A1 | 10/2021 | Johnsson et al. | |
| 2022/0005586 | A1 | 1/2022 | Brynolfsson et al. | |
| 2022/0058804 | A1 | 2/2022 | Carmi | |
| 2022/0142480 | A1 | 5/2022 | Peck et al. | |
| 2022/0375612 | A1 | 11/2022 | Baker | |
| 2022/0398724 | A1 | 12/2022 | Anand et al. | |
| 2023/0115732 | A1 | 4/2023 | Brynolfsson et al. | |
| 2023/0148980 | A1 | 5/2023 | Sjöstrand et al. | |
| 2023/0316530 | A1 | 10/2023 | Richter et al. | |
| 2023/0351586 | A1 | 11/2023 | Brynolfsson et al. | |
| 2023/0410985 | A1 | 12/2023 | Brynolfsson et al. | |
| 2023/0420112 | A1 | 12/2023 | Brynolfsson et al. | |
| 2024/0029252 | A1 | 1/2024 | Ichinose et al. | |
| 2024/0127437 | A1 | 4/2024 | Anand et al. | |
| 2024/0169546 | A1 | 5/2024 | Richter et al. | |
| 2024/0186010 | A1 | 6/2024 | Baker | |
| 2024/0285246 | A1 | 8/2024 | Sjöstrand et al. | |
| 2024/0285248 | A1 | 8/2024 | Sjöstrand et al. | |
| 2024/0336965 | A1 * | 10/2024 | Ramani .................... | C12Q 1/44 |
| 2024/0354940 | A1 | 10/2024 | Sjöstrand et al. | |
| 2025/0061580 | A1 | 2/2025 | Richter et al. | |
| 2025/0062029 | A1 | 2/2025 | Baker | |
| 2025/0069232 | A1 | 2/2025 | Richter et al. | |
| 2025/0191752 | A1 | 6/2025 | Sjöstrand et al. | |

FOREIGN PATENT DOCUMENTS

| | | | |
|---|---|---|---|
| CN | 101528267 | A | 9/2009 |
| CN | 101639937 | A | 2/2010 |
| CN | 102096804 | A | 6/2011 |
| CN | 102361594 | A | 2/2012 |
| CN | 102438529 | A | 5/2012 |
| CN | 102947840 | A | 2/2013 |
| CN | 103607954 | A | 2/2014 |
| CN | 103930030 | A | 7/2014 |
| CN | 104463840 | A | 3/2015 |
| CN | 106127819 | A | 11/2016 |
| CN | 106558045 | A | 4/2017 |
| CN | 107563378 | A | 1/2018 |
| CN | 107644421 | A | 1/2018 |
| CN | 114219787 | A | 3/2022 |
| EP | 1426903 | A2 | 6/2004 |
| EP | 1508872 | A1 | 2/2005 |
| EP | 2816525 | A1 | 12/2014 |
| EP | 3043318 | A1 | 7/2016 |
| EP | 3811845 | A1 | 4/2021 |
| GB | 2457577 | A | 8/2009 |
| JP | 2010-029481 | A | 2/2010 |
| JP | 2011-067594 | A | 4/2011 |
| JP | 2012-533384 | A | 12/2012 |
| JP | 2014-006130 | A | 1/2014 |
| JP | 2015-513083 | A | 4/2015 |
| JP | 6013042 | B2 | 10/2016 |
| JP | 2017-500537 | A | 1/2017 |
| JP | 2017-067489 | A | 4/2017 |
| JP | 6170284 | B2 | 7/2017 |
| JP | 2017-198697 | A | 11/2017 |
| JP | 2019-537714 | A | 12/2019 |
| SE | 524500 | C2 | 8/2004 |
| TW | 201201847 | A | 1/2012 |
| TW | 201825049 | A | 7/2018 |
| TW | 201941750 | A | 11/2019 |
| TW | 202006742 | A | 2/2020 |
| WO | WO-99/05503 | A2 | 2/1999 |
| WO | WO-2007/062135 | A2 | 5/2007 |
| WO | WO-2009/084995 | A1 | 7/2009 |
| WO | WO-2010/071999 | A1 | 7/2010 |
| WO | WO-2011/010231 | A1 | 1/2011 |
| WO | WO-2011/077303 | A1 | 6/2011 |
| WO | WO-2011/091378 | A1 | 7/2011 |
| WO | WO-2011/095580 | A1 | 8/2011 |
| WO | WO-2013/059177 | A1 | 4/2013 |
| WO | WO-2013/126147 | A2 | 8/2013 |
| WO | WO-2015/058151 | A2 | 4/2015 |
| WO | WO-2016/087592 | A1 | 6/2016 |
| WO | WO-2018/014475 | A1 | 1/2018 |
| WO | WO-2018/015953 | A1 | 1/2018 |
| WO | WO-2018/081354 | A1 | 5/2018 |
| WO | WO-2019/005722 | A1 | 1/2019 |
| WO | WO-2019/103912 | A2 | 5/2019 |
| WO | WO-2019/136349 | A2 | 7/2019 |
| WO | WO-2020/144134 | A1 | 7/2020 |
| WO | WO-2020/146032 | A1 | 7/2020 |
| WO | WO-2020/190821 | A1 | 9/2020 |
| WO | WO-2020/219619 | A1 | 10/2020 |
| WO | WO-2020/219620 | A1 | 10/2020 |
| WO | WO-2021/061315 | A1 | 4/2021 |
| WO | WO-2022/008374 | A1 | 1/2022 |
| WO | WO-2022/215530 | A1 | 10/2022 |
| WO | WO-2023/057411 | A9 | 7/2023 |
| WO | WO-2023/239829 | A2 | 12/2023 |
| WO | WO-2024/173297 | A1 | 8/2024 |
| WO | WO-2024/211651 | A1 | 10/2024 |
| WO | WO-2025/072177 | A1 | 4/2025 |

OTHER PUBLICATIONS

American College of Radiology (ACR) and the Society for Pediatric Radiology (SPR), ACR-SPR Practice Parameter for the Performance of Skeletal Scintigraphy (Bone Scan), Resolution 28, (2013-Revused2017), available from: <http://www.acr.org>, 9 pages (2017).

Anand, A. et al., A Pre-Analytical Validation Study of Automated Bone Scan Index: Effect on Accuracy and Reproducibility due to the Procedural Variabilities in Bone Scan Image Acquisition. J Nucl Med. pp. 1865-1871, (2016).

Anand, A. et al., Analytic Validation of the Automated Bone Scan Index as an Imaging Biomarker to Standardize Quantitative Changes in Bone Scans of Patients with Metastatic Prostate Cancer, J. Nucl. Med., 57(1):41-45 (2016).

Anand, A. et al., Automated Bone Scan Index as a quantitative imaging biomarker in metastatic castration-resistant prostate cancer patients being treated with enzalutamide, EJNMMI Research, 6:23, 7 pages (2016).

Anand, A. et al., Translating Prostate Cancer Working Group 2 (PCWG2) Progression Criteria into a Quantitative Response Biomarker in Metastatic Castration Resistant Prostate Cancer (mCRPC), ASCO GU Conference, Poster, 1 page, presented Feb. 16, 2017.

Anand, A. et al., Translating Prostate Cancer Working Group 2 (PCWG2) progression criteria into a quantitative response biomarker in metastatic castration-resistant prostate cancer (mCRPC), Journal of Clinical Oncology, 35(6):170 (2017).

Armstrong, A. et al., Assessment of the bone scan index in a randomized placebo-controlled trial of tasquinimod in men with metastatic castration-resistant prostate cancer (mCRPC), Urologic Oncology: Seminars and Original Investigations, 32:1308-1316 (2014).

Armstrong, A. et al., Development and validation of a prognostic model for overall survival in chemotherapy-naive men with metastatic castration-resistant prostate cancer (mCRPC) from the phase 3 prevail clinical trial, Journal of Clinical Oncology, 35(Suppl. 6):Abstract 138, 5 pages, (2017).

Armstrong, A. J. et al., Phase 3 Assessment of the Automated Bone Scan Index as a Prognostic Imaging Biomarker of Overall Survival in Men with Metastatic Castration-Resistant Prostate Cancer: A Secondary Analysis of a Randomized Clinical Trial. JAMA Oncology 4:944-951, (2018).

Armstrong, A. J. et al., Phase 3 prognostic analysis of the automated bone scan index (aBSI) in men with bone-metastatic castration-resistant prostate cancer (CRPC), Meeting Library ASC University, 11 pages (2017).

Bai, P. et al., Body region localization in whole-body low-dose CT images of PET/CT scans using virtual landmarks, Medical Physics Wiley USA, 46(3): 1286-1299 (2019).

Belal, S. et al., Association of PET Index quantifying skeletal uptake in NaF PET/CT images with overall survival in prostate cancer patients, ASCO GU 2017, Poster 178, 1 page, presented Feb. 16, 2017.

(56) References Cited

OTHER PUBLICATIONS

Belal, S. et al., PET Index quantifying skeletal uptake in NaF PET/CT images with overall survival in prostate cancer patients, ASCO GU 2017, Abstract, 1 page, (Feb. 13, 2017).
Belal, S. L. et al., 3D skeletal uptake of 18F sodium fluoride in PET/CT images is associate with overall survival in patients with prostate cancer, EJNMMI Research, 7(15):1-8 (2017).
Belal, S.L. et al., Automated evaluation of normal uptake in different skeletal parts in 18F-sodium fluoride (NaF) PET/CT using a new convolutional neural network method, EJNMMI, EANM '17, 44(Suppl 2):S119-S956, Abstract EP-0116 (2017).
Blue Earth Diagnostics, Posluma Highlights of Prescribing Information, 12 pages, (2023).
Bombardieri, E. et al., Bone scintigraphy: procedure guidelines for tumour imaging, Eur J. Nucl. Med. Mol. Imaging, 30:BP99-BP106, (2003).
Brynolfsson, J., et al., Deep Learning based urinary bladder segmentation using 18FDCFPyL (PyL-PSMA) PET/CT images, EPS-145, European Association of Nuclear Medicine, (2020), <http://link.springer.com/article/10.1007/s00259-020-04988-4>. pp. S1 and S403-404, Retrieved Sep. 18, 2020.
Brynolfsson, J., et al., Deep Learning-Enabled comprehensive detection and quantification of 18FDCFPyL (PyL-PSMA) PET/CT, OP-548, European Association of Nuclear Medicine, (2020), <http://link.springer.com/article/10.1007/s00259-020-04988-4>. pp. S1 and S273, Retrieved Sep. 18, 2020.
Bushberg, J. T. et al., Essential Physics of Medical Imaging, Essential Physics of Medical Imaging, 19.3: p. 581 (table 15-3), p. 713 paragraph 6, section 19.3 and p. 720, (2011).
Capobianco, N. et al., Whole-body uptake classification and prostate cancer staging in 68Ga-PSMA-11 PET/CT using dual-tracer learning, European Journal of Nuclear Medicine and Molecular Imaging, (2021), <https:/doi.org/10.1007/s00259-021-05473-2> 10 pages. Retrieved on Apr. 18, 2021.
Ceci, F. et al., E-PSMA: the EANM standardized reporting guidelines v1.0 for PSMA-PET, European Journal of Nuclear Medicine and Molecular Imaging, 48:1626-1638, (2021).
Cha, K. H., et al. Urinary bladder segmentation in CT urography using deep-learning convolutional neural network and level sets, Medical physics, 43(4):1882-1896, (2016).
Chen, X. et al., TensorMask: A Foundation for Dense Object Segmentation, Proceedings of the IEEE/CVF International Conference on Computer Vision (ICCV), 10 pages, (2019).
Christ, P.F. et al., Automatic Liver and Tumor Segmentation of CT and MRI Volumes Using Cascaded Fully Convolutional Neural Networks, Arxiv.org, Cornell University Library, 20 pages, (2017).
Ciernik, I. F., et al. 3D-segmentation of the 18F-choline PET signal for target volumes definition in radiation therapy of the prostate, Technology in cancer research & treatment 6(1):23-30, (2007).
De Brabandere, B. et al., Semantic Instance Segmentation with a Discriminative Loss Function, arXiv preprint, 10 pages, (2017).
Dennis, E. et al., Bone Scan Index: A Quantitative Treatment Response Biomarker for Castration-Resistant Metastatic Prostate Cancer, Journal of Clinical Oncology, 30(5):519-524 (2012).
Dertat, A., Applied Deep Learning—Part 4: Convolutional Neural Networks, Towards Data Science,<http://towardsdatascience.com/applied-deep-learning-part-4-convolutional-neural-networks-584bc134c1e2> 26 pages, (2017).
Eiber, M. et al., Prostate Cancer Molecular Imaging Standardized Evaluation (PROMISE): Proposed miTNM Classification for the Interpretation of PSMA-Ligand PET/CT, The Journal of Nuclear Medicine, 59(3):469-478, (2018).
Emmett, L. et al., The PRIMARY Score: Using Intraprostatic 68Ga-PSMA PET/CT Patterns to Optimize Prostate Cancer Diagnosis, J. Nucl. Med., 63(11):1644-1650 (2022).
Fendler, W.P. et al., $^{68}$Ga-PSMA PET/CT: Joint EANM and SNMMI procedure guideline for prostate cancer imaging: version 1.0, Eur J Nucl Med Mol Imaging, DOI 10.1007/s00259-017-3670-z, 11 pages, (2017).
Gafita, A. et al., Novel Framework for Treatment Response Evaluation Using PSMA PET/CT in Patients with Metastatic Castration-Resistant Prostate Cancer (RECIP 1.0): An International Multicenter Study, J. Nucl. Med., 63(11):1651-1658 (2022).
GE Healthcare, Spect/CT Cameras, 2 pages, retrieved Oct. 25, 2017: <http://www3.gehealthcare.com.sg/en-GB/products/categories/nuclear_medicine/spect-ct_cameras>.
Ghosh, P. and Mitchell, M., Prostate segmentation on pelvic CT images using a genetic algorithm, Proceedings of SPIE, vol. 6914, Medical Imaging 2008: Image Processing, 8 pages, (2008).
Giesel, F. L. et al., F-18 labelled PSMA-1007: biodistribution, radiation dosimetry and histopathological validation of tumor lesions in prostate cancer patients, Eur. J. Nucl. Med. Mol. Imaging, 44:678-688 (2017).
Gjertsson, K., et al., A Novel Automated Deep Learning Algorithm for Segmentation of the Skeleton in Low-Dose CT for [(18)F] DCFPyL PET/CT Hybrid Imaging in Patients with Metastatic Prostate Cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0823, p. S765.
Gjertsson, K., Segmentation in Skeletal Scintigraphy Images using Convolutional Neural Networks, Master's Theses in Mathematical Sciences, pp. 39-58, (2017), <https://lup.lub.lu.se/student-papers/search/publication/8916406>.
Goffin, K. E. et al., Phase 2 study of $^{99m}$Tc-trofolastat SPECT/CT to identify and localize prostate cancer in intermediate- and high-risk patients undergoing radical prostatectomy and extended pelvic lymph node dissection, J. Nucl. Med., 27 pages (2017).
Gorthi, S. et al., Segmentation of Head and Neck Lymph Node Regions for Radiotherapy Planning Using Active Contour-Based Atlas Registration, IEEE Journal of Selected Topics in Signal Processing, 3(1):135-147 (2009).
Grahovac, M. et al., Machine learning predictive performance evaluation of conventional and fuzzy radiomics in clinical cancer imaging cohorts, Eur. J. Med. Mol. Imaging, 50(6):1607-1620 (2023).
Guan, H. et al., Automatic Hot Spot Detection and Segmentation in Whole Body FDG-PET Images, IEEE International Conference on Image Processing, 4 pages, (2006).
Guimond, A. et al., Average Brain Models: A Convergence Study, Computer Vision and Image Understanding, 77:192-210 (2000).
Hajnal, J. et al., 4.4 Intensity, Size, and Skew Correction; 7.1 Introduction; 7.2 Methods; 7.3 Image Interpretation—General, In: Medical Image Registration, CRC Press LLC, 80-81:144-148 (2001).
Hatamizadeh, A. et al., UNETR: Transformers for 3D Medical Image Segmentation, Proceedings of the IEEE/CVF Winter Conference on Applications of Computer Vision (WACV), 11 pages, (2022).
He, K. et al., Pelvic Organ Segmentation Using Distinctive Curve Guided Fully Convolutional Networks, IEEE Trans. Med. Imaging, 38(2):585-595 (2019).
Hiller, S. M. et al., 99mTc-Labeled Small-Molecule Inhibitors of Prostate-Specific Membrane Antigen for Molecular Imaging of Prostate Cancer, Journal of Nuclear Medicine, 54(8):1369-1376 (2013) retrieved Oct. 25, 2017: <http://jnm.snmjournals.org/content/54/8/1369.full>.
Horikoshi, H. et al., Computer-aided diagnosis system for bone scintigrams from Japanese patients: importance of training database, Annals of Nuclear Medicine, 26(8):622-626 (2012).
Huang, J.-H. et al., A Set of Image Processing Algorithms for Computer-Aided Diagnosis in Nuclear Medicine Whole Body Bone Scan Images, IEEE Transactions on Nuclear Science, 54(3):514-522 (2007).
Iandola, F.N. et al., SqueezeNet: AlexNet-level accuracy with 50x fewer parameters and $<$0.5MB model size, arXiv, 13 pages, (2016).
Im, HJ, et al., et al., Current Methods to Define Metabolic Tumor Volume in Positron Emission Tomography: Which One is Better?, Nucl. Med. Mol. Imaging, 52(1):5-15, (2018).
Inoue, T., What cancers can be understood and not known by "PET"?—Effects of PET scanning by site, Medical Note Interview, 4 pages, (2015), retrieved from the internet at: https://medicalnote.jp/contents/150715-000003-CYJIZE.

(56) References Cited

OTHER PUBLICATIONS

Johnsson, K. et al., Analytical performance of aPROMISE: automated anatomic contextualization, detection, and quantification of [18F]DCFPyL (PSMA) imaging for standardized reporting, European Journal of Nuclear Medicin and Molecular Imaging, 11 pages, Aug. 31, 2021, doi: 10.1007/s00259-021-05497-8. Epub ahead of print. PMID: 34463809.
Johnsson, K., et al., miPSMA Index: Comprehensive and Automated Quantification of 18F-DCFPyL (PyL-PSMA) PET/CT for Prostate Cancer Staging, J Nucl Med., 61: (Supplement 1): 1435, 5 pages, (2020).
Kaboteh R. et al., Progression of bone metastases in patients with prostate cancer—automated detection of new lesions and calculation of bone scan index, EJNMMI Research, 3:64, 6 pages, (2013).
Kaboteh, R. et al., Convolutional neural network based quantification of choline uptake in PET/CT studies is associated with overall survival in patients with prostate cancer, EJNMMI, EANM '17, 44(Suppl 2):S119-S956, Abstract EP-0642 (2017).
Kawakami, K. et al., Introduction of bone scintigraphy diagnosis support software "Bonenavi" (Topics), Journal of Nuclear Medicine (Japanese), 63:41-51 (2011).
Kawakami, K., Evaluation of bone metastasis by bone scintigraphy diagnostic support software Bonenavi, Communication of the Imaging Group of the JSRT, 36(1):74-77 (2013).
Kertesz, H. et al., Implementation of a Spatially-Variant and Tissue-Dependent Positron Range Correction for PET/CT Imaging, Front. Physiol., 13:818463 (2022).
Kertesz, H. et al., Positron range in combination with point-spread-function correction: an evaluation of different implementations for [124I]-PET imaging, ENJMMI Phys., 9(1):56 (2022).
Khurshid, Z. et al., Role of textural heterogeneity parameters in patient selection for 177Lu-PSMA therapy via response prediction, Oncotarget., 9(70):33312-33321 (2018).
Kiess, et al., Prostate-specific membrane antigen and a target for cancer imaging and therapy, The Quarterly Journal of Nuclear Medicine and Molecular Imaging, 59(3):241-268 (2015).
Kikuchi, A. et al., Automated segmentation of the skeleton in whole-body bone scans: influence of difference in atlas, Nuclear Medicine Communications, 33(9):947-953 (2012).
Kinahan, P.E. et al., PET/CT Standardized Update Values (SUVs) in Clinical Practice and Assessing Response to Therapy, Semin Ultrasound CT MR 31(6):496-505 (2010) retrieved Oct. 25, 2017: <https://www.ncbi.nlm.nih.gov/pmc/articles/PMC3026294/>.
Knutsson, H., and Andersson, M., Morphons: Segmentation using Elastic Canvas and Paint on Priors, IEEE International Conference on Image Processing (ICIP 2005), Genova, Italy, 4 pages (2005).
Kopka, K. et al., Glu-Ureido-Based Inhibitors of Prostate-Specific Membrane Antigen: Lessons Learned During the Development of a Novel Class of Low-Molecular-Weight Theranostic Radiotracers, The Journal of Nuclear Medicine, 58(9)(Suppl. 2):17S-26S, (2017).
Krajnc, D. et al., Automated data preparation for in vivo tumor characterization with machine learning, Front. Oncol., 12:1017911 (2022).
Lin, T.Y. et al., Feature Pyramid Networks for object detection, FAIR, 10 pages, (2016), <https://arxiv.org/abs/1612.03144v1>.
Litjens, G. et al., A survey on deep learning in medical image analysis, Medical Image Analysis, 42:60-88, (2017).
Liu, L. et al., Computer-Aided Detection of Prostate Cancer with MRI: Technology and Applications, Acad Radiol. Author manuscript, 50 pages 2016.
Ma, L. et al., Automatic segmentation of the prostate on CT images using deep learning and multi-atlas fusion, Proc. of SPIE vol. 10133:101332O-1-101332O-9 (2017).
Ma, L. et al., Combining Population and Patient-Specific Characteristics for Prostate Segmentation on 3D Ct Images, Proc of SPIE 9784:978427-1-8 (2016).
Ma, L. et al., Random Walk Based Segmentation for the Prostate on 3D Transrectal Ultrasound Images, Proc SPIE Int Soc Opt Eng. Author manuscript, 13 pages (2016).
Matsubara, N. et al., A Phase II, Randomized, Open-Label, Multi-arm Study of TAS-115 for Castration-Resistant Prostate Cancer Patients With Bone Metastases, Clinical Genitourinary Cancer, 000(xxx):1-10, (2021).
Mayo Clinic Staff, Choline C-11 PET scan, Overview, Mayo Clinic, 4 pages (2017), retrieved Oct. 25, 2017: <https://www.mayoclinic.org/tests-procedures/choline-c-11-pet-scan/home/ovc-20156994>.
Meyer, A., et al., Deep learning algorithm improves identification of men with low-risk prostate cancer using PSMA targeted 99mTc-MIP-1404 SPECT/CT, Journal of Clinical Oncology, 37:(15), (2019).
Milletari, F. et al., V-Net: Fully Convolutional Neural Networks for Volumetric Medical Image Segmentation, 2016 Fourth International Conference on 3D Vision (3DV), 11 pages, (2016).
Nakajima, K. et al., Enhanced diagnostic accuracy for quantitative bone scan using an artificial neural network system: a Japanese multi-center database project, EJNMMI Research, 3:83, 9 pages, (2013).
National Cancer Institute, NCI Drug Dictionary: gallium Ga 68-labeled PSMA-11, 1 page, retrieved Oct. 25, 2017: <https://www.cancer.gov/publications/dictionaries/cancer-drug?cdrid=766400>.
National Cancer Institute, NCI Drug Dictionary: technetium Tc 99m methylene diphosphonate, 1 page, retrieved Oct. 25, 2017: <https://www.cancer.gov/publications/dictionaries/cancer-drug?cdrid=537722>.
Nickols, N. et al., aPROMISE: A Novel Automated-PROMISE platform to Standardize Evaluation of Tumor Burden in 18F-DCFPyL (PSMA) images of Veterans with Prostate Cancer, Journal of Nuclear Medicine, 26 pages, May 28, 2021, doi: 10.2967/jnumed.120.261863.
Nickols, N.G., et al., A deep learning algorithm to predict coexisting metastatic disease using intraprostatic [F18]DCFPYL PSMA image alone in veterans with prostate cancer, Journal of Clinical Oncology 38, (Supplement 6), 2020.
Nogi, S. et al., Metastatic bone tumor quantified by computer-assisted diagnosis system of bone scintigraphy, Nuclear Medicine in Clinic, 45(3):35-37 (2012).
Ohlsson, M., et al., Automated decision support for bone scintigraphy, Computer-based medical systems, pp. 1-6, (2009).
Papp, L. et al., Glioma Survival Prediction with Combined Analysis of In Vivo 11C-MET PET Features, Ex Vivo Features, and Patient Features by Supervised Machine Learning, J. Nucl. Med., 59(6):892-899 (2018).
Papp, L. et al., Optimized Feature Extraction for Radiomics Analysis of 18F-FDG PET Imaging, J. Nucl. Med., 60(6):864-872 (2019).
Papp, L. et al., Supervised machine learning enables non-invasive lesion characterization in primary prostate cancer with [68Ga]Ga-PSMA-11 PET/MRI, Eur. J. Nucl. Mol. Imaging, 48(6):1795-1805 (2021).
Partin, A.W. et al., Combination of prostate-specific antigen, clinical stage, and Gleason score to predict pathological stage of localized prostate cancer. A multi-institutional update, JAMA, 277(18):1445-1451 (1997).
Partin, A.W. et al., The use of prostate specific antigen, clinical stage and Gleason score to predict pathological stage in men with localized prostate cancer, J. Urol., 150(1):110-114 (1993).
Paschalis, A. et al., Prostate-specific Membrane Antigen Heterogeneity and DNA Repair Defects in Prostate Cancer, European Urology, 76(4):469-478, (2019).
Perera, M. et al., Sensitivity, Specificity, and Predictors of Positive 68Ga-Prostate-specific Membrane Antigen Positron Emission Tomography in Advanced Prostate Cancer: A Systematic Review and Meta-analysis, European Urology, 70(6):926-937 (2016).
Polymeri, E. et al., Analytical validation of an automated method for segmentation of the prostate gland in CT images, EJNMMI, EANM '17, 44(Suppl 2):S119-S956, Abstract EP-0641 (2017).
Polymeri, E., et al., Deep learning-based quantification of PET/CT prostate gland uptake: association with overall survival, Clinical Physiology Functional Imaging, DOI: 10.1111/cpf.12611, 40(2):106-113, (2019).
Poulakis, V. et al., Preoperative neural network using combined magnetic resonance imaging variables, prostate specific antigen, and Gleason score to predict prostate cancer recurrence after radical prostatectomy, Eur. Urol., 46(5):571-578 (2004).

(56) References Cited

OTHER PUBLICATIONS

Pouliot, F., et al., Prospective evaluation of a Novel Deep Learning Algorithm (PSMA-AI) in the assessment of 99mTc-MIP-1404 SPECT/CT in patients with low or intermediate risk prostate cancer, Annual Congress of the European Association of Nuclear Medicine Oct. 12-16, 2019 Barcelona, Spain. Eur J Nucl Med Mol Imaging 46 (Suppl 1), S1-S952 (2019). Abstract EP-0804, p. S765.

radiologyinfo.org for Patients, Computed Tomography (CT), 2 pages, retrieved Oct. 25, 2017: <https://www.radiologyinfo.org/en/submenu.cfm?pg=ctscan>.

Ren, S., et al., Faster R-CNN: Towards Real-Time Object Detection with Region Proposal Networks, 14 pages, (2015), <http://image-net.org/challenges/LSVRC/2015/results>.

Ronneberger, O., et al., U-Net: Convolutional Networks for Biomedical Image Segmentation, Springer International Publishing, pp. 234-241, (2015), <http://lmb.informatik.uni-freiburg.de/>. Published online on Nov. 18, 2015.

Rowe, S. P. et al., PET Imaging of prostate-specific membrane antigen in prostate cancer: current state of the art and future challenges, Prostate Cancer and Prostatic Diseases, pp. 1-8 (2016).

Rowe, S. P. et al., PSMA-Based [$^{18}$F]DCFPyL PET/CT is Superior to Conventional Imaging for Lesion Detection in Patients with Metastatic Prostate Cancer, Mol Imaging Biol, 18:411-419, (2016).

Sabbatini, P. et al., Prognostic Significance of Extent of Disease in Bone in Patients With Androgen-Independent Prostate Cancer, Journal of Clinical Oncology, 17(3):948-957 (1999).

Sadik, M. et al., 3D prostate gland uptake of 18F-choline-association with overall survival in patients with hormone-naïve prostate cancer, The Journal of Nuclear Medicine, 58(Suppl. 1):Abstract 544, 2 pages, (2017).

Sadik, M. et al., A new computer-based decision-support system for the interpretation of bone scans, Nuclear Medicine Communications, 27(5):417-423 (2006).

Sadik, M. et al., Automated 3D segmentation of the prostate gland in CT images—a first step towards objective measurements of prostate uptake in PET and SPECT images, Journal of Nuclear Medicine, 58(1):1074, (2017).

Sadik, M. et al., Automated quantification of reference levels in liver and mediastinum (blood pool) for the Deauville therapy response classification using FDG-PET/CT in lymphoma patients, EJNMMI, EANM '17, 44(Suppl 2):S119-S956, Abstract EP-0770 (2017).

Sadik, M. et al., Computer-assisted interpretation of planar whole-body bone scans, Journal Nuclear Medicine, 49(12):1958-65, 2008.

Sadik, M. et al., Convolutional neural networks for segmentation of 49 selected bones in CT images show high reproducibility, EJNMMI, EANM '17, 44(Suppl 2):S119-S956, Abstract OP-657 (2017).

Sadik, M. et al., Improved classifications of planar whole-body bone scans using a computer-assisted diagnosis system: a multicenter, multiple-reader, multiple-case study, Journal of Nuclear Medicine, 50(3): 368-75, 2009.

Sadik, M. et al., Variability in reference levels for Deauville classifications applied to lymphoma patients examined with 18F-FDG-PET/CT, EJNMMI, EANM '17, 44(Suppl 2):S119-S956, Abstract EP-0771 (2017).

Sajn, L. et al., Computerized segmentation of whole-body bone scintigrams and its use in automated diagnostics, Computer Methods and Programs in Biomedicine, 80:47-55 (2005).

Salerno, J. et al., Multiparametric magnetic resonance imaging for pre-treatment local staging of prostate cancer: A Cancer Care Ontario clinical practice guideline, Canadian Urological Association Journal, 10(9-10):332-339 (2016).

Santos-Cuevas, C. et al. 99mTc-labeled PSMA inhibitor: Biokinetics and radiation dosimetry in healthy subjects and imaging of prostate cancer tumors in patients, Nuclear Medicine and Biology 52:1-6, (2017).

Seifert, R. et al., Second Version of the Prostate Cancer Molecular Imaging Standardized Evaluation Framework Including Response Evaluation for Clinical Trials (Promise V2), Eur. Urol., 83(5):405-412 (2023).

Shi, F. et al., Deep learning empowered vol. delineation of whole-body organs-at-risk for accelerated radiotherapy, Nat. Commun., 13(1):6566 (2022).

Sjöstrand K. et al., Statistical regularization of deformation fields for atlas-based segmentation of bone scintigraphy images, MICCAI 5761:664-671 (2009).

Sjöstrand, K., et al., Automated detection and quantification of Prostatic PSMA uptake in SPECT/CT using a Deep Learning Algorithm for Segmentation of Pelvic Anatomy, The Journal of Nuclear Medicine, 59(1):p. 30, (2018).

Sjostrand, K., et al., Automated Assessment of Prostatic PSMA Expression in SPECT/CT using Deep Convolutional Neural Networks—A Prospectively Planned Retrospective Analysis of Phase 3 Study MIP-1404-3301, The Journal of Nuclear Medicine, 60 (Supplement 1): Abstract 401, 1 page, (2019).

Sluimer, I. et al., Toward Automated Segmentation of the Pathological Lung in CT, IEEE Transactions on Medical Imaging, 24(8):1025-1038 (2005).

Teng, C. et al., Head and neck lymph node region delineation using a hybrid image registration method, 3rd IEEE International Symposium on Biomedical Imaging: Nano to Macro, 4 pages, (2006).

Tian, Z. et al., A fully automatic multi-atlas based segmentation method for prostate MR images, Proc SPIE Int Soc Opt Eng. Author manuscript, 12 pages (2015).

Tian, Z. et al., A supervoxel-based segmentation method for prostate MR images, Med. Phys., 44(2):558-569 (2017).

Tian, Z. et al., Deep convolutional neural network for prostate MR segmentation, Proc. of SPIE 10135:101351L-1-101351L-6 12 pages, (2017).

Tian, Z., et al., Superpixel-based Segmentation for 3D Prostate MR Images, IEEE Trans Med Imaging, Author manuscript, pp. 558-569, (2016).

Trägårdh, E., et al., RECOMIA—a cloud-based platform for artificial intelligence research in nuclear medicine and radiology, EJNMMI Physics, <https://doi.org/10.1186/s40658-020-00316-9>, 7:51, 12 pages, (2020).

Ulmert, D. et al., A Novel Automated Platform for Quantifying the Extent of Skeletal Tumour Involvement in Prostate Cancer Patients Using the Bone Scan Index, European Urology, 62(1):78-84 (2012).

US Food and Drug Administration, Clinical Trial Endpoints for the Approval of Cancer Drugs and Biologics, 21 pages, (2018).

Valladares, A. et al., A multi-modality physical phantom for mimicking tumor heterogeneity patterns in PET/CT and PET/MRI, Med. Phys., 49(9):5819-5829 (2022).

Wallis, J.W. et al., Three-dimensional display in nuclear medicine, IEEE Trans Med Imaging, 8(4):297-303, (1989).

Washino, H., Injectable for bone scintigraphy: Technetium hydroxymethylenediphosphonate (99mTc) injection solution (Revised Edition), 9 pages, (2007), retrieved from the internet at:https://rada.or.jp/database/home4/normal/ht-docs/member/synopsis/030292.html#:%7E:text=%E6%A6%82%E8%A6%81).

Wrangsjo, A. et al., Non-rigid Registration Using Morphons, Proceedings of the 14th Scandinavian Conference on Image Analysis (SCIA '05), pp. 501-510 (2005).

Yin, T.-K., and Chiu, N.T., A Computer-Aided Diagnosis for Locating Abnormalities in Bone Scintigraphy by a Fuzzy System With a Three-Step Minimization Approach, IEEE Transactions on Medical Imaging, 23(5):639-654 (2004).

Benitez, C.M. et al., Treatment Response Assessment According to Updated PROMISE Criteria in Patients with Metastatic Prostate Cancer Using an Automated Imaging Platform for Identification, Measurement, and Temporal Tracking of Disease, European Urology Oncology, 9 pages, (2024).

Wan, H., Automated Contouring Using Neural Networks, Contour Protege Al White Paper, 3 pages, (2020), <https://go.mimsoftware.com/contour-protegeai-plus/white-paper>.

Afshar-Oromieh, A. et al., Radiation dosimetry of (68)Ga-PSMA-11 (HBED-CC) and preliminary evaluation of optimal imaging timing, Eur. J. Nucl. Med. Mol. Imaging, 43(9):1611-1620 (2016).

Gandaglia, G. et al., Distribution of metastatic sites in patients with prostate cancer: A population-based analysis, Prostate, 74(2):210-216 (2014).

(56) References Cited

OTHER PUBLICATIONS

Giesel, F.L. et al., (18)F-Labelled PSMA-1007 shows similarity in structure, biodistribution and tumour uptake to the theragnostic compound PSMA-617, Eur. J. Nucl. Med. Mol. Imaging, 43(10):1929-1930 (2016).
Greenspan, H. et al., Deep Learning in Medical Imaging: Overview and Future Promise of an Exciting New Technique, IEEE Transactions on Medical Imaging, 35(5):1153-1159 (2016).
Guntur, A.R. and Rosen, C.J., Bone as an endocrine organ, Endocr. Pract., 18(5):758-762 (2012).
International Search Report for PCT/US2024/0148177, 6 pages, Feb. 6, 2025.
Kaur, D. and Kaur, Y., Various Image Segmentation Techniques: A Review, International Journal of Computer Science and Mobile Computing, 3(5):809-814 (2014).
Pizzuto, D.A. et al., The central zone has increased 68Ga-PSMA-11 uptake: "Mickey Mouse ears" can be hot on 68Ga-PSMA-11 PET, Eur. J. Nucl. Med. Mol. Imaging, 45(8):1335-1343 (2018).
Seifert, S. et al., Hierarchical parsing and semantic navigation of full body CT data, Medical Imaging 2009: Image Processing, Proceedings of SPIE vol. 7259, 8 pages, (2009).
Sharma, N. and Aggarwal, L.M., Automated medical image segmentation techniques, J. Med. Phys., 35(1):3-14 (2010).
Shen, D. et al., Deep Learning in Medical Image Analysis, Annu. Rev. Biomed. Eng., 19:221-248 (2017).
Weineisen, M. et al., 68Ga- and 177Lu-Labeled Psma I&T: Optimization of a PSMA-Targeted Theranostic Concept and First Proof-of-Concept Human Studies, J. Nucl. Med., 56(8):1169-1176 (2015).
Written Opinion for PCT/US2024/0148177, 12 pages, Feb. 6, 2025.
Petition for Inter Partes Review of U.S. Pat. No. 10,665,346, *MIM Software Inc.* v. *Progenics Pharmaceuticals, Inc.*, Inter Partes Review No. IPR2025-00630, Feb. 21, 2025.
Petition for Inter Partes Review of U.S. Pat. No. 11,424,035, *MIM Software Inc.* v. *Progenics Pharmaceuticals, Inc.*, Inter Partes Review No. IPR2025-00725, Mar. 14, 2025.
Petition for Inter Partes Review of U.S. Pat. No. 11,894,141, *MIM Software Inc.* v. *Progenics Pharmaceuticals, Inc.*, Inter Partes Review No. IPR2025-00726, Mar. 14, 2025.
Petition for Inter Partes Review of U.S. Pat. No. 11,941,817, *MIM Software Inc.* v. *EXINI Diagnostics AB.*, Inter Partes Review No. IPR2025-00827, Apr. 4, 2025.
Kumar, A. et al., Designing user interfaces to enhance human interpretation of medical content-based image retrieval: application to PET-CT images, Int. J. Comput. Assist. Radiol. Surg., 8(6):1003-1014 (2013).
Mata, C. et al., ProstateAnalyzer: GUI in Medical Domain with Management of DICOM Images of Prostate Cancer (PCa), 1 page, (2012).
Roman-Jimenez, G. et al., Detection of bladder metabolic artifacts in (18)F-FDG PET imaging, Comput. Biol. Med., 71:77-85 (2016).
Saha, M. et al., An Advanced Deep Learning Approach for Ki-67 Stained Hotspot Detection and Proliferation Rate Scoring for Prognostic Evaluation of Breast Cancer, Sci. Rep., 7(1):3213 (2017).
Nitta, S. et al., Assisted Diagnosis System by Automatic Extraction of Tumor Candidate Areas from PET/CT Images, Medical Imaging Technology, 24(3):181-190 (2006). English translation included.

* cited by examiner

SYSTEMS AND METHODS FOR AI-ASSISTED ANALYSIS OF PRIMARY TUMOR IMAGES FOR PREDICTION OF METASTASES

CROSS-REFERENCE TO RELATED APPLICATIONS

This application claims priority to and benefit from U.S. Provisional Application 63/606,794, filed Dec. 6, 2023 and U.S. Provisional Application No. 63/540,339, filed Sep. 25, 2023, the content of each of which is incorporated by reference herein in their entirety. This application is related to U.S. Provisional Application No. 63/350,211, filed Jun. 8, 2022, U.S. Provisional Application No. 63/458,031, filed on Apr. 7, 2023, U.S. Provisional Application No. 63/461,486, filed on Apr. 24, 2023, and U.S. patent application Ser. No. 18/207,246, filed on Jun. 8, 2023, the contents of each of which are hereby incorporated by reference in their entirety. This application is also related to U.S. patent application Ser. No. 16/734,609, filed Jan. 6, 2020, and U.S. patent application Ser. No. 17/762,796, filed Mar. 23, 2022, the contents of each which are hereby incorporated by reference in their entirety.

FIELD

This invention relates generally to systems and methods for creation, analysis, and/or presentation of medical image data. More particularly, in certain embodiments, the invention relates to systems and methods for automated analysis of medical images to identify and/or characterize cancerous lesions and/or prognosis or risk for a subject.

SUMMARY

Presented herein are systems and methods for predicting presence and/or risk of metastases in a subject, based on medical image data that reflects presence of localized disease. In particular, among other things, metastatic disease prediction technologies of the present disclosure leverage artificial neural networks (ANNs) to analyze image data that is associated with and reflects presence of localized disease, such as images of regions about a single primary tumor and/or one or more lesions confined to a single tissue region or organ, where cancer was first detected. Among other things, technologies described herein make use of the insight that, while such images of localized disease may not include conventional or express hallmarks of metastatic disease, such as presence of hotspots dispersed outside the primary organ and/or tumor, they nonetheless may reflect patterns, features, such as particular intensity patterns and/or hotspot features, etc. that are indicative of (e.g., correlate with) presence and/or risk of metastases. While such patterns and their relationship/implications for whether a particular subject has or will develop metastatic disease may escape conventional image analysis methods and/or review by human professionals, such as physicians, radiologists, and the like, ANN technologies of the present disclosure can be trained and used to generate predictions of whether a subject has or will develop metastases—i.e., one or more cancerous lesions outside of a primary tumor and/or site (e.g., organ or tissue region) where cancer was originally detected.

In one aspect, the invention is directed to a method for automatically processing one or more medical images (e.g., 3D images) of a subject and using the processed image(s) to automatically predict a presence and/or a risk of metastases (e.g., to automatically predict whether localized disease has developed or will develop into metastatic cancer), the method comprising: (a) receiving, by a processor of a computing device, one or more medical images of a prostate of the subject {e.g., a PET/CT image obtained with a PSMA targeted imaging agent, e.g., [F18]DCFPyL (PyL)}; (b) automatically identifying, by the processor, a prostate volume of the image(s) corresponding to the prostate of the subject (e.g., segmenting the prostate); (c) automatically identifying, by the processor, one or more suspect regions (e.g., hotspots) within the prostate volume; and (d) predicting, by the processor, using a neural network (e.g., a convolutional neural network) (e.g., wherein both the automatically identified prostate volume and the automatically identified hotspots are used as inputs of the neural network), (i) a presence of metastases in the subject (e.g., predicting whether localized disease has developed into metastatic cancer), and/or (ii) a risk of metastases in the subject (e.g., predicting whether localized disease will develop into metastatic cancer), said predicting based at least in part on the automatically identified prostate and the automatically identified one or more suspect regions.

In certain embodiments, the one or more medical images comprise a 3D anatomical image (e.g., a CT image) and a 3D functional image (e.g., a PET image).

In certain embodiments, the one or more medical images comprise a PET image and/or a PET/CT image [e.g., obtained following administration to a subject of an imaging agent comprising PSMA binding agent (e.g., PyL)].

In certain embodiments, the one or more medical images are obtained within six (6) months or less (e.g., three months or less) from an initial diagnosis and/or pathological assessment.

In certain embodiments, the one or more medical images are obtained prior to treatment.

In certain embodiments, the one or more medical images are localized around the prostate volume [e.g., comprising a pelvic region (e.g., having been acquired at a single bed position); e.g., and wherein the one or more medical images are or comprise one or more SPECT and/or SPECT/CT images (e.g., having been obtained following administration to the subject of a PSMA binding agent)].

In certain embodiments, the one or more medical images comprise a 3D functional image, and wherein step (b) comprises identifying the prostate volume within the 3D functional image.

In certain embodiments, the one or more medical images comprise a 3D anatomical image co-aligned with the 3D functional image, and wherein step (b) comprises identifying an anatomical volume of interest (VOI) representing a prostate within the 3D anatomical image and using the anatomical VOI to identify the prostate volume within the functional image.

In certain embodiments, the method comprises using a first machine learning model (e.g., an anatomical segmentation model) to (i) identify the prostate volume within the 3D functional image and/or (ii) identify the anatomical VOI within the 3D anatomical image.

In certain embodiments, the one or more medical images comprise a 3D functional image and wherein step (c) comprises automatically identifying (e.g., as the one or more suspect regions) one or more hotspots within the 3D functional image.

In certain embodiments, the method comprises using a second machine learning model to automatically identify the one or more hotspots.

In certain embodiments, the neural network receives at least two channels of input, the at least two channels of input comprising: (A) a prostate intensity channel comprising intensities of voxels located within the prostate volume of the image(s) corresponding to the prostate [e.g., a cuboid image region comprising a segmented prostate volume (e.g., and a small buffer about the segmented prostate, e.g., approximately 1, 5, 10, 25 voxels; e.g., approximately 1 mm, 2 mm, 5 mm, 10 mm)]; and (B) a hotspot mask channel comprising a mask identifying the one or more suspect region(s) [e.g., the hotspot mask channel comprising a hotspot mask/map cropped (e.g., intersected with) a cuboid region of a same size as the prostate intensity channel].

In certain embodiments, the neural network does not receive, as input, intensities of voxels located outside the prostate volume of the image(s) [e.g., outside a cuboid image region comprising a segmented prostate volume (e.g., and a small buffer about the segmented prostate, e.g., approximately 1, 5, 10, 25 voxels; e.g., approximately 1 mm, 2 mm, 5 mm, 10 mm)].

In certain embodiments, the neural network generates, as output, a likelihood value representing a likelihood (e.g., as determined by the neural network) that a subject has or will develop metastases [e.g., a risk that the subject has synchronous metastases, and/or a risk that the subject will develop metachronous metastases (e.g., six months or more following a time at which the one or more medical images were obtained; e.g., following curative intent therapy (e.g., surgery, chemotherapy, radiation, or combinations thereof))].

In certain embodiments, step (d) comprises using one or more measured features (e.g., PSA score, pathologic grade, percent positive cores, uptake peak value) (e.g., as input, alongside neural network output, to a classifier) to predict presence and/or risk of metastases in the subject.

In certain embodiments, step (d) comprises using one or more computed features (e.g., a PRIMARY score, and/or a PSMA expression score) (e.g., as input, alongside neural network output, to a classifier) to predict presence and/or risk of metastases in the subject In certain embodiments, the one or more medical images are or comprise one or more 3D functional images acquired following administration to a subject of an imaging agent.

In certain embodiments, the imaging agent is or comprises a PSMA binding agent (e.g., PyL; e.g., PSMA-11).

In certain embodiments, the medical images do not include any graphical representation(s) of metastases outside the prostate volume [e.g., no representations of suspect regions (e.g., graphical representations of potential lesions (e.g., hotspots)) outside of the prostate volume].

In certain embodiments, the method comprises, at step (d), predicting a risk of metastases (e.g., a risk that the subject will develop metachronous metastases).

In certain embodiments, the method comprises, at step (d), predicting a presence of metastases (e.g., predicting a presence of synchronous metastases).

In certain embodiments, the neural network is a trained neural network, having been trained [e.g., to generate, as output, a metastases score representing the prediction of (i) the presence of metastases (e.g., the presence of synchronous metastases) in the subject and/or (ii) the risk of metastases (e.g., the risk of metachronous metastases)] using a plurality of example images each obtained from a particular subject and comprising a graphical representation of suspect regions within a prostate region of the particular subject, said plurality of example images comprising: (A) a plurality of positive example images obtained for subjects known to have (e.g., synchronous) metastases; and (B) a plurality of negative example images obtained for subjects having localized disease (e.g., without metastases).

In certain embodiments, the plurality of positive example images are images obtained for subjects having synchronous metastases and wherein step (d) comprises using the neural network to predict the risk of metastases (e.g., metachronous metastases) for the subject.

In certain embodiments, the subject is or has been determined to have localized prostate cancer, with observable lesions {e.g., as determined via pathological assessment; e.g., as determined based on analysis of the one or more medical images [e.g., and identification of one or more suspect regions meeting one or more criteria (e.g., having a minimum size, intensity, etc.)}confined to a primary tumor volume comprising and/or about the prostate of the subject [e.g., comprising the prostate and a surrounding buffer/margin (e.g., approximately 1, 5, 10, 25 voxels; e.g., approximately 1 mm, 2 mm, 5 mm, 10 mm)] and wherein step (d) comprises predicting, as the risk of metastases, a likelihood that the subject will develop one or more observable lesions outside the primary tumor volume (e.g., outside the prostate and/or its surrounding buffer/margin) (e.g., thereby generating a quantitative prediction of risk that the localized disease will develop into metastatic disease).

In certain embodiments, step (c) comprises automatically identifying the one or more suspect regions within the prostate volume (e.g., and/or the surrounding buffer/margin), but not identifying any suspect regions outside of the prostate volume and/or a surrounding buffer/margin.

In certain embodiments, no suspect region(s) are identified outside of the prostate volume (e.g., and/or a surrounding buffer/margin thereof).

In certain embodiments, step (d) comprises generating, by the neural network, (e.g., as the likelihood that the subject will develop one or more observable lesions outside the primary tumor volume) a likelihood value representing a risk that lesions will spread outside the primary tumor region (e.g., outside the prostate), within a particular period of time [e.g., within 6 months (synchronous metastasis) or e.g., after greater than 6 months (metachronous metastasis)].

In another aspect, the invention is directed to a system for automatically processing one or more medical images (e.g., 3D images) of a subject and using the processed image(s) to automatically predict a presence and/or a risk of metastases (e.g., to automatically predict whether localized disease has developed or will develop into metastatic cancer), the system comprising: a processor of a computing device; and memory having instructions stored thereon, wherein the instructions, when executed by the processor, cause the processor to: (a) automatically identify a prostate volume of one or more medical image(s) {e.g., a PET/CT image obtained with a PSMA targeted imaging agent, e.g., [F18] DCFPyL (PyL)}, said automatically identified prostate volume corresponding to a prostate of a subject (e.g., segmenting the prostate); (b) automatically identify one or more suspect regions (e.g., hotspots) within the prostate; and (c) predict, using a neural network (e.g., a convolutional neural network) (e.g., wherein both the automatically identified prostate volume and the automatically identified hotspots are used as inputs of the neural network), (i) a presence of metastases in the subject (e.g., predicting whether localized disease has developed into metastatic cancer), and/or (ii) a risk of metastases in the subject (e.g., predicting whether localized disease will develop into metastatic cancer), said predicting based at least in part on the automatically identified prostate volume and the automatically identified one or more suspect regions.

In certain embodiments, the one or more medical images comprise a 3D anatomical image (e.g., a CT image) and a 3D functional image (e.g., a PET image).

In certain embodiments, the one or more medical images comprise a PET image and/or a PET/CT image [e.g., obtained following administration to a subject of an imaging agent comprising PSMA binding agent (e.g., PyL)].

In certain embodiments, the one or more medical images are obtained within six (6) months or less (e.g., three months or less) from an initial diagnosis and/or pathological assessment.

In certain embodiments, the one or more medical images are obtained prior to treatment.

In certain embodiments, the one or more medical images are localized around the prostate volume [e.g., comprising a pelvic region (e.g., having been acquired at a single bed position); e.g., and wherein the one or more medical images are or comprise one or more SPECT and/or SPECT/CT images (e.g., having been obtained following administration to the subject of a PSMA binding agent)].

In certain embodiments, the one or more medical images comprise a 3D functional image, and wherein, at step (a), the instructions cause the processor to identify a prostate volume within the 3D functional image.

In certain embodiments, the one or more medical images comprise a 3D anatomical image co-aligned with the 3D functional image, and wherein, at step (a), the instructions cause the processor to identify an anatomical volume of interest (VOI) representing a prostate within the 3D anatomical image and use the anatomical VOI to identify the prostate volume within the functional image.

In certain embodiments, the instructions cause the processor to use a first machine learning model (e.g., an anatomical segmentation model) to (i) identify the prostate volume within the 3D functional image and/or (ii) identify the anatomical VOI within the 3D anatomical image.

In certain embodiments, the one or more medical images comprise a 3D functional image and wherein, at step (b), the instructions cause the processor to automatically identify (e.g., as the one or more suspect regions) one or more hotspots within the 3D functional image.

In certain embodiments, the instructions cause the processor to use a second machine learning model to automatically identify the one or more hotspots.

In certain embodiments, the neural network receives at least two channels of input, the at least two channels of input comprising: (A) a prostate intensity channel comprising intensities of voxels located within the prostate volume of the image(s) [e.g., a cuboid image region comprising a segmented prostate volume (e.g., and a small buffer about the segmented prostate, e.g., approximately 1, 5, 10, 25 voxels; e.g., approximately 1 mm, 2 mm, 5 mm, 10 mm)]; and (B) a hotspot mask channel comprising a mask identifying the one or more suspect region(s) [e.g., the hotspot mask channel comprising a hotspot mask/map cropped (e.g., intersected with) a cuboid region of a same size as the prostate intensity channel].

In certain embodiments, the neural network does not receive, as input, intensities of voxels located outside the volume of the image(s) corresponding to the prostate [e.g., outside a cuboid image region comprising a segmented prostate volume (e.g., and a small buffer about the segmented prostate, e.g., approximately 1, 5, 10, 25 voxels; e.g., approximately 1 mm, 2 mm, 5 mm, 10 mm)].

In certain embodiments, the neural network generates, as output, a likelihood value representing a likelihood (e.g., as determined by the neural network) that a subject has or will develop metastases (e.g., a risk that the subject has synchronous metastases, and/or a risk that the subject will develop metachronous metastases).

In certain embodiments, at step (c), the instructions cause the processor to use one or more measured features (e.g., PSA score, pathologic grade, percent positive cores, uptake peak value) (e.g., as input, alongside neural network output, to a classifier) to predict presence and/or risk of metastases in the subject.

In certain embodiments, at step (c), the instructions cause the processor to use one or more computed features (e.g., a PRIMARY score, and/or a PSMA expression score) (e.g., as input, alongside neural network output, to a classifier) to predict presence and/or risk of metastases in the subject.

In certain embodiments, the one or more medical images are or comprise one or more 3D functional images acquired following administration to a subject of an imaging agent.

In certain embodiments, the imaging agent is or comprises a PSMA binding agent (e.g., PyL; e.g., PSMA-11).

In certain embodiments, the medical images do not include any graphical representation of metastases [e.g., no representations of suspect regions (e.g., graphical representations of potential lesions (e.g., hotspots)) outside of the prostate volume].

In certain embodiments, the instructions cause the processor to, at step (c), predict a risk of metastases (e.g., a risk that the subject will develop metachronous metastases).

In certain embodiments, the instructions cause the processor to, at step (c), predicting a presence of metastases (e.g., predicting a presence of synchronous metastases).

In certain embodiments, the neural network is a trained neural network, having been trained [e.g., to generate, as output, a metastases score representing the prediction of (i) the presence of metastases (e.g., the presence of synchronous metastases) in the subject and/or (ii) the risk of metastases (e.g., the risk of metachronous metastases)] using a plurality of example images each obtained from a particular subject and comprising a graphical representation of suspect regions within a prostate region of the particular subject, said plurality of example images comprising: (A) a plurality of positive example images obtained for subjects known to have (e.g., synchronous) metastases; and (B) a plurality of negative example images obtained for subjects having localized disease (e.g., without metastases).

In certain embodiments, the plurality of positive example images are images obtained for subjects having synchronous metastases and wherein step (c) comprises using the neural network to predict the risk of metastases (e.g., metachronous metastases) for the subject.

In certain embodiments, the subject is or has been determined to have localized prostate cancer, with observable lesions {e.g., as determined via pathological assessment; e.g., as determined based on analysis of the one or more medical images [e.g., and identification of one or more suspect regions meeting one or more criteria (e.g., having a minimum size, intensity, etc.)}confined to a primary tumor volume comprising and/or about the prostate of the subject [e.g., comprising the prostate and a surrounding buffer/margin (e.g., approximately 1, 5, 10, 25 voxels; e.g., approximately 1 mm, 2 mm, 5 mm, 10 mm)] and wherein step (d) comprises predicting, as the risk of metastases, a likelihood that the subject will develop one or more observable lesions outside the primary tumor volume (e.g., outside the prostate and/or its surrounding buffer/margin) (e.g., thereby generating a quantitative prediction of risk that the localized disease will develop into metastatic disease).

In certain embodiments, at step (b) the instructions cause the processor to automatically identify the one or more suspect regions within the prostate volume (e.g., and/or the surrounding buffer/margin), but not identifying any suspect regions outside of the prostate volume and/or a surrounding buffer/margin.

In certain embodiments, no suspect region(s) are identified outside of the prostate volume (e.g., and/or a surrounding buffer/margin thereof).

In certain embodiments, step (c) comprises generating, by the neural network, (e.g., as the likelihood that the subject will develop one or more observable lesions outside the primary tumor volume) a likelihood value representing a risk that lesions will spread outside the primary tumor region (e.g., outside the prostate), within a particular period of time [e.g., within 6 months (synchronous metastasis) or e.g., after greater than 6 months (metachronous metastasis)].

In another aspect, the invention is directed to a method for automatically processing one or more medical images (e.g., 3D images) of a subject and using the processed image(s) to automatically predict presence and/or risk of metastases (e.g., to automatically predict whether localized disease has developed or will develop into metastatic cancer), the method comprising: (a) receiving, by a processor of a computing device, one or more medical images of a primary tumor region of the subject {e.g., a PET/CT image obtained with a PSMA targeted imaging agent, e.g., [F18]DCFPyL (PyL)}; (b) automatically identifying, by the processor, a volume of the image(s) corresponding the primary tumor region within the subject (e.g., segmenting a volume representing the primary tumor region); (c) automatically identifying, by the processor, one or more suspect regions (e.g., hotspots) within the volume corresponding to the primary tumor region; and (d) predicting, by the processor, using a neural network (e.g., a convolutional neural network) (e.g., wherein both the automatically identified primary tumor volume and the automatically identified hotspots are used as inputs of the neural network), (i) a presence of metastases in the subject (e.g., the presence of synchronous metastases) (e.g., predicting whether localized disease has developed into metastatic cancer), and/or (ii) a risk of metastases (e.g., the risk of metachronous metastases) (e.g., predicting whether localized disease will develop into metastatic cancer).

In certain embodiments, the primary tumor region is or comprises one or more organs of the subject (e.g., one or both breasts of the subject; e.g., a colon of the subject; e.g., an esophagus of the subject; e.g., one or both lungs of the subject; e.g., one or both ovaries of the subject; e.g., a pancreas of the subject).

In another aspect, the invention is directed to a system for automatically processing one or more medical images (e.g., 3D images) of a subject and using the processed image(s) to automatically predict presence and/or risk of metastases (e.g., to automatically predict whether localized disease has developed or will develop into metastatic cancer), the system comprising: a processor of a computing device; and memory having instructions stored thereon, wherein the instructions, when executed by the processor, cause the processor to: (a) receive one or more medical images of a primary tumor region of the subject {e.g., a PET/CT image obtained with a PSMA targeted imaging agent, e.g., [F18] DCFPyL (PyL)}; (b) automatically identify a volume of the image(s) corresponding the primary tumor region within the subject (e.g., segmenting a volume representing the primary tumor region); (c) automatically identify one or more suspect regions (e.g., hotspots) within volume corresponding to the primary tumor region; and (d) predict, using a neural network (e.g., a convolutional neural network) (e.g., wherein both the automatically identified primary tumor volume and the automatically identified hotspots are used as inputs of the neural network), (i) presence of metastases in the subject (e.g., predicting whether localized disease has developed into metastatic cancer), and/or (ii) a risk of metastases (e.g., predicting whether localized disease will develop into metastatic cancer).

In certain embodiments, the primary tumor region is or comprises one or more organs of the subject (e.g., one or both breasts of the subject; e.g., a colon of the subject; e.g., an esophagus of the subject; e.g., one or both lungs of the subject; e.g., one or both ovaries of the subject; e.g., a pancreas of the subject).

Features of embodiments described with respect to one aspect of the invention may be applied with respect to another aspect of the invention.

BRIEF DESCRIPTION OF THE DRAWING

The foregoing and other objects, aspects, features, and advantages of the present disclosure will become more apparent and better understood by referring to the following description taken in conjunction with the accompanying drawing, in which.

Figure 1A:
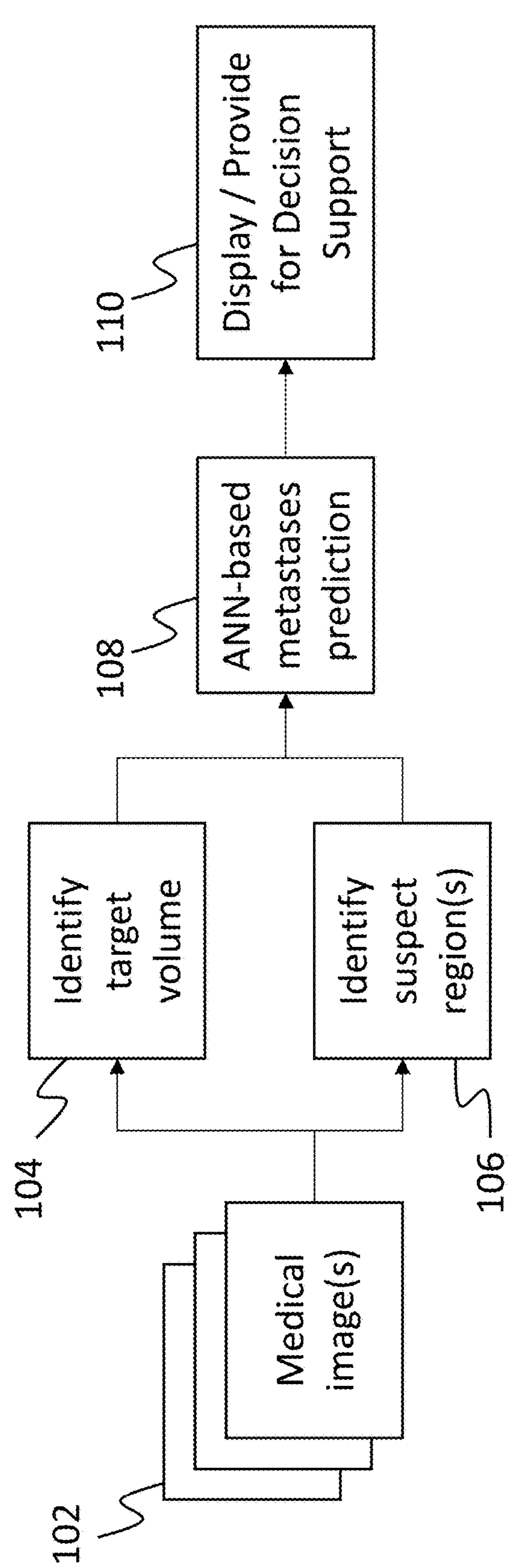
FIG. 1A is a block flow diagram of an example process for determining a machine-learning based metastases prediction via analysis of one or more medical images, according to an illustrative embodiment.

Features and advantages of the present disclosure will become more apparent from the detailed description of certain embodiments that is set forth below, particularly when taken in conjunction with the figures, in which like reference characters identify corresponding elements throughout. In the figures, like reference numbers generally indicate identical, functionally similar, and/or structurally similar elements.

Certain Definitions

In order for the present disclosure to be more readily understood, certain terms are first defined below. Additional definitions for the following terms and other terms are set forth throughout the specification.

A, an: The articles "a" and "an" are used herein to refer to one or to more than one (i.e., at least one) of the grammatical object of the article. By way of example, "an element" means one element or more than one element. Thus, in this specification and the appended claims, the singular forms "a," "an," and "the" include plural references unless the context clearly dictates otherwise. Thus, for example, reference to a pharmaceutical composition comprising "an agent" includes reference to two or more agents.

About, approximately: As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

First, second, etc.: It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed or that the first element must precede the second element in some manner. In addition, unless stated otherwise, a set of elements may comprise one or more elements.

Administering: As used herein, "administering" an agent means introducing a substance (e.g., an imaging agent) into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments.

3D, three-dimensional: As used herein, "3D" or "three-dimensional" with reference to an "image" means conveying information about three dimensions. A 3D image may be rendered as a dataset in three dimensions and/or may be displayed as a set of two-dimensional representations, or as a three-dimensional representation. In certain embodiments, a 3D image is represented as voxel (e.g., volumetric pixel) data.

Image: As used herein, an "image"—for example, a three-dimensional (3D) image of subject, includes any visual representation, such as a photo, a video frame, streaming video, as well as any electronic, digital or mathematical analogue of a photo (e.g., a digital image), video frame, or streaming video, displayed or stored in memory (e.g., a digital image may, but need not be displayed for visual inspection). Any apparatus described herein, in certain embodiments, includes a display for displaying an image or any other result produced by the processor. Any method described herein, in certain embodiments, includes a step of displaying an image or any other result produced via the method. In certain embodiments, an image is a 3D image, conveying information that varies with position within a 3D volume. Such images may, for example, be represented digitally as a 3D matrix (e.g., a N×M×L matrix) with each voxel of a 3D image represented by an element of a 3D matrix. Other representations are also contemplated and included, for example, a 3D matrix may be reshaped as a vector (e.g., a 1×K size vector, where K is a total number of voxels) by stitching each row or column end to end. Examples of images include, for example, medical images, such as bone-scan images (also referred to as scintigraphy images), computed tomography (CT) images, magnetic resonance images (MRIs), optical images (e.g., bright-field microscopy images, fluorescence images, reflection or transmission images, etc.), positron emission tomography (PET) images, single-photon emission tomography (SPECT) images, ultrasound images, x-ray images, and the like. In certain embodiments, a medical image is or comprises a nuclear medicine image, produced from radiation emitted from within a subject being imaged. In certain embodiments, a medical image is or comprises an anatomical image (e.g., a 3D anatomical image) conveying information regarding location and extent of anatomical structures such as internal organs, bones, soft-tissue, and blood vessels, within a subject. Examples of anatomical images include, without limitation, x-ray images, CT images, MRIs, and ultrasound images. In certain embodiments, a medical image is or comprises a functional image (e.g., a 3D functional image) conveying information relating to physiological activities within specific organs and/or tissue, such as metabolism, blood flow, regional chemical composition, absorption, etc. Examples of functional images include, without limitation, nuclear medicine images, such as PET images, SPECT images, as well as other functional imaging modalities, such as functional MRI (fMRI), which measures small changes in blood flow for use in assessing brain activity.

Radionuclide: As used herein, "radionuclide" refers to a moiety comprising a radioactive isotope of at least one element. Exemplary suitable radionuclides include but are not limited to those described herein. In some embodiments, a radionuclide is one used in positron emission tomography (PET). In some embodiments, a radionuclide is one used in single-photon emission computed tomography (SPECT). In some embodiments, a non-limiting list of radionuclides includes $^{99m}$Tc, $^{111}$In, $^{64}$Cu, $^{67}$Ga, $^{68}$Ga, $^{186}$Re, $^{188}$Re, $^{153}$Sm, $^{177}$Lu, $^{67}$Cu, $^{123}$I, $^{124}$I, $^{125}$I, $^{126}$I, $^{131}$I, $^{11}$C, $^{13}$N, $^{15}$O, $^{18}$F, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{105}$Rh, $^{111}$Ag, $^{89}$Zr, $^{225}$Ac, $^{82}$Rb, $^{75}$Br, $^{76}$Br, $^{77}$Br, $^{80}$Br, $^{80m}$Br, $^{82}$Br, $^{83}$Br, $^{21}$At and $^{192}$Ir.

Radiopharmaceutical: As used herein, the term "radiopharmaceutical" refers to a compound comprising a radionuclide. In certain embodiments, radiopharmaceuticals are used for diagnostic and/or therapeutic purposes. In certain embodiments, radiopharmaceuticals include small molecules that are labeled with one or more radionuclide(s), antibodies that are labeled with one or more radionuclide(s), and antigen-binding portions of antibodies that are labeled with one or more radionuclide(s).

Machine learning module: Certain embodiments described herein make use of (e.g., include) software instructions that include one or more machine learning module(s), also referred to herein as artificial intelligence software. As used herein, the term "machine learning module" refers to a computer implemented process (e.g., function) that implements one or more specific machine learning algorithms in order to determine, for a given input (such as an image (e.g., a 2D image; e.g., a 3D image), dataset, and the like) one or more output values. For example, a machine learning module may receive as input a 3D image of a subject (e.g., a CT image; e.g., an MRI), and for each voxel of the image, determine a value that represents a likelihood that the voxel lies within a region of the 3D image that corresponds to a representation of a particular organ or tissue of the subject. In certain embodiments, two or more machine learning modules may be combined and implemented as a single module and/or a single software application. In certain embodiments, two or more machine learning modules may also be implemented separately, e.g., as separate software applications. A machine learning module may be software and/or hardware. For example, a machine learning module may be implemented entirely as software, or certain functions of a CNN module may be carried out via specialized hardware (e.g., via an application specific integrated circuit (ASIC)).

Map: As used herein, the term "map" is understood to mean a visual display, or any data representation that may be interpreted for visual display, which contains spatially-correlated information. For example, a three-dimensional map of a given volume may include a dataset of values of a given quantity that varies in three spatial dimensions throughout the volume. A three-dimensional map may be displayed in two-dimensions (e.g., on a two-dimensional screen, or on a two-dimensional printout).

Metachronous metastases: As used herein the term "metachronous metastases" refers to metastases within a patient that are not detected and/or do not appear until after a particular time interval following initial diagnosis and/or detection of cancer.

Occult metastases: As used herein, the term "occult metastases" refers to metastases that are present within a patient, but not detected during initial pathological examination. In certain embodiments, for example, occult metastases may be undetectable via conventional imaging. For example, a patient may have existing metastases, but they may not yet be of a size that gives rise to observable suspect regions in CT, MRI, or nuclear medicine (e.g., as hotspots) images.

Segmentation map: As used herein, the term "segmentation map" refers to a computer representation that identifies one or more 2D or 3D regions determined by segmenting an image. In certain embodiments, a segmentation map distinguishably identifies multiple different (e.g., segmented) regions, allowing them to be individually and distinguishably accessed and operated upon and/or used for operating on, for example, one or more images.

Subject: As used herein, a "subject" means a human or other mammal (e.g., rodent (mouse, rat, hamster), pig, cat, dog, horse, primate, rabbit, and the like). The term "subject" is used herein interchangeably with the term "patient".

Synchronous metastases: As used herein, the term "synchronous metastases" refers to metastases within a patient that co-exist with the primary cancer tumor at a time of initial diagnosis and/or detection of cancer. In certain embodiments, an initial diagnosis and/or detection of cancer is a detection of a primary tumor and/or one or more lesions within a particular (e.g., single, isolated) organ or tissue region, such as a prostate, breast, liver, lung, colon, or rectum.

Tissue: As used herein, the term "tissue" refers to bone (osseous tissue) as well as soft-tissue.

Whole body: As used herein, the terms "full body" and "whole body" used (interchangeably) in the context of segmentation and other manners of identification of regions within an image of a subject refer to approaches that evaluate a majority (e.g., greater than 50%) of a graphical representation of a subject's body in a 3D anatomical image to identify target tissue regions of interest. In certain embodiments, full body and whole body segmentation refers to identification of target tissue regions within at least an entire torso of a subject. In certain embodiments, portions of limbs are also included, along with a head of the subject.

DETAILED DESCRIPTION

Presented herein are systems and methods for predicting presence and/or risk of metastases in a subject, based on medical image data that reflects presence of localized disease. In particular, among other things, metastatic disease prediction technologies of the present disclosure leverage artificial neural networks (ANNs) to analyze image data that is associated with and reflects presence of localized disease, such as images of regions about a single primary tumor and/or one or more lesions confined to a single tissue region or organ, where cancer was first detected. Among other things, technologies described herein make use of the insight that, while such images of localized disease may not include conventional or express hallmarks of metastatic disease, such as presence of hotspots dispersed outside the primary organ and/or tumor, they nonetheless may reflect patterns, features, such as particular intensity patterns and/or hotspot features, etc. that are indicative of (e.g., correlate with) presence and/or risk of metastases. While such patterns and their relationship/implications for whether a particular patient has or will develop metastatic disease may escape conventional image analysis methods and/or review by human professionals, such as physicians, radiologists, and the like, ANN technologies of the present disclosure can be trained and used to generate predictions of whether a patient has or will develop metastases—i.e., one or more cancerous lesions outside of a primary tumor and/or site (e.g., organ or tissue region) where cancer was originally detected.

Approaches for leveraging machine learning technologies to analyze nuclear medicine images of localized disease in order to predict presence and/or risk of a particular disease state, such as whether a patient has or will develop metastases are described, for example, in U.S. patent application Ser. No. 16/734,609, filed Jan. 6, 2020, and U.S. patent application Ser. No. 17/762,796, filed Mar. 23, 2022 the contents of each of which are incorporated herein in their entirety. The present disclosure extends and improves upon these techniques by incorporating the insight that performance of machine learning techniques can be improved by incorporating an additional channel of input that corresponds to a hotspot mask, identifying automatically segmented hotspot volumes. As described and demonstrated in further detail herein, this additional channel of input improves the machine learning algorithm's ability to identify and focus its attention on important regions in images, allowing it to generate accurate predictions on limited training data.

Figure 1B:
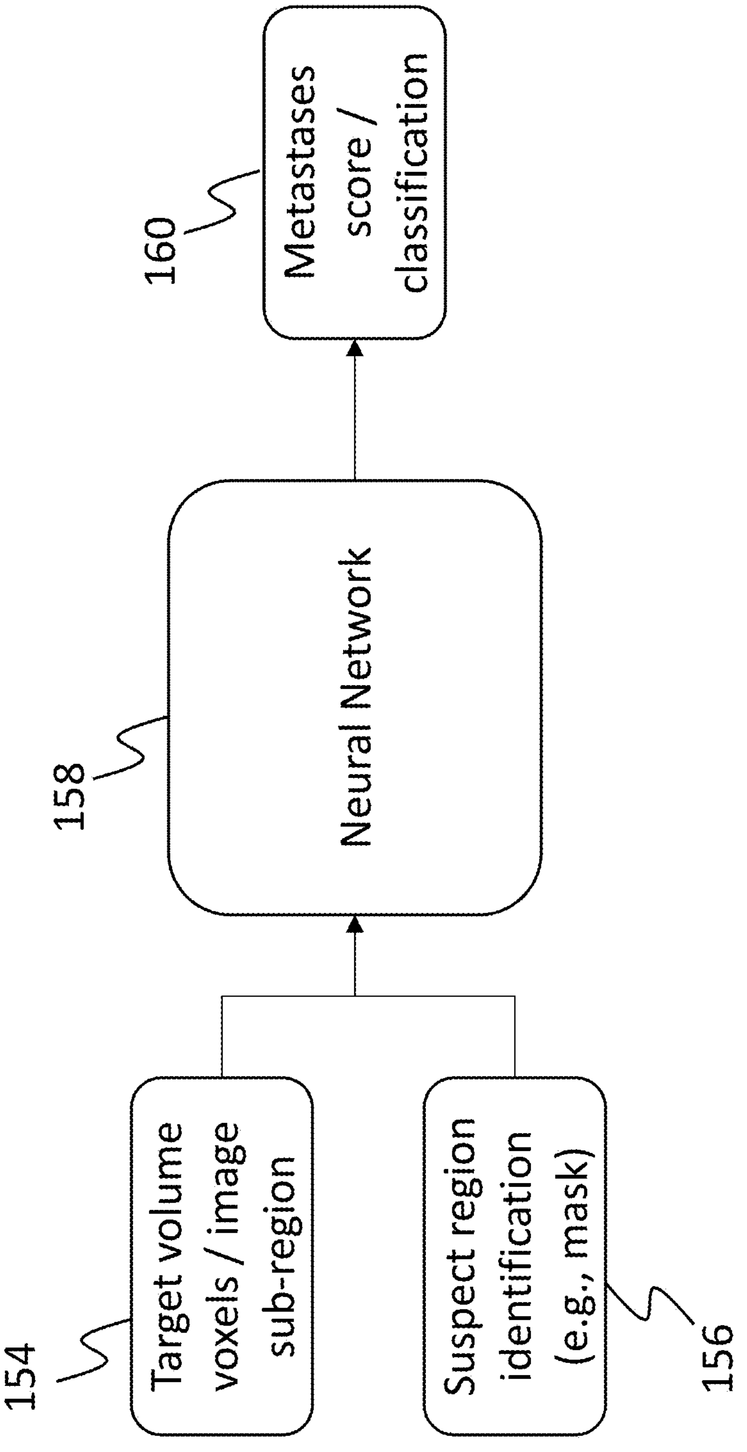
FIG. 1B is a block flow diagram illustrating inputs and outputs of a neural network for generating metastases predictions based on image data input channels, according to an illustrative embodiment.

Accordingly, as shown in FIGS. 1A and 1B, technologies of the present disclosure include processes, such as example process, 100, whereby one or more medical image(s) are received or otherwise obtained 102, by a processor, such as a cloud-based or local image storage and analysis system. In certain embodiments, one or more medical images are or comprise anatomical and functional images, such as co-aligned anatomical and functional image pairs or composite images, comprising an anatomical and functional image acquired at a substantially same time and/or of a substantially same portion of a subject. As described in further detail herein, anatomical images may include images such as computed tomography (CT) images, magnetic resonance images (MRIs), while functional images may include nuclear medicine images, such as positron emission tomography (PET) and single photon emission computed tomography (SPECT) images.

Medical images 102 may be analyzed to identify target volume(s) 104 comprising representations of primary tumor regions that are associated with localized disease, as well as to detect suspect regions 106—portions of images that are determined likely to represent underlying physical lesions within a patient. Such suspect regions may be determined automatically or semi-automatically, for example by a software program, computer-aided analysis technique, such as a machine learning model or other computer-implemented process, with or without interaction and/or review by an operator.

Figure 1C:
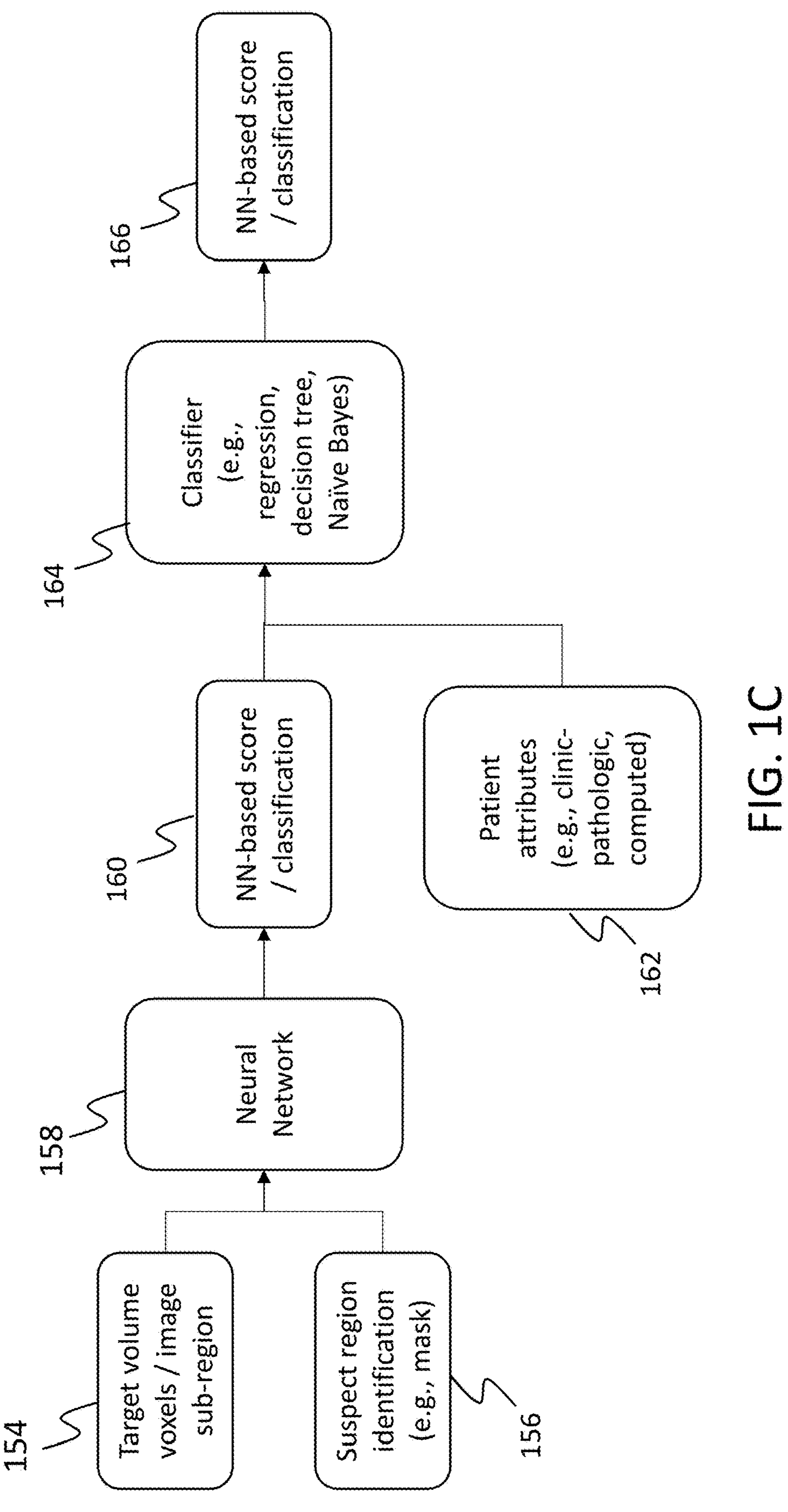
FIG. 1C is a block flow diagram illustrating inputs and outputs of a fused model that combines neural network-based analysis of image data with measured and computed subject attributes, such as clinicopathological data, via a classifier to generate metastases predictions, according to an illustrative embodiment.

As shown in FIG. 1B, in certain embodiments, voxels of medical images within an extracted target volume 154 as well as an identification of detected suspect regions 156 are fed as two channels of input into a neural network 158, which generates, as output, a metastasis prediction 108, 160. A metastasis prediction may be a score or classification. For example, a metastasis score may quantify a likelihood of a patient having or at risk of developing metastases. A metastasis classification may be a binary classification, such as a 0 or 1 value, indicative of whether the patient is likely to have or develop metastatic disease or not. In certain embodiments, as shown in FIG. 1C, neural network determined predictions (e.g., likelihood values) may be combined with patient attributes, such as clinicopathological measurements and/or computed features via a classifier 164 to create a fused model that leverages multiple data sources and types to predict 166 presence and/or risk of metastases (e.g., synchronous metastases) with high accuracy.

In certain embodiments, metastases predictions may represent predictions of whether a subject has or likely will develop metastases. In certain embodiments, metastases predictions may reflect whether a subject has or likely will develop metastases within a particular time-period, e.g., following a date one when the one or more medical images were acquired and/or after initial diagnosis. For example, a metastasis prediction may represent a prediction of whether a subject has or will develop synchronous metastases—i.e., metastases that may already present in the subject (e.g., but not necessarily having been detected)—or metastases that will appear (e.g., and be detectable) within less than a year (e.g., less than six months). In this manner, among other things, approaches of the present disclosure can predict whether or not a given patient is at risk of harboring occult (e.g., undetectable via imaging) metastatic disease that can be manifested by metastatic progression subsequent to curative intent therapy.

Among other things, metastases predictions may be displayed and/or otherwise provided for use in a decision support system 110, to, for example, assist physicians in disease staging, counseling, and treatment course determinations.

As described in further detail herein, nuclear medicine images acquired using prostate specific membrane antigen (PSMA) targeting agents, such as [18F]DCFPyL (PyL™) are of particular interest to prostate cancer staging and diagnosis. [F18]DCFPyL (PyL) is a PSMA targeted imaging agent shown to have greater accuracy, specificity, and sensitivity than conventional imaging in the detection of metastatic disease and it has been established for initial staging. While a primary use of PSMA PET/CT has been to improved staging accuracy, the present disclosure recognizes that there may be untapped data contained within these PET/CT scans that can be used for meaningful prognostic evaluation, namely, to provide added insights into disease biology, including the presence of co-existing metastatic disease.

Among other things, while prostate cancers may, e.g., initially, be localized, certain localized prostate cancers pose a high risk of metastatic progression to lethal disease, while others are at lower risk of such progression, and are less aggressive. While more aggressive disease may warrant an aggressive initial treatment approach, prostate cancers that do not pose a high risk of metastatic progression may be better treated (e.g., particularly in view of potential quality of life reducing side effects from aggressive treatment) via a more targeted and/or less aggressive approach. Accordingly, accurate prognostic information at a time of diagnosis can improve the ability of physicians and their patients to select and achieve better courses of action. Currently, at the clinical stage, serum Prostate Specific Antigen (PSA), Gleason Grade, and percent positive cores are typically used to assess risk of metastatic progression, and may be combined with transcriptomic data. Typically, however, current approaches utilize imaging scans only to determine stage (e.g., metastatic or not, and number of lesions). Technologies of the present disclosure allow for expanded use of imaging data, in particular, in fulfilling a need for accurate prognostic information early on, allowing for prediction of metastatic disease risk and its use in improving patient outcomes.

Moreover, in certain embodiments, metastases risk prediction technologies described herein may leverage the insights that machine learning models that are trained on certain types of, e.g., more plentiful, data, can be used to generate predictions about disease prediction that for which exact examples can be more time consuming and/or challenging to obtain, resulting in insufficient data. For example, as demonstrated herein, it is possible to train a machine learning model on images for patients with synchronous metastases—i.e., for which metastases already have been observed, or will be observed within a very short time frame, and then, once the model is a trained, a new image, of a new patient, can be received and evaluated (by the model) to generate a metastasis score/prediction. Even if this new patient presents with localized disease (e.g., no lesion spread outside a localized primary tumor region) in the near term, the generated metastases score can be used as an accurate predictor of a risk that the patient will develop metastases well into the future, for example, after curative therapy.

From a practical standpoint, training a machine learning model on images of patients with synchronous metastases is advantageous since it is generally known whether a patient has synchronous metastases or not when they are imaged or shortly thereafter (e.g., since six (6) months is a short time-frame). That is, some of the images themselves might have metastases showing up in them, and for the ones that might not, it will be apparent quickly (e.g., within six months) if the patient does or doesn't get synchronous metastases. Accordingly, medical images labeled as corresponding to patients with synchronous metastases or not are a relatively abundant dataset. On the other hand, for metachronous metastases/metastases that will develop in the future, to obtain directly corresponding data, one would need to take an image of a patient that presents with localized disease, wait until they are treated, then watch them for a relatively long period of time (e.g., years), to determine if their cancer spreads (metastasizes), and then, finally, label the images accordingly (i.e., label medical images according to whether each patient's cancer metastasized or not, several years later).

To address this challenge, among other things, as Example 3 described herein, uses a small dataset (e.g., not enough to directly train a neural network model, but enough to tests hypotheses) of medical images where patients initially presented with localized disease, and did not develop metastases until a significant time period later, e.g., after curative intent therapy. A model that was trained on a different dataset—of synchronous metastases images—may be used to analyze the early-stage images of patients that presented with localized disease and generate a metastases score that accurately classified patients that did or did not develop metachronous metastases. Accordingly, in certain embodiments, technologies described herein address challenges associated with limited data availability, allowing for machine learning models trained on certain images of synchronous metastases to then be used, at inference stages, to predict whether a subject will develop metachronous metastases.

While described herein with particular emphasis on and/or relevance to prostate cancer, metastases prediction technologies of the present disclosure may be utilized for other types of cancer, such breast cancer, colorectal cancer, esophageal cancer, lung cancer, ovarian cancer, pancreatic cancer, e.g., to predict, based on images of localized disease within a target volume corresponding to a primary tumor region within the subject, will metastases. For example, for a subject with breast cancer, a primary tumor region may be or comprise one or both breasts of the subject; for a subject with colorectal cancer, a primary tumor region may be or comprises a colon of the subject; for a subject with esophageal cancer, a primary tumor region may be or comprises an esophagus of the subject; for a subject with lung cancer, a primary tumor region may be or comprises one or both lungs of the subject; for a subject with ovarian cancer, a primary tumor region may be or comprises one or both ovaries of the subject; for a subject with pancreatic cancer, a primary tumor region may be or comprises a pancreas of the subject; etc.

A. NUCLEAR MEDICINE IMAGES

Nuclear medicine images may be obtained using a nuclear medicine imaging modality such as bone scan imaging (also referred to as scintigraphy), Positron Emission Tomography (PET) imaging, and Single-Photon Emission Tomography (SPECT) imaging.

In certain embodiments, nuclear medicine images are obtained using imaging agents comprising radiopharmaceuticals. Nuclear medicine images may be obtained following administration of a radiopharmaceutical to a patient (e.g., a human subject), and provide information regarding the distribution of the radiopharmaceutical within the patient.

Nuclear medicine imaging techniques detect radiation emitted from the radionuclides of radiopharmaceuticals to form an image. The distribution of a particular radiopharmaceutical within a patient may be determined by biological mechanisms such as blood flow or perfusion, as well as by specific enzymatic or receptor binding interactions. Different radiopharmaceuticals may be designed to take advantage of different biological mechanisms and/or particular specific enzymatic or receptor binding interactions and thus, when administered to a patient, selectively concentrate within particular types of tissue and/or regions within the patient. Greater amounts of radiation are emitted from regions within the patient that have higher concentrations of radiopharmaceutical than other regions, such that these regions appear brighter in nuclear medicine images. Accordingly, intensity variations within a nuclear medicine image can be used to map the distribution of radiopharmaceutical within the patient. This mapped distribution of radiopharmaceutical within the patient can be used to, for example, infer the presence of cancerous tissue within various regions of the patient's body. In certain embodiments, intensities of voxels of a nuclear medicine image, for example a PET image, represent standard uptake values (SUVs) (e.g., having been calibrated for injected radiopharmaceutical dose and/or patient weight).

For example, upon administration to a patient, technetium 99m methylenediphosphonate ($^{99m}$Tc MDP) selectively accumulates within the skeletal region of the patient, in particular at sites with abnormal osteogenesis associated with malignant bone lesions. The selective concentration of radiopharmaceutical at these sites produces identifiable hotspots—localized regions of high intensity—in nuclear medicine images. Accordingly, presence of malignant bone lesions associated with metastatic prostate cancer can be inferred by identifying such hotspots within a whole-body scan of the patient. In certain embodiments, analyzing intensity variations in whole-body scans obtained following administration of $^{99m}$Tc MDP to a patient, such as by detecting and evaluating features of hotspots, can be used to compute, risk indices that correlate with patient overall survival and other prognostic metrics indicative of disease state, progression, treatment efficacy, and the like. In certain embodiments, other radiopharmaceuticals can also be used in a similar fashion to $^{99m}$Tc MDP.

In certain embodiments, the particular radiopharmaceutical used depends on the particular nuclear medicine imaging modality used. For example, 18F sodium fluoride (NaF) also accumulates in bone lesions, similar to $^{99m}$Tc MDP, but can be used with PET imaging. In certain embodiments, PET imaging may also utilize a radioactive form of the vitamin choline, which is readily absorbed by prostate cancer cells. In certain embodiments, PET imaging may be performed with [18F]Fluorodeoxyglucose, abbreviated [18F]FDG, which is an 18F labeled glucose analog. Without wishing to be bound to any particular theory, uptake of 18FFDG is believed to be a marker for glucose uptake in tissue, which is correlated with metabolism and, accordingly, may serve as a marker for cancer.

In certain embodiments, radiopharmaceuticals that selectively bind to particular proteins or receptors of interest—particularly those whose expression is increased in cancerous tissue may be used. Such proteins or receptors of interest include, but are not limited to tumor antigens, such as CEA, which is expressed in colorectal carcinomas, Her2/neu, which is expressed in multiple cancers, BRCA 1 and BRCA 2, expressed in breast and ovarian cancers; and TRP-1 and -2, expressed in melanoma.

For example, human prostate-specific membrane antigen (PSMA) is upregulated in prostate cancer, including metastatic disease. PSMA is expressed by virtually all prostate cancers and its expression is further increased in poorly differentiated, metastatic and hormone refractory carcinomas. Accordingly, radiopharmaceuticals that comprise PSMA binding agents (e.g., compounds that a high affinity to PSMA) labelled with one or more radionuclide(s) can be used to obtain nuclear medicine images of a patient from which the presence and/or state of prostate cancer within a variety of regions (e.g., including, but not limited to skeletal regions) of the patient can be assessed. In certain embodiments, nuclear medicine images obtained using PSMA binding agents are used to identify the presence of cancerous tissue within the prostate, when the disease is in a localized state. In certain embodiments, nuclear medicine images obtained using radiopharmaceuticals comprising PSMA binding agents are used to identify the presence of cancerous tissue within a variety of regions that include not only the prostate, but also other organs and tissue regions such as lungs, lymph nodes, and bones, as is relevant when the disease is metastatic.

In particular, upon administration to a patient, radionuclide labelled PSMA binding agents selectively accumulate within cancerous tissue, based on their affinity to PSMA. In a similar manner to that described above with regard to $^{99m}$Tc MDP, the selective concentration of radionuclide labelled PSMA binding agents at particular sites within the patient produces detectable hotspots in nuclear medicine images. As PSMA binding agents concentrate within a variety of cancerous tissues and regions of the body expressing PSMA, localized cancer within a prostate of the patient and/or metastatic cancer in various regions of the patient's body can be detected, and evaluated. Risk indices that correlate with patient overall survival and other prognostic metrics indicative of disease state, progression, treatment efficacy, and the like, can be computed based on automated analysis of intensity variations in nuclear medicine images obtained following administration of a PSMA binding agent radiopharmaceutical to a patient.

A variety of radionuclide labelled PSMA binding agents may be used as radiopharmaceutical imaging agents for nuclear medicine imaging to detect and evaluate prostate cancer. In certain embodiments, the particular radionuclide labelled PSMA binding agent that is used depends on factors such as the particular imaging modality (e.g., PET; e.g., SPECT) and the particular regions (e.g., organs) of the patient to be imaged. For example, certain radionuclide labelled PSMA binding agents are suited for PET imaging, while others are suited for SPECT imaging. For example, certain radionuclide labelled PSMA binding agents facilitate imaging a prostate of the patient, and are used primarily when the disease is localized, while others facilitate imaging organs and regions throughout the patient's body, and are useful for evaluating metastatic prostate cancer.

Several exemplary PSMA binding agents and radionuclide labelled versions thereof are described in further detail in Section H herein, as well as in U.S. Pat. Nos. 8,778,305, 8,211,401, and 8,962,799, the contents of each of which are incorporated herein by reference in their entireties.

B. IMAGE SEGMENTATION

Nuclear medicine images are functional images. Functional images convey information relating to physiological activities within specific organs and/or tissue, such as metabolism, blood flow, regional chemical composition, and/or absorption. In certain embodiments, nuclear medicine images are acquired and/or analyzed in combination with anatomical images, such as computed tomography (CT) images. Anatomical images provide information regarding location and extent of anatomical structures such as internal organs, bones, soft-tissue, and blood vessels, within a subject. Examples of anatomical images include, without limitation, x-ray images, CT images, magnetic resonance images, and ultrasound images.

Accordingly, in certain embodiments, anatomical images can be analyzed together with nuclear medicine images in order to provide anatomical context for the functional information that they (nuclear medicine images) convey. For example, while nuclear medicine images, such as PET and SPECT convey a three-dimensional distribution of radiopharmaceutical within a subject, adding anatomical context from an anatomical imaging modality, such as CT imaging, allows one to determine the particular organs, soft-tissue regions, bones, etc. that radiopharmaceutical has accumulated in.

For example, a functional image may be aligned with an anatomical image so that locations within each image that correspond to a same physical location—and therefore correspond to each other—can be identified. For example, coordinates and/or pixels/voxels within a functional image and an anatomical image may be defined with respect to a common coordinate system, or a mapping (i.e., a functional relationship) between voxels within the anatomical image and voxels within the functional image established. In this manner, one or more voxels within an anatomical image and one or more voxels within a functional image that represent a same physical location or volume can be identified as corresponding to each other.

In certain embodiments, the aligned pair are a composite image, such as a PET/CT or SPECT/CT. In certain embodiments, an anatomical image (e.g., a 3D anatomical image, such as a CT image) and a functional image (e.g., a 3D functional image, such as a PET or SPECT image) are acquired using separate anatomical and functional imaging modalities, respectively. In certain embodiments, an anatomical image (e.g., a 3D anatomical image, such as a CT image) and a functional image (e.g., a 3D functional image, such as a PET or SPECT image) are acquired using a single multimodality imaging system. A functional image and an anatomical image may, for example, be acquired via two scans using a single multimodal imaging system—for example first performing a CT scan and then, second, performing a PET scan—during which a subject remains in a substantially fixed position.

In certain embodiments, 3D boundaries of particular tissue regions of interest can be accurately identified by analyzing 3D anatomical images. For example, automated segmentation of 3D anatomical images can be performed to segment 3D boundaries of regions such as particular organs, organ sub-regions and soft-tissue regions, as well as bone. In certain embodiments, organs such as a prostate, urinary bladder, liver, aorta (e.g., portions of an aorta, such as a thoracic aorta), a parotid gland, etc., are segmented. In certain embodiments, one or more particular bones are segmented. In certain embodiments, an overall skeleton is segmented.

In certain embodiments, automated segmentation of 3D anatomical images may be performed using one or more machine learning modules that are trained to receive a 3D anatomical image and/or a portion thereof, as input, and segment one or more particular regions of interest, producing a 3D segmentation map as output. For example as described in PCT publication WO/2020/144134, entitled "Systems and Methods for Platform Agnostic Whole Body Segmentation," and published Jul. 16, 2020, the contents of which are incorporated herein by reference in their entirety, multiple machine learning modules implementing convolutional neural networks (CNNs) may be used to segment 3D anatomical images, such as CT images, of a whole body of a subject and thereby create a 3D segmentation map that identifies multiple target tissue regions across a subject's body.

In certain embodiments, for example to segment certain organs where functional images are believed to provide additional useful information that facilitate segmentation, a machine learning module may receive both an anatomical image and a functional image as input, for example as two different channels of input (e.g., analogous to multiple color channels in a color, RGB, image) and use these two inputs to determine an anatomical segmentation. This, multi-channel, approach is described in further detail in U.S. Patent Publication No. US 2021/0334974 A1, entitled "Systems and Methods for Deep-Learning-Based Segmentation of Composite Images," and published Oct. 28, 2021, the contents of which is hereby incorporated by reference in its entirety.

Figure 2:
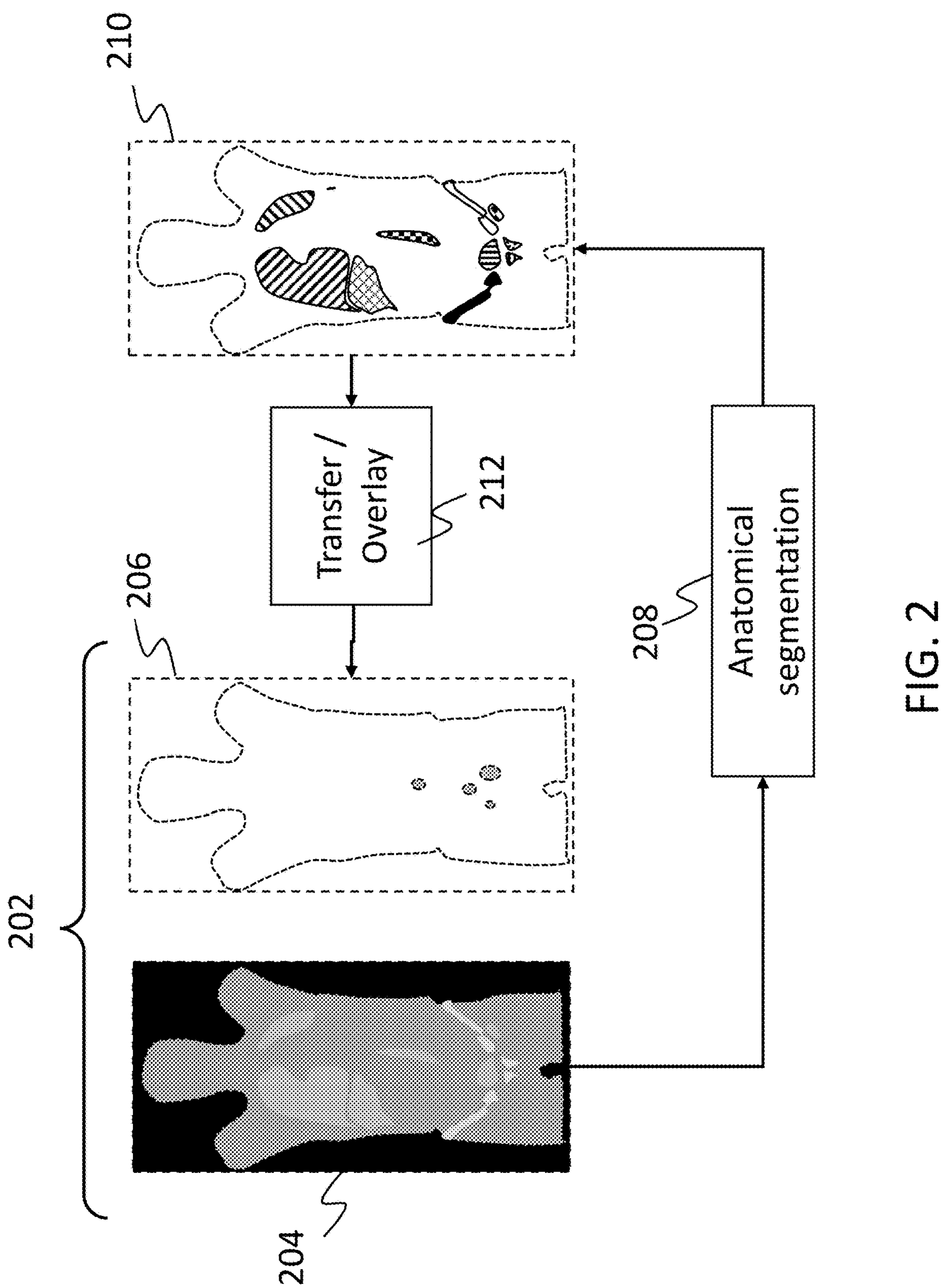
FIG. 2 is a diagram illustrating an example process for segmenting an anatomical image and identifying anatomical boundaries in a co-aligned functional image, according to an illustrative embodiment.

In certain embodiments, as illustrated FIG. 2, an anatomical image 204 (e.g., a 3D anatomical image, such as a CT image) and a functional image 206 (e.g., a 3D functional image, such as a PET or SPECT image) may be aligned with (e.g., co-registered to) each other, for example as in a composite image 202 such as a PET/CT image. Anatomical image 204 may be segmented 208 to create a segmentation map 210 (e.g., a 3D segmentation map) that distinguishably identifies one or more tissue regions and/or sub-regions of interest, such as one or more particular organs and/or bones. Segmentation map 210, having been created from anatomical image 204 is aligned with anatomical image 204, which, in turn, is aligned with functional image 206. Accordingly, boundaries of particular regions (e.g., segmentation masks), such as particular organs and/or bones, identified via segmentation map 210 can be transferred to and/or overlaid 212 upon functional image 206 to identify volumes within functional image 206 for purposes of classifying hotspots, and determining useful indices that serve as measures and/or predictions of cancer status, progression, and response to treatment. Segmentation maps and masks may also be displayed, for example as a graphical representation overlaid on a medical image to guide physicians and other medical practitioners.

C. LESION DETECTION AND SEGMENTATION

In certain embodiments, approaches described herein include techniques for detecting and characterizing lesions within a subject via (e.g., automated) analysis of medical images, such as nuclear medicine images. As described herein, in certain embodiments, hotspots are localized (e.g., contiguous) regions of high intensity, relative to their surroundings, within images, such as 3D functional images and may be indicative of a potential cancerous lesion present within a subject.

A variety of approaches may be used for detecting, segmenting, and classifying hotspots. In certain embodiments, hotspots are detected and segmented using analytical methods, such as filtering techniques including, but not limited to, a difference of Gaussians (DoG) filter and a Laplacian of Gaussians (LoG) filter. In certain embodiments, hotspots are segmented using a machine learning module that receives, as input, a 3D functional image, such as a PET image, and generates, as output a hotspot segmentation map (a "hotspot map") that differentiates boundaries of identified hotspots from background. In certain embodiments, each segmented hotspot within a hotspot map is individually identifiable (e.g., individually labelled). In certain embodiments, a machine learning module used for segmenting hotspots may take as input, in addition to a 3D functional image, one or both of a 3D anatomical image (e.g., a CT image) and a 3D anatomical segmentation map. The 3D anatomical segmentation map may be generated via automated segmentation (e.g., as described herein) of the 3D anatomical image.

In certain embodiments, segmented hotspots may be classified according to an anatomical region in which they are located. For example, in certain embodiments, locations of individual segmented hotspots within a hotspot map (representing and identifying segmented hotspots) may be compared with 3D boundaries of segmented tissue regions, such as various organs and bones, within a 3D anatomical segmentation map and labeled according to their location, e.g., based on proximity to and/or overlap with particular organs. In certain embodiments, a machine learning module may be used to classify hotspots. For example, in certain embodiments, a machine learning module may generate, as output, a hotspot map in which segmented hotspots are not only individually labeled and identifiable (e.g., distinguishable from each other), but are also labeled, for example, as corresponding to one of a bone, lymph, or prostate lesion. In certain embodiments, one or more machine learning modules may be combined with each other, as well as with analytical segmentation (e.g., thresholding) techniques to perform various tasks in parallel and in sequence to create a final labeled hotspot map.

Various approaches for performing detailed segmentation of 3D anatomical images and identification of hotspots representing lesions in 3D functional images, which may be used with various approaches described herein, are described in PCT publication WO/2020/144134, entitled "Systems and Methods for Platform Agnostic Whole Body Segmentation," and published Jul. 16, 2020, U.S. Patent Publication No. US 2021/0334974 A1, entitled "Systems and Methods for Deep-Learning-Based Segmentation of Composite Images," and published Oct. 28, 2021, and PCT publication WO/2022/008374, entitled "Systems and Methods for Artificial Intelligence-Based Image Analysis for Detection and Characterization of Lesions," and published Jan. 13, 2022, the contents of each of which is incorporated herein in its entirety.

Figure 3:
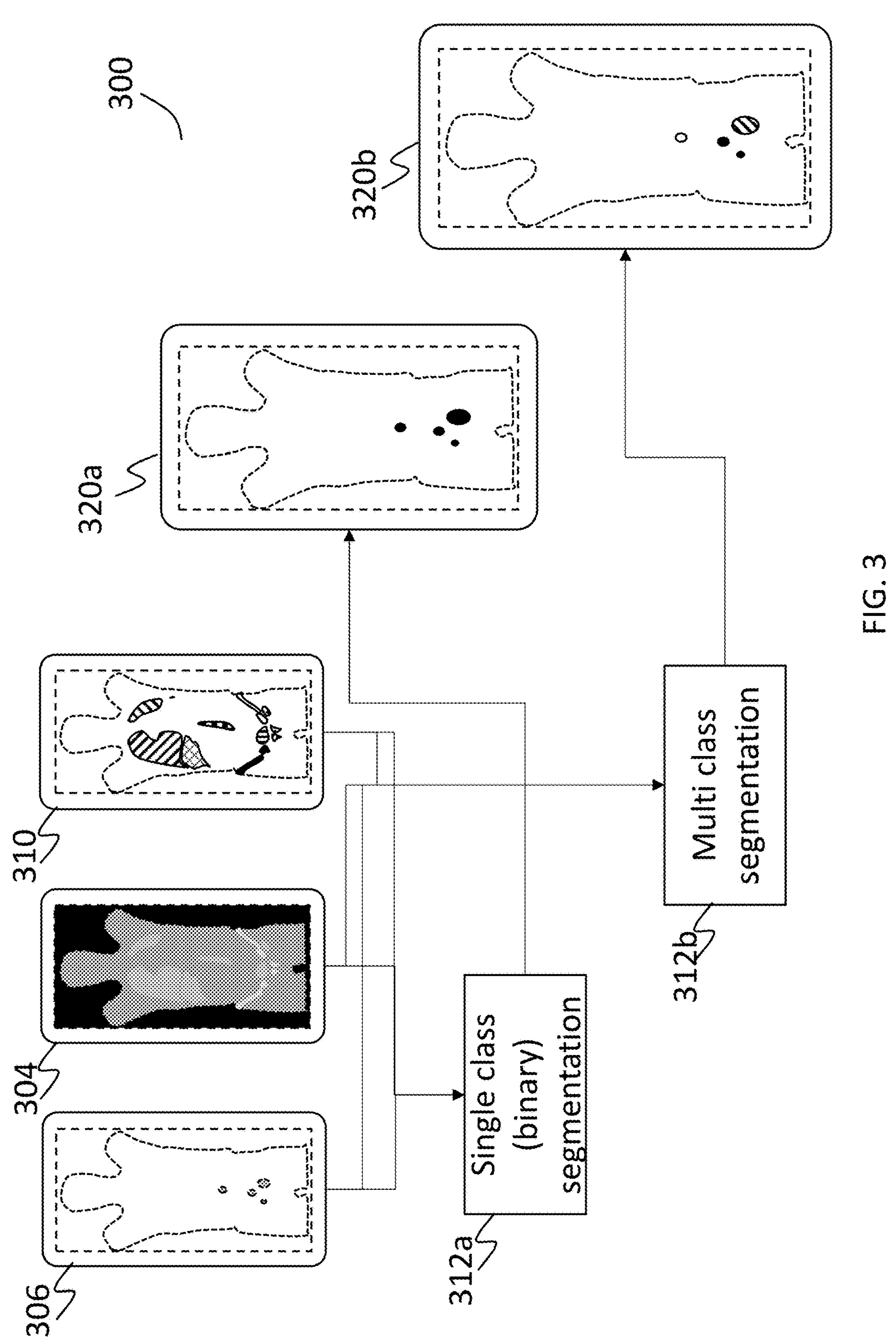
FIG. 3 is a diagram illustrating an example process for segmenting and classifying hotspots, according to an illustrative embodiment.

FIG. 3 shows an example process 300 for segmenting and classifying hotspots, based on an example approach described in further detail in PCT publication WO/2022/008374, entitled "Systems and Methods for Artificial Intelligence-Based Image Analysis for Detection and Characterization of Lesions," and published Jan. 13, 2022. The approach illustrated in FIG. 3 uses two machine learning modules, each of which receives, as input, 3D functional image 306, 3D anatomical image 304, and 3D anatomical segmentation map 310. Machine learning module 312*a* is a binary classifier that generates a single-class hotspot map 320*a*, by labeling voxels as hotspot or background (not a hotspot). Machine learning module 312*b* performs multi-class segmentation, and generates multi-class hotspot map 320*b*, in which hotspots are both segmented and labeled as one of three classes—prostate, lymph, or bone. Among other things, classifying hotspots in this manner—via a machine learning module 312*b* (e.g., as opposed to directly comparing hotspot locations with segmented boundaries from segmentation map 310)—obviates a need to segment certain regions. For example, in certain embodiments, machine learning module 312*b* may classify hotspots as belonging to prostate, lymph, or bone, without a prostate region having be identified and segmented from 3D anatomical image 304 (e.g., in certain embodiments, 3D anatomical segmentation map 310 does not comprise a prostate region). In certain embodiments, hotspot maps 320*a* and 320*b* are merged, for example by transferring labels from multi-class hotspot map 320*b* to the hotspot segmentations identified in single-class hotspot map 320*a* (e.g., based on overlap). Without wishing to be bound to any particular theory, it is believed that this approach combines improved segmentation and detection of hotspots from single class machine learning module 312*a* with classification results from multi-class machine learning module 312*b*. In certain embodiments, hotspot regions identified via this final, merged, hotspot map are further refined, using an analytical technique such as an adaptive thresholding technique described in PCT publication WO/2022/008374, entitled "Systems and Methods for Artificial Intelligence-Based Image Analysis for Detection and Characterization of Lesions," and published Jan. 13, 2022.

D. HOTSPOT AND PATIENT DISEASE STATE QUANTIFICATION

In certain embodiments, one or more individual hotspot quantification measures are computed for (e.g., each) individual 3D hotspot volumes. In certain embodiments, each particular individual hotspot quantification measures quantifies an intensity and/or size (e.g., volume) of an individual 3D hotspot volume. Examples of individual hotspot quantification measures include measures of hotspot intensity, such as a maximum intensity, a mean intensity, a peak intensity and measures of hotspot size, such as a hotspot volume. In certain embodiments, hotspot intensity measures include an individual lesion index value that maps an intensity of voxels within a particular 3D hotspot volume to a value on a standardized scale. Such lesion index values are described in further detail in PCT/EP2020/050132, filed Jan. 6, 2020, and PCT/EP2021/068337, filed Jul. 2, 2021, the content of each of which is hereby incorporated by reference in its entirety. Calculation of lesion index values typically includes calculation of reference intensity values within particular reference tissue regions, such as an aorta portion (also referred to as blood pool) and/or a liver.

In certain embodiments, hotspot features are used and/or combined to provide measures of disease state and/or progression in a patient. Such approaches are described in further detail, for example, in U.S. patent application Ser. No. 18/207,246, filed Jul. 8, 2023, the content of which is hereby incorporated by reference in its entirety.

E. NEURAL NETWORK-BASED PREDICTION OF METASTASES

Figure 4A:
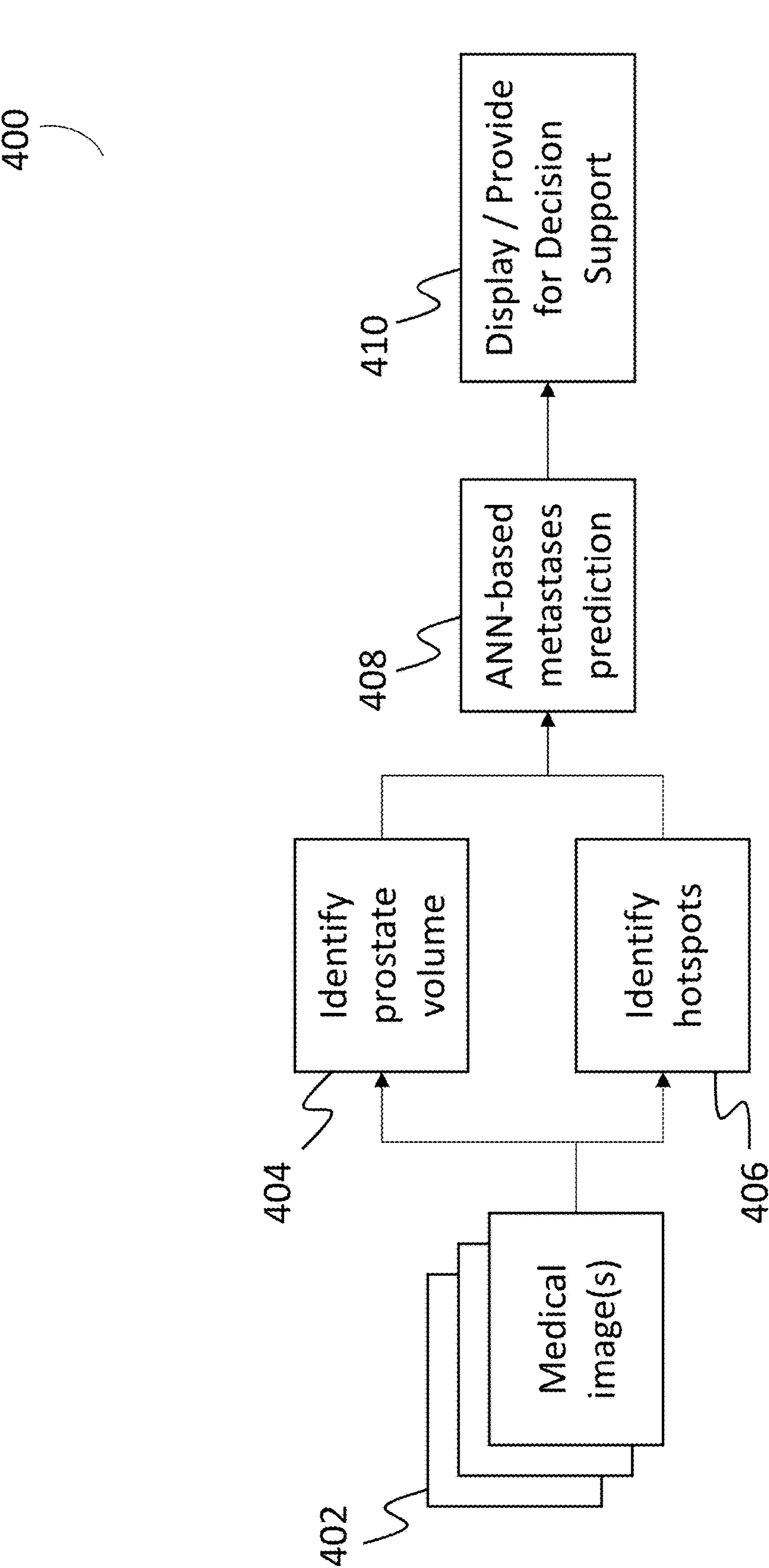
FIG. 4A is a block flow diagram of an example process for determining a machine-learning based metastases prediction via analysis of one or more medical images of localized prostate cancer, according to an illustrative embodiment.

Turning to FIG. 4A, in certain embodiments, image analysis technologies of the present disclosure leverage techniques for detecting, segmenting, and quantifying hotspots to improve accuracy of machine learning models in prediction of metastatic disease risk based on images of primary tumor.

For example, FIG. 4A shows an example process 400 for predicting metastatic disease risk for a subject presenting (e.g., having been diagnosed with) localized prostate cancer. As shown in FIG. 4A, one or more medical images of the subject are obtained 402. These may be medical images acquired and/or used to arrive at an initial detection and/or diagnosis of localized disease or may have been obtained in (e.g., additional) follow up visits. In certain embodiments, one or more medical images are obtained within a particular (e.g., short) time period following initial diagnosis and/or detection, such as within a month, three months, six months, or a year. In certain embodiments, one or more medical images are obtained prior to initial treatment. For example, as described in further detail herein, medical images may be obtained and analyzed using the metastatic disease prediction technologies of the present disclosure in order to assist with determining a course of treatment, for example whether a relatively mild, targeted treatment is appropriate or if a more aggressive course is warranted at the outset, for example if a patient is determined to be at high risk for having or developing synchronous metastases.

In certain embodiments, one or more medical images are or comprise anatomical images, such as CT images or MRIs. In certain embodiments, one or more medical images are or comprise functional images, such as nuclear medicine images, including, but not limited to, PET and SPECT images. In certain embodiments, one or more medical images are or comprise one or more pairs of co-aligned anatomical and functional images. In certain embodiments, one or more medical images are or comprise one or more composite or fused anatomical and functional images, for example PET/CT and/or SPECT/CT images.

E.i. Input Channels and Features

Figure 4B:
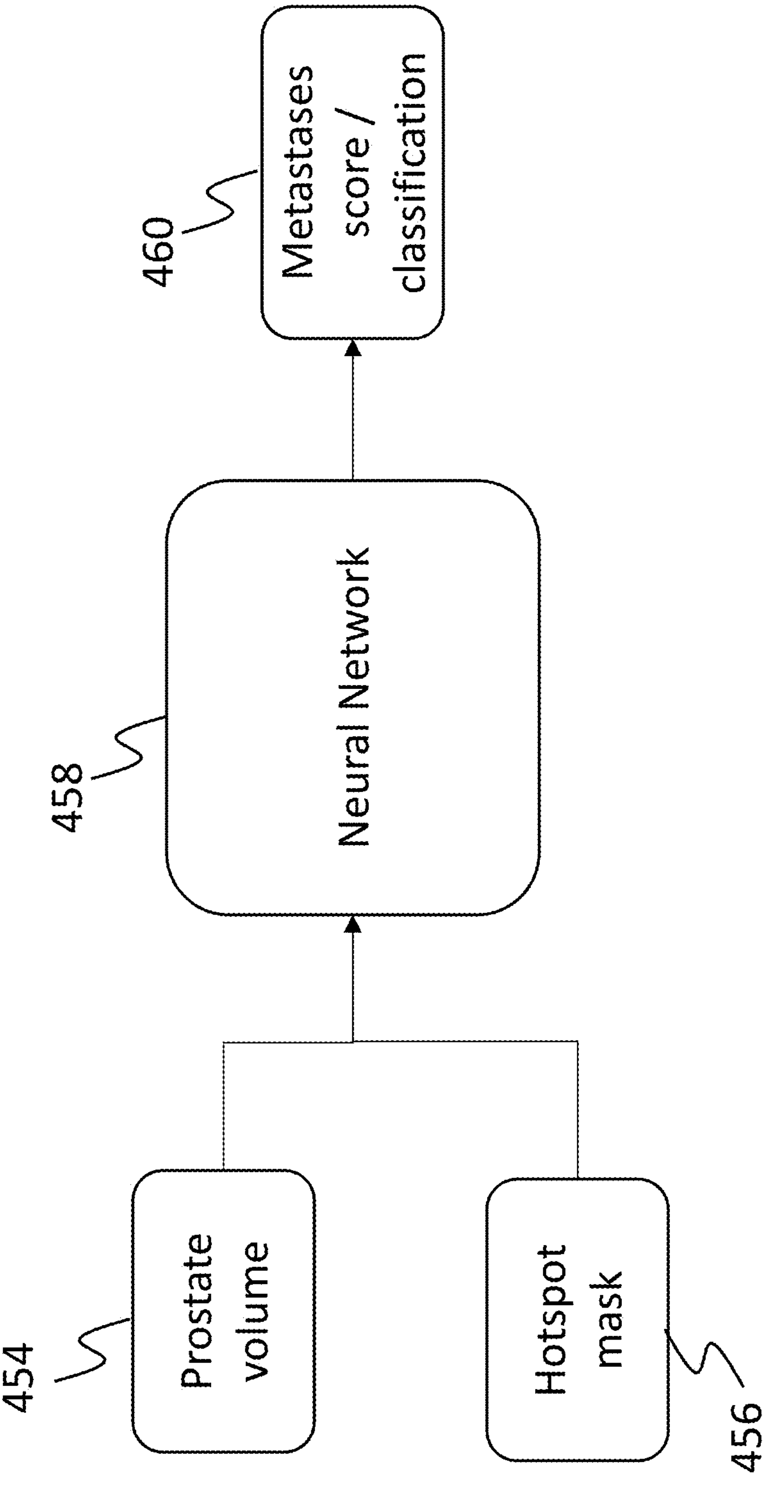
FIG. 4B is a block flow diagram illustrating inputs and outputs of a neural network for generating metastases predictions based on prostate image data input channels, according to an illustrative embodiment.

Medical images may be analyzed, for example as described in sections A-D, herein, to identify (i) a volume that corresponds to or comprises a prostate of the subject 404, which is the site of primary tumor and/or localized disease in prostate cancer, and (ii) suspect regions of images likely to represent underlying (e.g., individual) lesions 406. As shown in FIG. 4B, these identified regions—the prostate volume 454 and suspect regions (e.g., a hotspot mask, 456)—may then be used as or to create two channels of input for a machine learning model 458.

For example, as described herein (e.g., in Section B, above), an anatomical and nuclear medicine composite image, such as a PET/CT image, may be analyzed to automatically identify a volume of interest (VOI) that corresponds to or comprises a representation of a prostate within the anatomical image. The VOI may then be mapped to the co-aligned nuclear medicine image of the composite image and used to identify a corresponding volume within the nuclear medicine image. Voxels within this corresponding nuclear medicine image volume may then be used as a first, prostate intensity, channel of input.

Suspect regions can be identified by automatically detecting hotspots within the nuclear medicine image, for example, as described in section C, above. In certain embodiments, a 3D hotspot mask that identifies volumes of hotspots within the functional image may then be used as a second, hotspot mask channel, of input to the machine learning model.

E.ii Model Outputs

Turning again to FIGS. 4A and 4B, identified prostate volumes and suspect regions may be used to determine a metastases prediction 408, 460. As shown in FIG. 4B, in certain embodiments, a machine learning model may generate, as output, a metastases score or classification 460 based (at least in part) on its received prostate intensity and hotspot mask input channels. For example, a machine learning model may generate, as a metastases score, a likelihood value (e.g., having a value ranging from 0 to 1) that represents a likelihood that a patient has or will develop metastases, for example within a particular time window (e.g., synchronous metastases). In certain embodiments, a binary classification may be determined using a generated likelihood value, for example by comparing it to a threshold value.

In certain embodiments, a multi-class classification approach is used, whereby a machine learning model generates, as output, a plurality of likelihood values, representing likelihoods of particular types and/or categories of metastases, as determined by the machine learning model.

E.iii Model Architectures

A variety of machine learning architectures may be used in connection with the approaches described herein. In certain embodiments, machine learning models used for generating metastases predictions are neural networks (e.g., ANNs). In certain embodiments, in particular, CNNs are used.

E.iv Fused Models

Figure 4C:
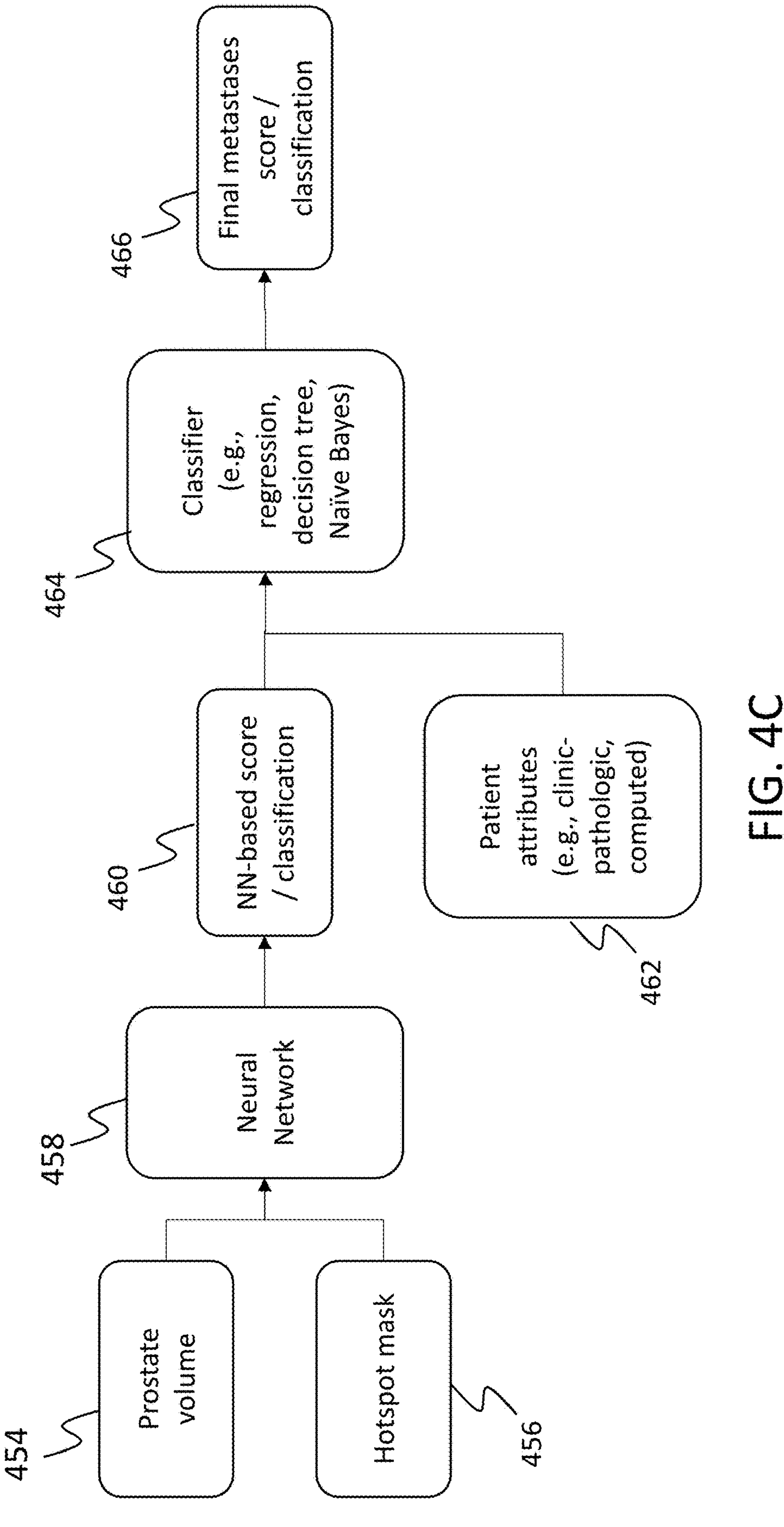
FIG. 4C is a block flow diagram illustrating inputs and outputs of a fused model that combines neural network-based analysis of prostate image data with measured and computed patient attributes, such as clinicopathological data, via a classifier to generate metastases predictions, according to an illustrative embodiment.

Turning to FIG. 4C, as described herein, in certain embodiments, spatial image analysis approaches using a CNN model may be combined with other patient attributes such as measured and computed clinicopathologic features to create a fused model. For example, in certain embodiments, CNN model output 460 may be used as input, together with patient attributes 462, to a classifier 464 to determine a metastases score/classification 466.

Certain patient attributes, described in further detail herein (e.g., in the Examples) that may be used include, without limitation, one or more of the following: PSA, pathologic grade, percent positive cores, cores positive, Primary Score, miTNM, PSMA expression score, uptake SUV peak value, uptake prostate zone, uptake type (focal vs. diffuse), uptake extends outside prostate, aorta SUV mean, liver SUV mean, overall upstaging risk, N upstaging, M upstaging.

Various classifier models may be used, including, without limitation, logistic regression models, support vector machines, decision trees (e.g., random forests, XGboost), Naïve Bayes classifiers, and the like.

E.v Prognosis at Subsequent Time Points and Following Therapy

In certain embodiments, metastasis prediction technologies of the present disclosure may be used to predict whether a patient has or will develop metastases. For example, in certain embodiments, a patient may initially present with localized disease, and medical images may be indicative of a finding of localized disease.

For example, in certain embodiments, a medical image is indicative of localized disease if lesions appearing in the medical image are limited to (e.g., locations within) a primary tumor region. For example, a patient may initially be diagnosed with prostate cancer and medical images, such as CT, PET, PET/CT, etc. images, show representations of lesions, such as hotspots within a PET image, in a primary tumor volume—e.g., a prostate region [e.g., and/or, optionally, a volume enclosing a prostate and tissue within a vicinity of the prostate (e.g., within 1 mm, 5 mm, 10 mm, 1 cm, 2 cm, 5 cm, etc.)], but not conclusive evidence of lesions outside the primary tumor volume. For example, a PET image may not show any hotspots outside of a primary tumor region. In certain embodiments, a medical image may contain image features outside a primary tumor region, but these features may not meet criteria for concluding that they represent metastases outside a primary tumor region. For example, hotspots may appear in a PET image outside a primary tumor volume but may not be of sufficient size and/or intensity to be characterized conclusively as metastatic lesions. In certain embodiments, other criteria may be used. For example, in certain embodiments, hotspots outside of a primary tumor region may be evaluated by a machine learning model and assigned a likelihood score representing a likelihood (e.g., as determined by the machine learning model) that they are a metastatic lesion.

In certain embodiments, a medical image may be indicative of localized disease based on an evaluation of a medical professional, such as a physician, radiologist, etc. Such medical images may be included in and/or associated with a signed report by a particular medical professional that comprises a conclusion of localized disease.

In certain embodiments, systems and methods of the present disclosure may receive, as input, medical images indicative of localized disease and determine a metastases score as described herein. A metastases score may be indicative of presence of metastases, which may be indicative of presence of, for example, occult metastases or synchronous metastases that were not present in the medical image or missed by a diagnosing practitioner. A metastases score may be indicative that a patient will develop metachronous metastases, e.g., following treatment.

In certain embodiments, machine learning models may be trained to evaluate presence of synchronous metastases and then used to generate, at inference, predictions of whether patients presenting with localized disease will develop metastases, for example, at future times such as following treatment. For example, as demonstrated in Example 3, this approach provides accurate predictions. Without wishing to be bound to any particular theory this approach is believed to be justified by the premise that most early metastatic progression events occur consequent to growth of co-existing occult metastases at the time of curative intent therapy. Among other things, this approach allows for training strategies to benefit from potentially larger amounts of data, since it makes use of images obtained at a single time point. Otherwise, training examples corresponding exactly to the desired scenario—patients presenting initially with localized disease and then developing or not developing metastases later on, following treatment, would require imaging patients at an initial visit and then waiting, potentially several years, for them to undergo therapy and subsequent follow up imaging and diagnosis in order to label images from the initial visit as positive (e.g., the patient developed metastases later on) or negative (e.g., the patient did not develop metastases later on) examples.

Accordingly, in certain embodiments, a machine learning model may be trained using a dataset comprising a plurality of example images, including images of purely localized disease (localized disease example) and images showing synchronous metastases (synchronous metastases examples). While the full training example images may show synchronous metastases or not (allowing them to be immediately labeled as positive or negative examples), the machine learning model may be trained on input corresponding a primary tumor region only, thereby causing the model to learn to classify patients as positive or negative for synchronous metastases based on image data within the primary tumor region alone. Following training, the (e.g., trained machine learning) model may be provided images of patients obtained at, for example, an initial (e.g., pre-treatment) visit. For images that are indicative of localized disease, as determined via another computational approach and/or by evaluation by a medical professional, the machine learning model may generate a metastases score, as it did during training. Although during training, parameters of the machine learning model may have been refined to allow for accurate prediction of synchronous metastases, values generated during inference may be used as a risk/likelihood that a patient initially presenting only with localized disease will, at a later date, present metastases (e.g., metachronous metastases).

F. GUIDANCE FOR PATIENT DIAGNOSIS AND TREATMENT

Turning again to FIG. 4A, metastases predictions of the present disclosure may, for example, be used to provide guidance for patient diagnosis and treatment decisions, for example being displayed and/or provided as part of a decision support system 410.

The approaches described herein may be used, for example, in an initial visit, prior to therapy. Therapy and/or treatment approaches may be determined based on predictions, for example more aggressive therapy. For example, a patient may present with localized disease based on evaluation of medical images obtained at an initial staging or pre-treatment visit. These initial medical images may be analyzed by approaches described herein to produce metastases scores reflecting a risk/likelihood that the patient is prone to or will eventually develop metastases, e.g., at a later time. If metastases score is high, e.g., reflecting a high likelihood of metastases, for example, a more aggressive treatment approach may be determined to be prudent and selected, e.g., to compensate for/overcome this risk.

G. COMPUTER SYSTEM AND NETWORK ARCHITECTURE

Certain embodiments described herein make use of computer algorithms in the form of software instructions executed by a computer processor. In certain embodiments, the software instructions include a machine learning module, also referred to herein as artificial intelligence software. As used herein, a machine learning module refers to a computer implemented process (e.g., a software function) that implements one or more specific machine learning techniques, e.g., artificial neural networks (ANNs), e.g., convolutional neural networks (CNNs), e.g., recursive neural networks, e.g., recurrent neural networks such as long short-term memory (LSTM) or Bilateral long short-term memory (Bi-LSTM), random forest, decision trees, support vector machines, and the like, in order to determine, for a given input, one or more output values.

In certain embodiments, machine learning modules implementing machine learning techniques are trained, for example using datasets that include categories of data described herein (e.g., CT images, MRI images, PET images, SPECT images). Such training may be used to determine various parameters of machine learning algorithms implemented by a machine learning module, such as weights associated with layers in neural networks. In certain embodiments, once a machine learning module is trained, e.g., to accomplish a specific task such as segmenting anatomical regions, segmenting and/or classifying hotspots, or determining values for prognostic, treatment response, and/or predictive metrics, values of determined parameters are fixed and the (e.g., unchanging, static) machine learning module is used to process new data (e.g., different from the training data) and accomplish its trained task without further updates to its parameters (e.g., the machine learning module does not receive feedback and/or updates). In certain embodiments, machine learning modules may receive feedback, e.g., based on user review of accuracy, and such feedback may be used as additional training data, to dynamically update the machine learning module. In certain embodiments, two or more machine learning modules may be combined and implemented as a single module and/or a single software application. In certain embodiments, two or more machine learning modules may also be implemented separately, e.g., as separate software applications. A machine learning module may be software and/or hardware. For example, a machine learning module may be implemented entirely as software, or certain functions of an ANN module may be carried out via specialized hardware (e.g., via an application specific integrated circuit (ASIC)).

Figure 5:
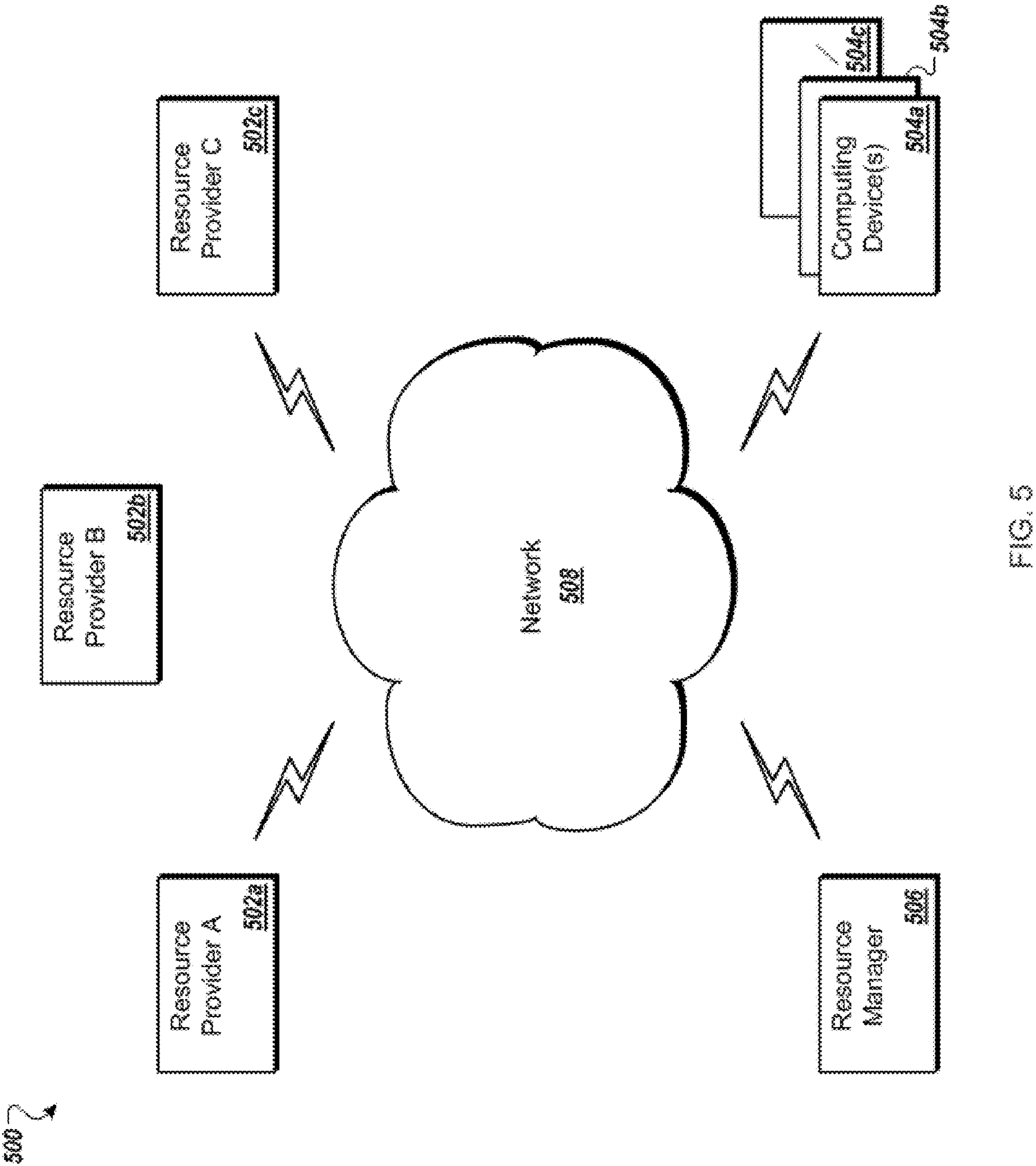
FIG. 5 is a block diagram of an exemplary cloud computing environment, used in certain embodiments.

Turning to FIG. 5, an implementation of a network environment 500 for use in providing systems, methods, and architectures as described herein is shown and described. In brief overview, referring now to FIG. 5, a block diagram of an exemplary cloud computing environment 500 is shown and described. The cloud computing environment 500 may include one or more resource providers 502*a*, 502*b*, 502*c* (collectively, 502). Each resource provider 502 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 502 may be connected to any other resource provider 502 in the cloud computing environment 500. In some implementations, the resource providers 502 may be connected over a computer network 508. Each resource provider 502 may be connected to one or more computing device 504*a*, 504*b*, 504*c* (collectively, 504), over the computer network 508.

The cloud computing environment 500 may include a resource manager 506. The resource manager 506 may be connected to the resource providers 502 and the computing devices 504 over the computer network 508. In some implementations, the resource manager 506 may facilitate the provision of computing resources by one or more resource providers 502 to one or more computing devices 504. The resource manager 506 may receive a request for a computing resource from a particular computing device 504. The resource manager 506 may identify one or more resource providers 502 capable of providing the computing resource requested by the computing device 504. The resource manager 506 may select a resource provider 502 to provide the computing resource. The resource manager 506 may facilitate a connection between the resource provider 502 and a particular computing device 504. In some implementations, the resource manager 506 may establish a connection between a particular resource provider 502 and a particular computing device 504. In some implementations, the resource manager 506 may redirect a particular computing device 504 to a particular resource provider 502 with the requested computing resource.

Figure 6:
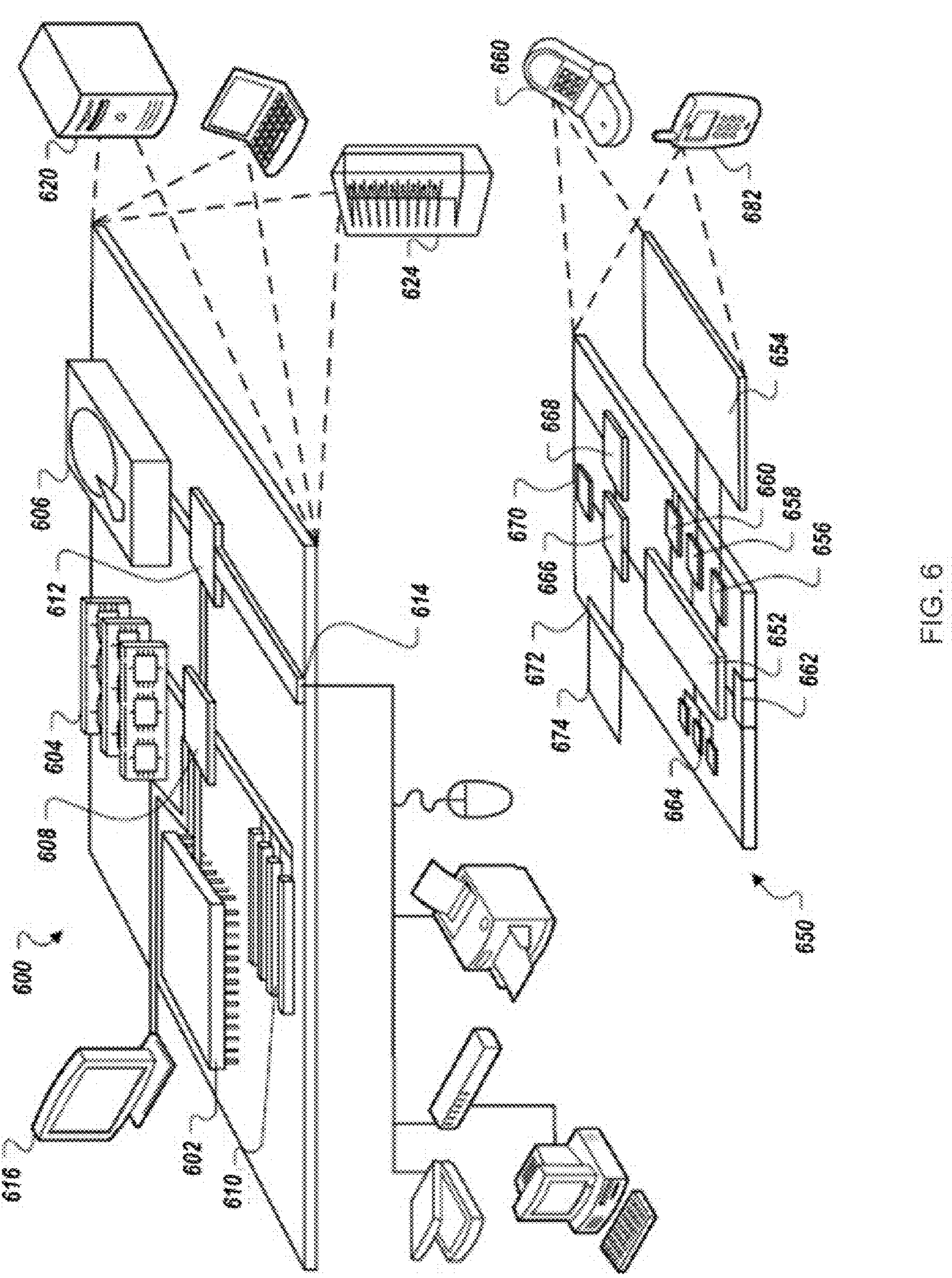
FIG. 6 is a block diagram of an example computing device and an example mobile computing device, used in certain embodiments.

FIG. 6 shows an example of a computing device 600 and a mobile computing device 650 that can be used to implement the techniques described in this disclosure. The computing device 600 is intended to represent various forms of digital computers, such as laptops, desktops, workstations, personal digital assistants, servers, blade servers, mainframes, and other appropriate computers. The mobile computing device 650 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 600 includes a processor 602, a memory 604, a storage device 606, a high-speed interface 608 connecting to the memory 604 and multiple high-speed expansion ports 610, and a low-speed interface 612 connecting to a low-speed expansion port 614 and the storage device 606. Each of the processor 602, the memory 604, the storage device 606, the high-speed interface 608, the high-speed expansion ports 610, and the low-speed interface 612, are interconnected using various busses, and may be mounted on a common motherboard or in other manners as appropriate. The processor 602 can process instructions for execution within the computing device 600, including instructions stored in the memory 604 or on the storage device 606 to display graphical information for a GUI on an external input/output device, such as a display 616 coupled to the high-speed interface 608. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 604 stores information within the computing device 600. In some implementations, the memory 604 is a volatile memory unit or units. In some implementations, the memory 604 is a non-volatile memory unit or units. The memory 604 may also be another form of computer-readable medium, such as a magnetic or optical disk.

The storage device 606 is capable of providing mass storage for the computing device 600. In some implementations, the storage device 606 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 602), perform one or more methods, such as those described above. The instructions can also be stored by one or more storage devices such as computer- or machine-readable mediums (for example, the memory 604, the storage device 606, or memory on the processor 602).

The high-speed interface 608 manages bandwidth-intensive operations for the computing device 600, while the low-speed interface 612 manages lower bandwidth-intensive operations. Such allocation of functions is an example only. In some implementations, the high-speed interface 608 is coupled to the memory 604, the display 616 (e.g., through a graphics processor or accelerator), and to the high-speed expansion ports 610, which may accept various expansion cards (not shown). In the implementation, the low-speed interface 612 is coupled to the storage device 606 and the low-speed expansion port 614. The low-speed expansion port 614, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 620, or multiple times in a group of such servers. In addition, it may be implemented in a personal computer such as a laptop computer 622. It may also be implemented as part of a rack server system 624. Alternatively, components from the computing device 600 may be combined with other components in a mobile device (not shown), such as a mobile computing device 650. Each of such devices may contain one or more of the computing device 600 and the mobile computing device 650, and an entire system may be made up of multiple computing devices communicating with each other.

The mobile computing device 650 includes a processor 652, a memory 664, an input/output device such as a display 654, a communication interface 666, and a transceiver 668, among other components. The mobile computing device 650 may also be provided with a storage device, such as a micro-drive or other device, to provide additional storage. Each of the processor 652, the memory 664, the display 654, the communication interface 666, and the transceiver 668, are interconnected using various buses, and several of the components may be mounted on a common motherboard or in other manners as appropriate.

The processor 652 can execute instructions within the mobile computing device 650, including instructions stored in the memory 664. The processor 652 may be implemented as a chipset of chips that include separate and multiple analog and digital processors. The processor 652 may provide, for example, for coordination of the other components of the mobile computing device 650, such as control of user interfaces, applications run by the mobile computing device 650, and wireless communication by the mobile computing device 650.

The processor 652 may communicate with a user through a control interface 658 and a display interface 656 coupled to the display 654. The display 654 may be, for example, a TFT (Thin-Film-Transistor Liquid Crystal Display) display or an OLED (Organic Light Emitting Diode) display, or other appropriate display technology. The display interface 656 may comprise appropriate circuitry for driving the display 654 to present graphical and other information to a user. The control interface 658 may receive commands from a user and convert them for submission to the processor 652. In addition, an external interface 662 may provide communication with the processor 652, so as to enable near area communication of the mobile computing device 650 with other devices. The external interface 662 may provide, for example, for wired communication in some implementations, or for wireless communication in other implementations, and multiple interfaces may also be used.

The memory 664 stores information within the mobile computing device 650. The memory 664 can be implemented as one or more of a computer-readable medium or media, a volatile memory unit or units, or a non-volatile memory unit or units. An expansion memory 674 may also be provided and connected to the mobile computing device 650 through an expansion interface 672, which may include, for example, a SIMM (Single In Line Memory Module) card interface. The expansion memory 674 may provide extra storage space for the mobile computing device 650, or may also store applications or other information for the mobile computing device 650. Specifically, the expansion memory 674 may include instructions to carry out or supplement the processes described above, and may include secure information also. Thus, for example, the expansion memory 674 may be provide as a security module for the mobile computing device 650, and may be programmed with instructions that permit secure use of the mobile computing device 650. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 652), perform one or more methods, such as those described above. The instructions can also be stored by one or more storage devices, such as one or more computer- or machine-readable mediums (for example, the memory 664, the expansion memory 674, or memory on the processor 652). In some implementations, the instructions can be received in a propagated signal, for example, over the transceiver 668 or the external interface 662.

The mobile computing device 650 may communicate wirelessly through the communication interface 666, which may include digital signal processing circuitry where necessary. The communication interface 666 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 668 using a radio-frequency. In addition, short-range communication may occur, such as using a Bluetooth®, Wi-Fi™, or other such transceiver (not shown). In addition, a GPS (Global Positioning System) receiver module 670 may provide additional navigation- and location-related wireless data to the mobile computing device 650, which may be used as appropriate by applications running on the mobile computing device 650.

The mobile computing device 650 may also communicate audibly using an audio codec 660, which may receive spoken information from a user and convert it to usable digital information. The audio codec 660 may likewise generate audible sound for a user, such as through a speaker, e.g., in a handset of the mobile computing device 650. Such sound may include sound from voice telephone calls, may include recorded sound (e.g., voice messages, music files, etc.) and may also include sound generated by applications operating on the mobile computing device 650.

The mobile computing device 650 may be implemented in a number of different forms, as shown in the figure. For example, it may be implemented as a cellular telephone 680. It may also be implemented as part of a smart-phone 682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Actions associated with implementing the systems may be performed by one or more programmable processors executing one or more computer programs. All or part of the systems may be implemented as special purpose logic circuitry, for example, a field programmable gate array (FPGA) or an application-specific integrated circuit (ASIC), or both. All or part of the systems may also be implemented as special purpose logic circuitry, for example, a specially designed (or configured) central processing unit (CPU), conventional central processing units (CPU) a graphics processing unit (GPU), and/or a tensor processing unit (TPU).

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, modules described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

H. IMAGING AGENTS

As described herein, a variety of radionuclide labelled PSMA binding agents may be used as radiopharmaceutical imaging agents for nuclear medicine imaging to detect and evaluate prostate cancer. In certain embodiments, certain radionuclide labelled PSMA binding agents are appropriate for PET imaging, while others are suited for SPECT imaging.

H.i. PET Imaging Radionuclide Labelled PSMA Binding Agents

In certain embodiments, a radionuclide labelled PSMA binding agent is a radionuclide labelled PSMA binding agent appropriate for PET imaging.

In certain embodiments, a radionuclide labelled PSMA binding agent comprises [18F]DCFPyL (also referred to as PyL™; also referred to as DCFPyL-18F):

[18F]DCFPyL

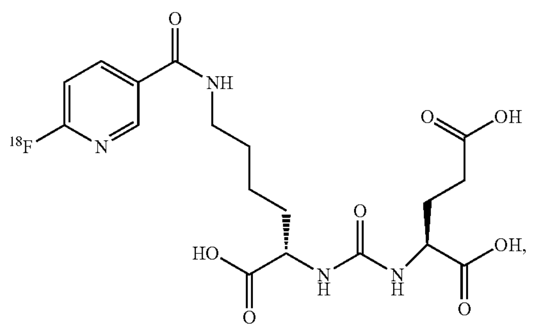

or a pharmaceutically acceptable salt thereof.

In certain embodiments, a radionuclide labelled PSMA binding agent comprises [18F]DCFBC:

[18F]DCFBC

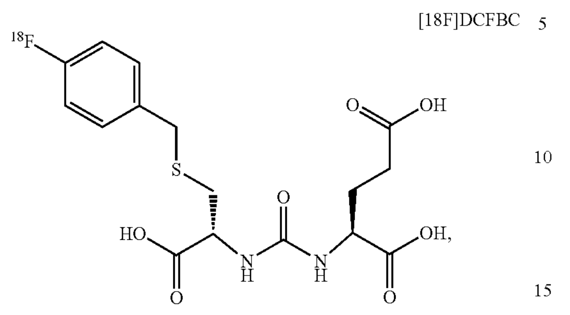

or a pharmaceutically acceptable salt thereof.

In certain embodiments, a radionuclide labelled PSMA binding agent comprises $^{68}$Ga-PSMA-HBED-CC (also referred to as $^{68}$Ga-PSMA-11):

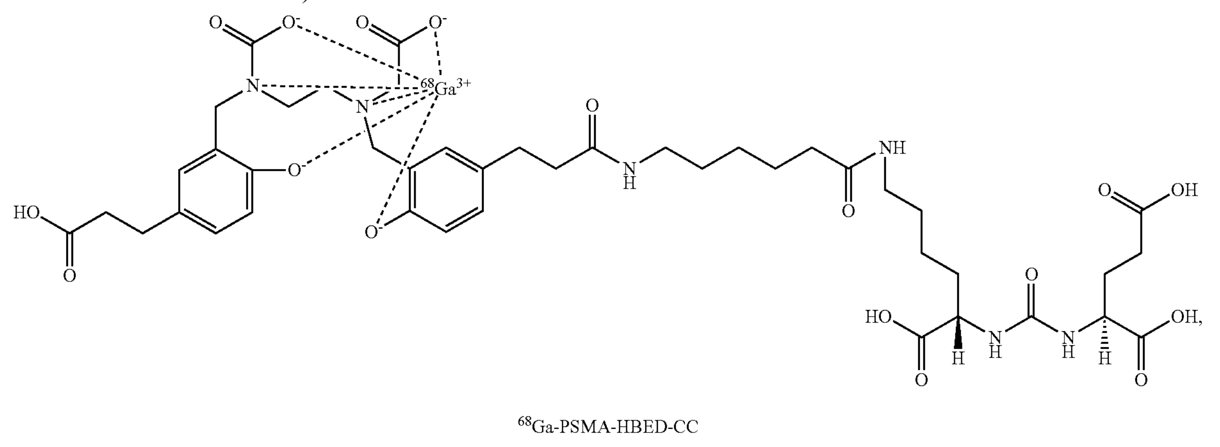

$^{68}$Ga-PSMA-HBED-CC or a pharmaceutically acceptable salt thereof.

In certain embodiments, a radionuclide labelled PSMA binding agent comprises PSMA-617:

PSMA-617

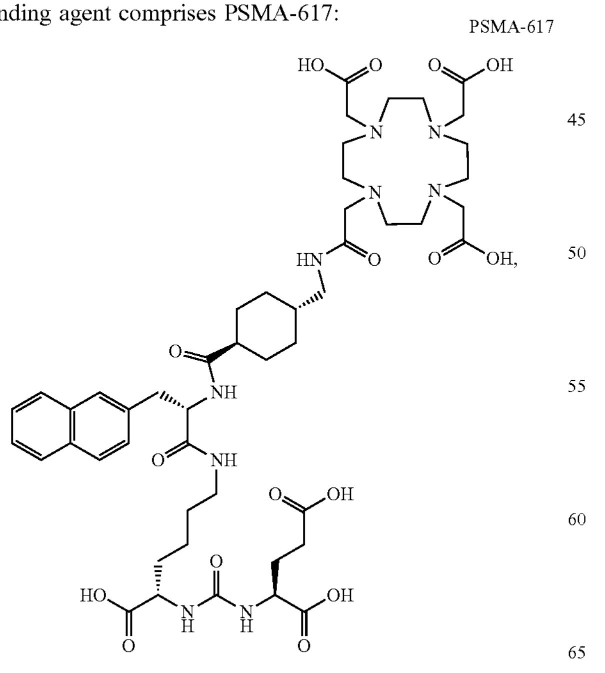

or a pharmaceutically acceptable salt thereof. In certain embodiments, the radionuclide labelled PSMA binding agent comprises $^{68}$Ga-PSMA-617, which is PSMA-617 labelled with $^{68}$Ga, or a pharmaceutically acceptable salt thereof. In certain embodiments, a radionuclide labelled PSMA binding agent comprises $^{177}$Lu-PSMA-617, which is PSMA-617 labelled with $^{177}$Lu, or a pharmaceutically acceptable salt thereof.

In certain embodiments, a radionuclide labelled PSMA binding agent comprises PSMA-I&T:

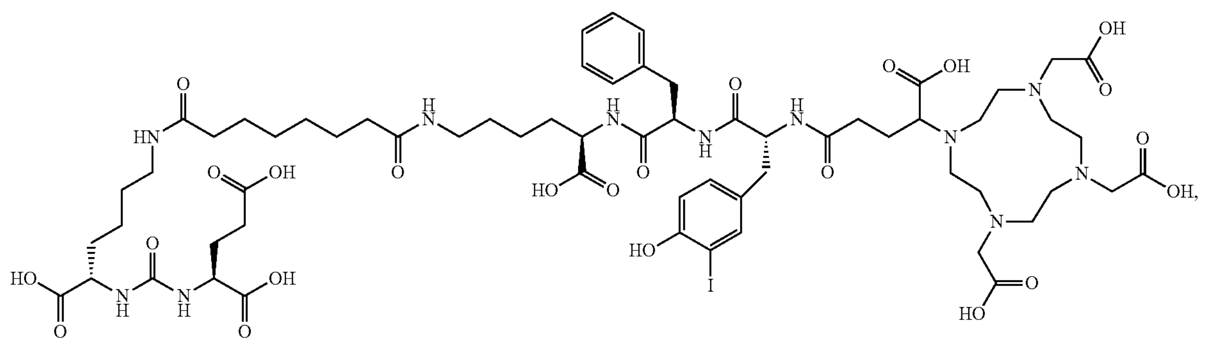

PSMA-I&T or a pharmaceutically acceptable salt thereof. In certain embodiments, a radionuclide labelled PSMA binding agent comprises $^{68}$Ga-PSMA-I&T, which is PSMA-I&T labelled with $^{68}$Ga, or a pharmaceutically acceptable salt thereof.

In certain embodiments, a radionuclide labelled PSMA binding agent comprises PSMA-1007:

PSMA-1007

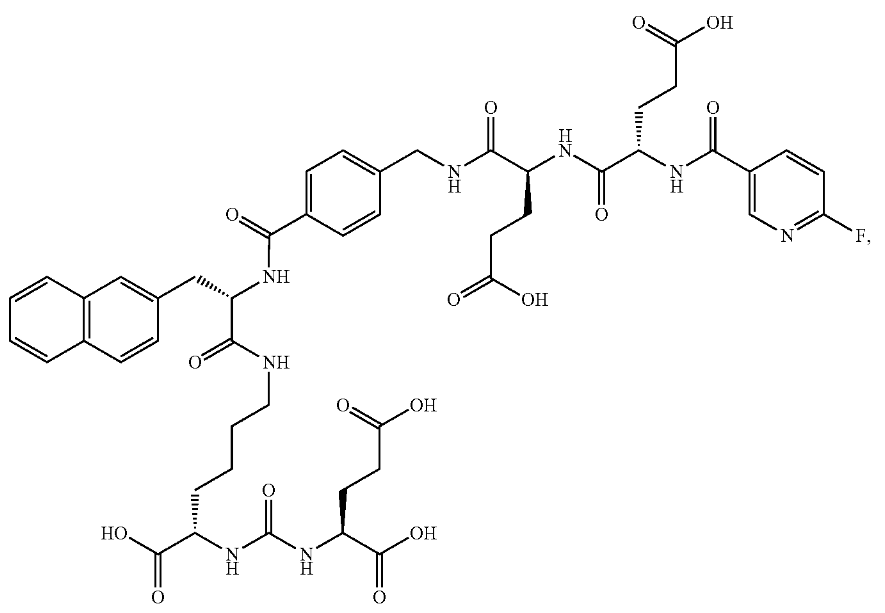

or a pharmaceutically acceptable salt thereof. In certain embodiments, a radionuclide labelled PSMA binding agent comprises 18F-PSMA-1007, which is PSMA-1007 labelled with 18F, or a pharmaceutically acceptable salt thereof.

In certain embodiments, a radionuclide labeled PSMA binding agent comprises 18F-JK-PSMA-7:

18F-JK-PSMA-7

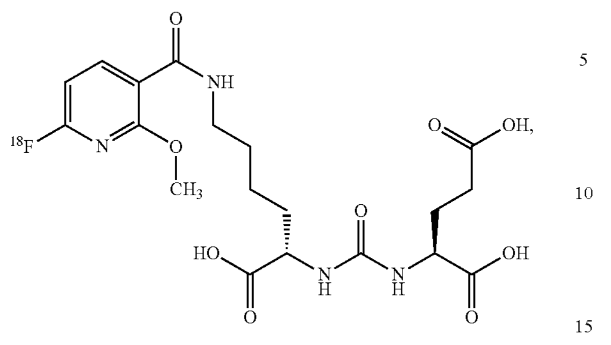

or a pharmaceutically acceptable salt thereof.

In certain embodiments, a radionuclide labeled PSMA binding agent comprises (18F) rhPSMA-7.3 (e.g., POSLUMA®, also described at https://www.posluma.com/prescribing-information.pdf):

(18F) rhPSMA-7.3

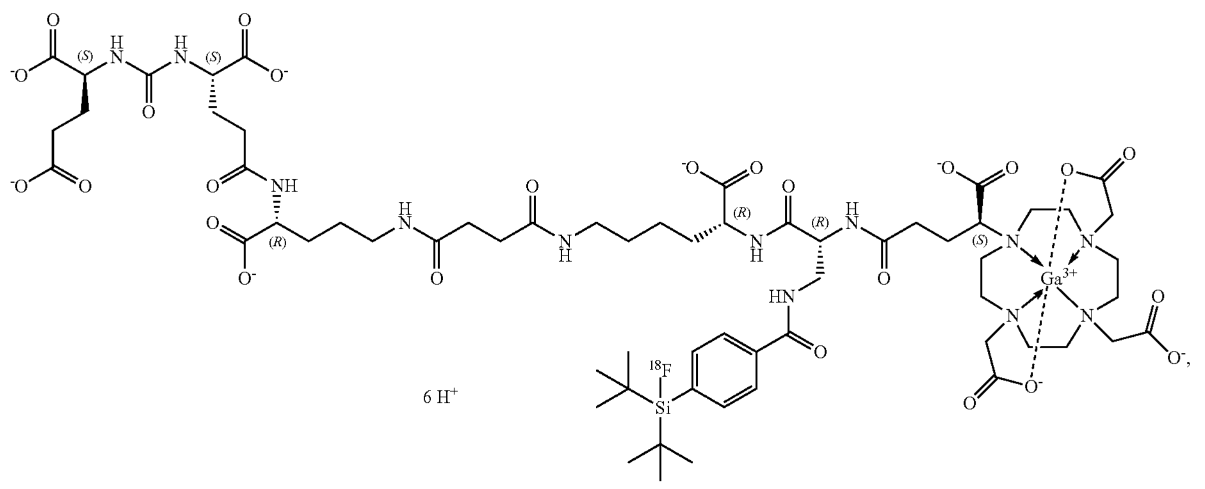

or a pharmaceutically acceptable salt thereof.

H.ii. SPECT Imaging Radionuclide Labelled PSMA Binding Agents

In certain embodiments, a radionuclide labelled PSMA binding agent is a radionuclide labelled PSMA binding agent appropriate for SPECT imaging.

In certain embodiments, a radionuclide labelled PSMA binding agent comprises 1404 (also referred to as MIP-1404):

1404

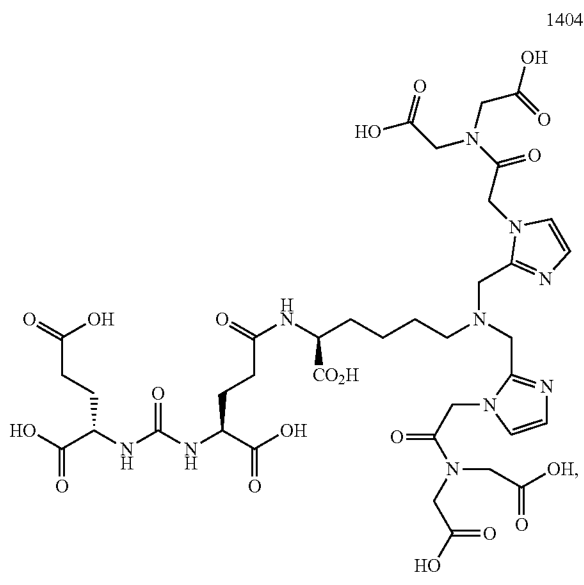 [SMILES: O=C(O)CC[C@H](NC(=O)N[C@@H](CCC(=O)N[C@@H](CCCCN(Cc1nccn1CC(=O)N(CC(=O)O)CC(=O)O)Cc1nccn1CC(=O)N(CC(=O)O)CC(=O)O)C(=O)O)C(=O)O)C(=O)O]

or a pharmaceutically acceptable salt thereof.

In certain embodiments, a radionuclide labelled PSMA binding agent comprises 1405 (also referred to as MIP-1405):

1405

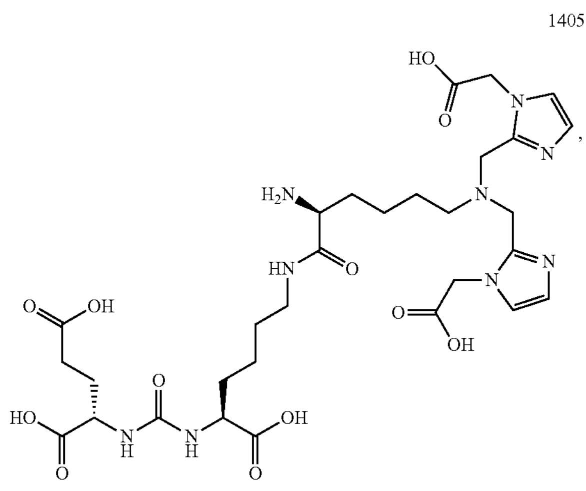 [SMILES: N[C@@H](CCCCN(Cc1nccn1CC(=O)O)Cc1nccn1CC(=O)O)C(=O)NCCCC[C@H](NC(=O)N[C@@H](CCC(=O)O)C(=O)O)C(=O)O]

or a pharmaceutically acceptable salt thereof.

In certain embodiments, a radionuclide labelled PSMA binding agent comprises 1427 (also referred to as MIP-1427):

1427

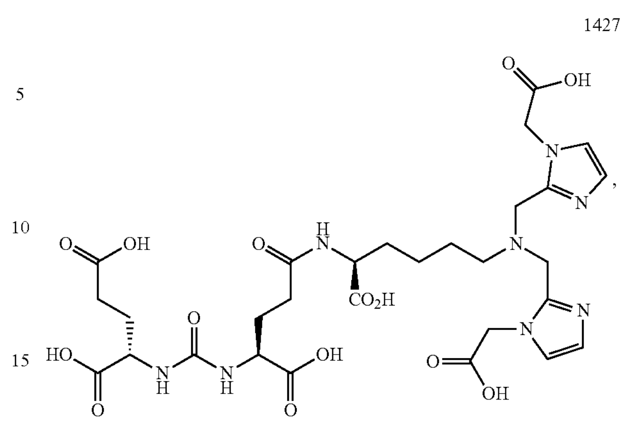

or a pharmaceutically acceptable salt thereof.

In certain embodiments, a radionuclide labelled PSMA binding agent comprises 1428 (also referred to as MIP-1428):

1428

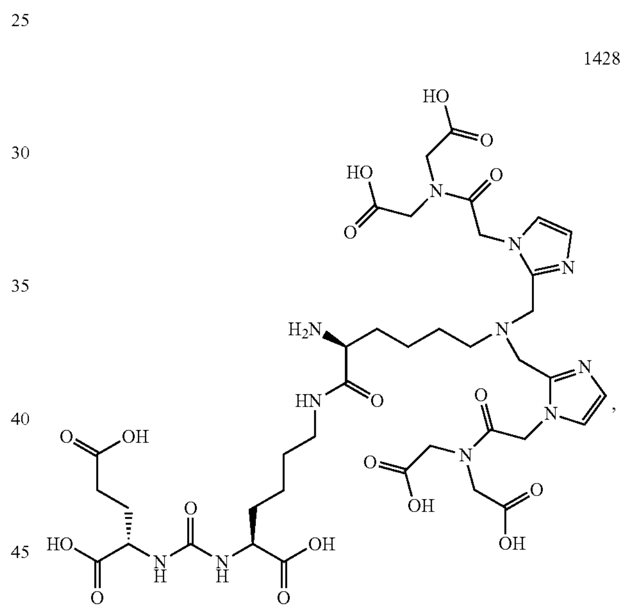

or a pharmaceutically acceptable salt thereof.

In certain embodiments, a PSMA binding agent is labelled with a radionuclide by chelating it to a radioisotope of a metal [e.g., a radioisotope of technetium (Tc) (e.g., technetium-99m (99mTc)); e.g., a radioisotope of rhenium (Re) (e.g., rhenium-188 (188Re); e.g., rhenium-186 (186Re)); e.g., a radioisotope of yttrium (Y) (e.g., 90Y); e.g., a radioisotope of lutetium (Lu)(e.g., 177Lu); e.g., a radioisotope of gallium (Ga) (e.g., 68Ga; e.g., 67Ga); e.g., a radioisotope of indium (e.g., 111In); e.g., a radioisotope of copper (Cu) (e.g., 67Cu)].

In certain embodiments, 1404 is labelled with a radionuclide (e.g., chelated to a radioisotope of a metal). In certain embodiments, a radionuclide labelled PSMA binding agent comprises $^{99m}$Tc-MIP-1404, which is 1404 labelled with (e.g., chelated to)$^{99m}$Tc:

$^{99m}$Tc-MIP-1404

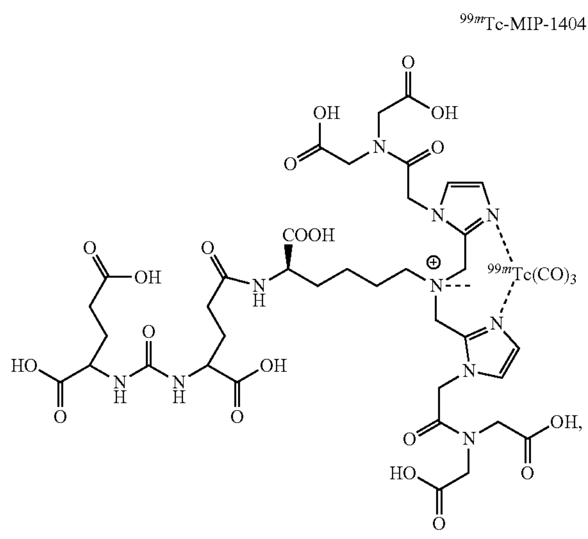

or a pharmaceutically acceptable salt thereof. In certain embodiments, 1404 may be chelated to other metal radioisotopes [e.g., a radioisotope of rhenium (Re) (e.g., rhenium-188 ($^{188}$Re); e.g., rhenium-186 (186Re)); e.g., a radioisotope of yttrium (Y) (e.g., 90Y); e.g., a radioisotope of lutetium (Lu)(e.g., 177Lu); e.g., a radioisotope of gallium (Ga) (e.g., 68Ga; e.g., 67Ga); e.g., a radioisotope of indium (e.g., 111In); e.g., a radioisotope of copper (Cu) (e.g., 67Cu)] to form a compound having a structure similar to the structure shown above for 99mTc-MIP-1404, with the other metal radioisotope substituted for 99mTc.

In certain embodiments, 1405 is labelled with a radionuclide (e.g., chelated to a radioisotope of a metal). In certain embodiments, a radionuclide labelled PSMA binding agent comprises $^{99m}$Tc-MIP-1405, which is 1405 labelled with (e.g., chelated to)$^{99m}$Tc:

$^{99m}$Tc-MIP-1405

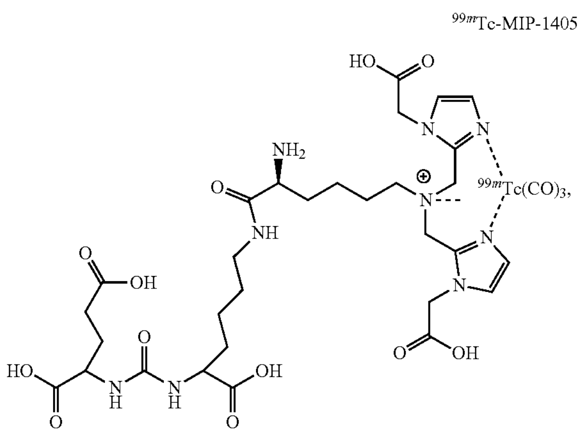

or a pharmaceutically acceptable salt thereof. In certain embodiments, 1405 may be chelated to other metal radioisotopes [e.g., a radioisotope of rhenium (Re) (e.g., rhenium-188 ($^{188}$Re); e.g., rhenium-186 ($^{186}$Re)); e.g., a radioisotope of yttrium (Y) (e.g., $^{90}$Y); e.g., a radioisotope of lutetium (Lu)(e.g., 177Lu); e.g., a radioisotope of gallium (Ga) (e.g., 68Ga; e.g., 67Ga); e.g., a radioisotope of indium (e.g., 111In); e.g., a radioisotope of copper (Cu) (e.g., 67Cu)] to form a compound having a structure similar to the structure shown above for 99mTc-MIP-1405, with the other metal radioisotope substituted for 99mTc.

In certain embodiments, 1427 is labelled with (e.g., chelated to) a radioisotope of a metal, to form a compound according to the formula below:

1427

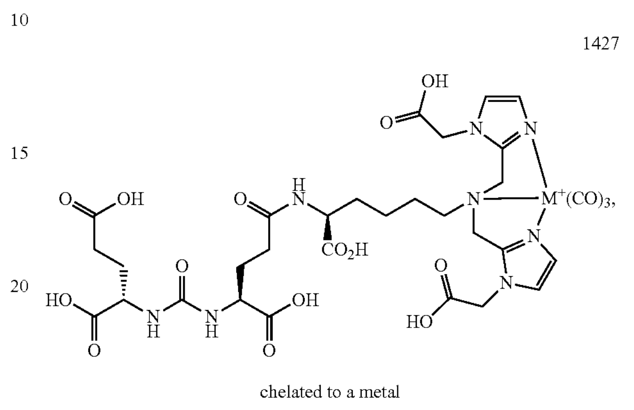

chelated to a metal or a pharmaceutically acceptable salt thereof, wherein M is a metal radioisotope [e.g., a radioisotope of technetium (Tc) (e.g., technetium-99m ($^{99m}$Tc)); e.g., a radioisotope of rhenium (Re) (e.g., rhenium-188 (188Re); e.g., rhenium-186 (186Re)); e.g., a radioisotope of yttrium (Y) (e.g., 90Y); e.g., a radioisotope of lutetium (Lu)(e.g., 177Lu); e.g., a radioisotope of gallium (Ga) (e.g., 68Ga; e.g., 67Ga); e.g., a radioisotope of indium (e.g., 111In); e.g., a radioisotope of copper (Cu) (e.g., 67Cu)] with which 1427 is labelled.

In certain embodiments, 1428 is labelled with (e.g., chelated to) a radioisotope of a metal, to form a compound according to the formula below:

1428

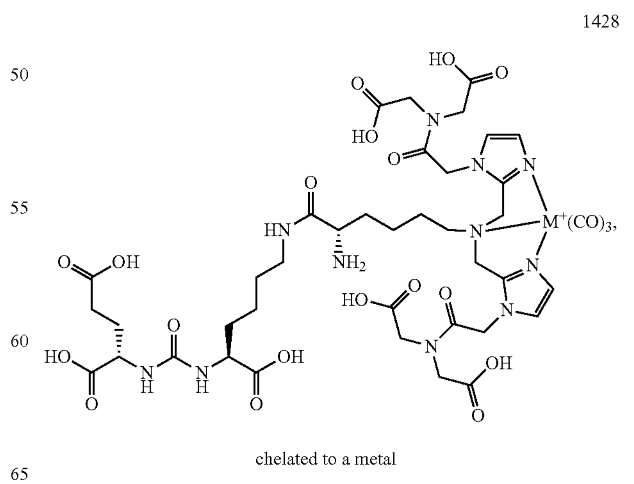

chelated to a metal or a pharmaceutically acceptable salt thereof, wherein M is a metal radioisotope [e.g., a radioisotope of technetium (Tc) (e.g., technetium-99m ($^{99m}$Tc)); e.g., a radioisotope of rhenium (Re) (e.g., rhenium-188 (188Re); e.g., rhenium-186 (186Re)); e.g., a radioisotope of yttrium (Y) (e.g., 90Y); e.g., a radioisotope of lutetium (Lu)(e.g., 177Lu); e.g., a radioisotope of gallium (Ga) (e.g., 68Ga; e.g., 67Ga); e.g., a radioisotope of indium (e.g., 111In); e.g., a radioisotope of copper (Cu) (e.g., 67Cu)] with which 1428 is labelled.

In certain embodiments, a radionuclide labelled PSMA binding agent comprises PSMA I&S:

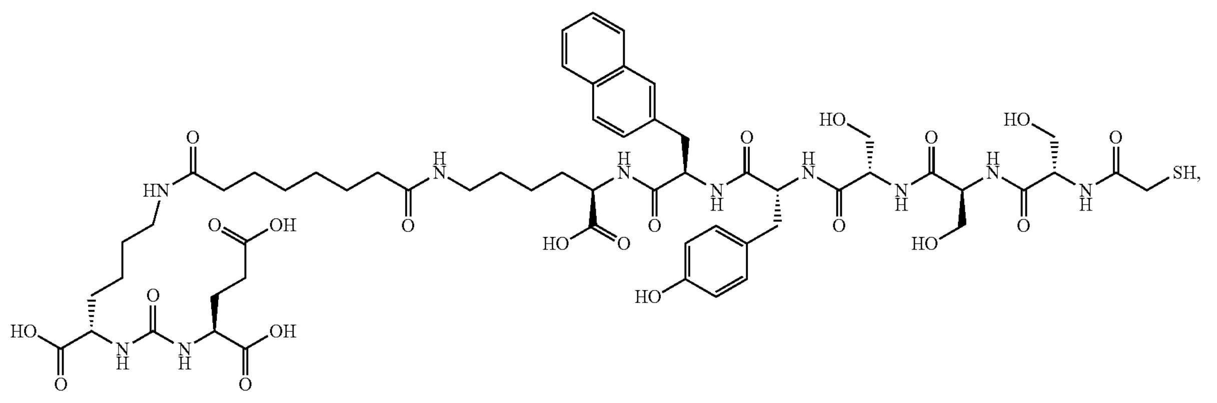

PSMA I&S or a pharmaceutically acceptable salt thereof. In certain embodiments, a radionuclide labelled PSMA binding agent comprises 99mTc-PSMA I&S, which is PSMA I&S labelled with 99mTc, or a pharmaceutically acceptable salt thereof.

I. EXAMPLES

I.i Example 1: Predicting Synchronous Metastases Using a Convolutional Neural Network Model and Intraprostatic [F18]DCFPyL PSMA Imaging This example provides results of an imaging study that demonstrates use of a CNN model in conjunction with intraprostatic PSMA imaging. In particular, [F18]DCFPyL (PyL™) is a PSMA targeted imaging agent that provides whole-body staging of prostate cancer. This example demonstrates how image analysis of a primary tumor using machine learning techniques (e.g., deep learning algorithms) can offer additional insight into disease biology, including the presence of co-existing metastatic disease. Approaches using convolutional neural network (CNN) models using inputs from whole prostate PyL™ images along with auto-segmented hotspots within a prostate are used to predict presence or absence of synchronous metastases and are compared against established models built from clinicopathologic information.

Ninety-two (92) U.S. Veterans with de novo prostate cancer were imaged with PyL PSMA PET/CT for initial staging (46% with metastatic disease). PyL images of the prostate were analyzed using aPROMISE, which automatically segments, localizes, and quantifies disease via analysis PSMA PET images. Segmentations of the prostate were used to map the PyL PET image of the prostate. Both an entire prostate as well as aPROMISE-determined hotspots were used as inputs for the CNN model of this example, where, according to attention map analysis, the hotspot information helps the network understand the location and extent of tumors.

Image analysis machine learning model used in this example was made up of a Conv3D layer of 4 kernels, a Conv3D layer of 8 kernels, a dense layer of 64 nodes, followed by a final dense layer with 2 nodes. Model training was performed on images using 5-fold cross validation with non-overlapping validation sets. Area under ROC curve (AUC) was computed to assess performance of the model in predicting the presence of metastases and these test predictions were compared with ground truth (M1). Prediction scores from UCSF-CAPRA and UCLA PSMA risk calculator were used to comparators, e.g., for comparing CNN model performance against models built from clinicopathologic information.

The best CNN model that operated on prostatic PyL images alone achieved an AUC of 0.800 for prediction of metastatic disease. For comparison, the UCSF-CAPRA score and UCLA-PSMA risk calculator (any upstaging on PET), which rely on clinicopathologic information, had AUCs of 0.729 and 0.754 in this dataset, respectively.

Accordingly, a CNN based model using PyL imaging predicted synchronous metastases (mets) from intraprostatic PyL uptake patterns alone with an accuracy in this dataset that is at least comparable to published models based on clinicopathologic features (non-imaging). These results support the use of PyL CNN-based models to prognosticate metastatic progression.

Figure 7A:
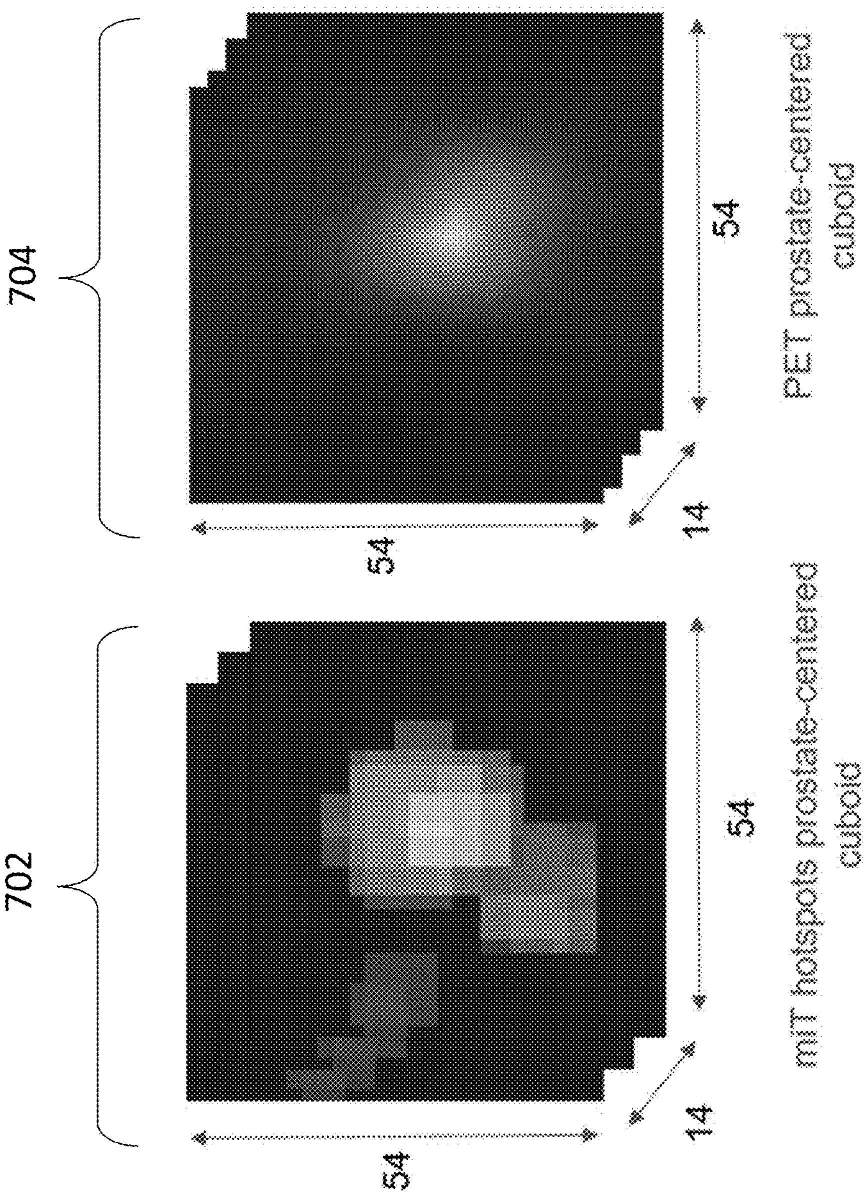
FIG. 7A is a set of illustrative images showing input channels for a two-channel neural network model, according to an illustrative embodiment.

FIG. 7A illustrates imaging channel inputs used by the CNN model of the present example. As shown in FIG. 7A, the CNN model received two channels of input extracted from PSMA PET/CT images. A first, hotspot, channel 702 was a 54×14×54 cuboid volume centered on a detected prostate volume and comprising miT hotspots detected by the aPROMISE technique. A second, prostate intensity, channel 704 was a 54×14×54 cuboid region extracted from the PET image and centered on the prostate. Accordingly, the two channel input received by the CNN model was a 2×54×14×54 matrix. The CNN model was trained using a dataset with both positive and negative examples—i.e., images where patients were determined/known to be either positive or negative for synchronous metastases, as shown in Table 2A, below.

TABLE 2A

| Positive-negative sampling ratio. | | | |
|---|---|---|---|
| | Positive | Negative | Total |
| # | 62 | 48 | 110 |

Training, validation, and test dataset splits used are shown in Table 2B, below.

TABLE 2B

| Training, validation, and test set split. | | | |
|---|---|---|---|
| | Train | Validation | Test |
| # | 52 | 17 | 22 |

Figure 7B:
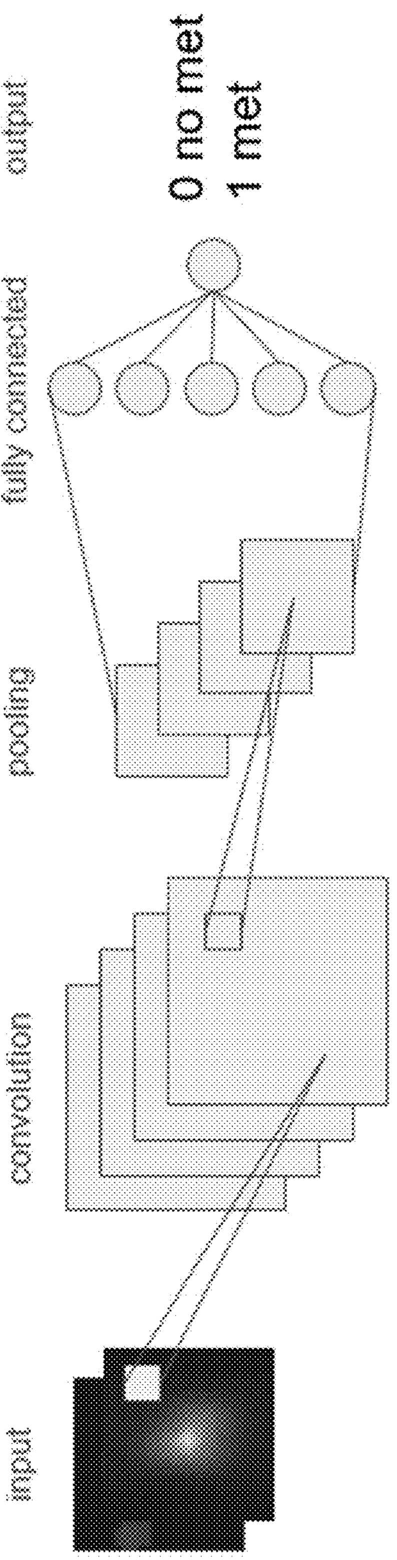
FIG. 7B is a diagram of an example CNN model architecture for performing binary classification, according to an illustrative embodiment.

FIG. 7B shows an example CNN architecture used for analyzing the 2-channel, 3D volume image inputs and performing a binary classification.

Fifty experiments were performed, and metrics such as accuracy (Acc.), AUC, f1 score, recall, and precission calculated for each. Table 2C, below, shows values of each of these metrics computed for the worst, best, and average experiment.

TABLE 2C

| Performance over 50 experiments. | | | | | |
|---|---|---|---|---|---|
| Worst | | Average | | Best | |
| Acc. | 0.25 | Acc. | 0.6552 | Acc. | 0.8636 |
| AUC | 0.6470 | AUC | 0.7008 | AUC | 0.7999 |
| f1 score | 0.0 | f1 score | 0.5777 | f1 score | 0.8571 |
| Recall | 0.0 | Recall | 0.5780 | Recall | 0.8999 |
| Precision | 0.0 | Precision | 0.6105 | Precision | 0.8181 |

The CNN model was also used to create combined models, that generated predictions using image input as well as certain pre-defined features, such as measured clinical variables and features computed from images. This approach, using a combination of data, was found to lead to the best performing model.

Figure 7C:
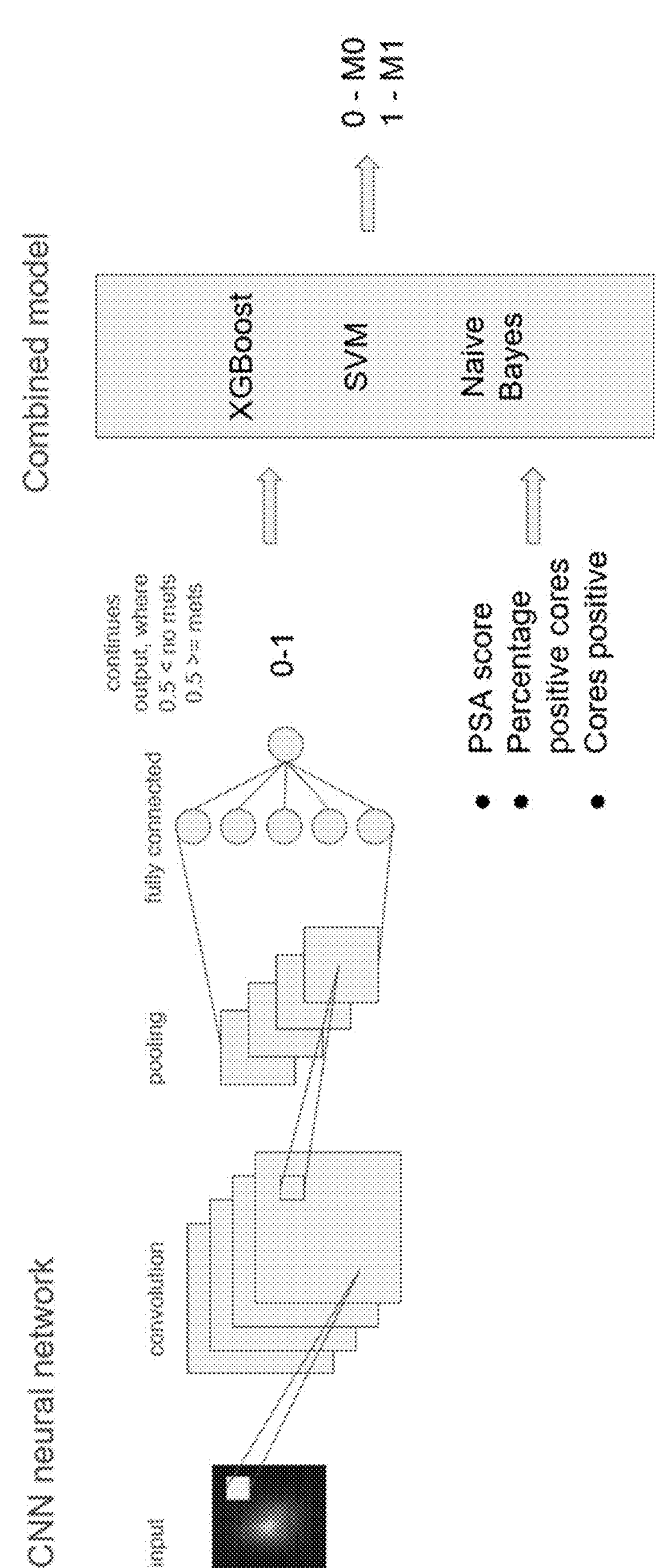
FIG. 7C is a diagram of an example fused model combining a CNN model with patient attributes, according to an illustrative embodiment.

FIG. 7C shows a schematic illustrating how a CNN model can be combined with other data inputs to create a combined model that generates predictions based on image data, as well as features such as clinical data measurements and features computed from images. As shown in FIG. 7C, a CNN neural network, e.g., as shown in FIG. 7B is used to analyze images and generate an output, such as a likelihood value or a binary classification. The CNN output is then fed, along with pre-defined features, into a secondary machine learning model, such as a decision tree model (e.g., a Gradient Boosting Decision Trees (GBDT) model, such as XGBoost), a support vector machine (SVM) model, or a naïve Bayes classifier. The secondary machine learning model then generates, as output, a final likelihood value and/or classification, reflecting whether a patient has synchronous metastases.

Tables 3A-3F, below, provide results for several machine learning models using combinations of CNN predictions and pre-defined features.

TABLE 3A

| Clinical variable measurement model results. Features: PSA, percent positive cores, cores positive | | | | | |
|---|---|---|---|---|---|
| SVM | | XGBoost | | Naïve Bayes | |
| Acc. | 0.6819 | Acc. | 0.6103 | Acc. | 0.6736 |
| AUC | 0.6640 | AUC | 0.6036 | AUC | 0.6184 |
| f1 score | 0.5962 | f1 score | 0.5478 | f1 score | 0.4665 |

TABLE 3B

| Combined clinical variable measurement and CNN image analysis output model results. Features: PSA, percent positive cores, cores positive + NN prediction | | | | | |
|---|---|---|---|---|---|
| SVM | | XGBoost | | Naïve Bayes | |
| Acc. | 0.6721 | Acc. | 0.6570 | Acc. | 0.7324 |
| AUC | 0.6618 | AUC | 0.6351 | AUC | 0.6886 |
| f1 score | 0.5904 | f1 score | 0.5792 | f1 score | 0.5996 |

TABLE 3C

| Combined clinical variable measurement and CNN image analysis output model results. Features: PSA, percent positive cores, cores positive + NN prediction | | | | | |
|---|---|---|---|---|---|
| SVM | | XGBoost | | Naïve Bayes | |
| Acc. | 0.6721 | Acc. | 0.6570 | Acc. | 0.7324 |
| AUC | 0.6618 | AUC | 0.6351 | AUC | 0.6886 |
| f1 score | 0.5904 | f1 score | 0.5792 | f1 score | 0.5996 |

TABLE 3D

| Measured and computed features model results. Features: PSA, pathologic grade, percent positive cores, cores positive, Primary Score, miTNM, PSMA expression score, uptake SUV peak value, uptake prostate zone, uptake type (focal vs. diffuse), uptake extends outside prostate, aorta SUV mean, liver SUV mean, overall upstaging risk, N upstaging, M upstaging | | | | | |
|---|---|---|---|---|---|
| SVM | | XGBoost | | Naïve Bayes | |
| Acc. | 0.0 | Acc. | 0.0 | Acc. | 0.6950 |
| AUC | 0.0 | AUC | 0.0 | AUC | 0.6912 |
| f1 score | 0.0 | f1 score | 0.0 | f1 score | 0.5794 |
| Recall | 0.0 | Recall | 0.0 | Recall | 0.6242 |
| Precision | 0.0 | Precision | 0.0 | Precision | 0.0 |

TABLE 3E

| Measured and computed features model results. Features: PSA, pathologic grade, percent positive cores, cores positive, Primary Score, miTNM, PSMA expression score, uptake SUV peak value, uptake prostate zone, uptake type (focal vs. diffuse), uptake extends outside prostate, aorta SUV mean, liver SUV mean | | | | | |
|---|---|---|---|---|---|
| SVM | | XGBoost | | Naïve Bayes | |
| Acc. | 0.6283 | Acc. | 0.6420 | Acc. | 0.7000 |
| AUC | 0.6230 | AUC | 0.6366 | AUC | 0.6679 |
| f1 score | 0.5757 | f1 score | 0.5892 | f1 score | 0.5747 |
| Recall | 0.5977 | Recall | 0.6282 | Recall | 0.5208 |
| Precision | 0.5724 | Precision | 0.5762 | Precision | 0.7022 |

TABLE 3F

Combined CNN prediction and measured and computed features model results.
Features: PSA, pathologic grade, percent positive cores, cores positive, Primary Score, PSMA expression score, uptake SUV peak value, uptake prostate zone + NN prediction

| SVM | | XGBoost | | Naïve Bayes | |
|---|---|---|---|---|---|
| Acc. | 0.6672 | Acc. | 0.6939 | Acc. | 0.7457 |
| AUC | 0.6600 | AUC | 0.6717 | AUC | 0.7083 |
| f1 score | 0.6054 | f1 score | 0.5681 | f1 score | 0.6306 |
| Recall | 0.6251 | Recall | 0.5383 | Recall | 0.5599 |
| Precision | 0.6146 | Precision | 0.6335 | Precision | 0.7673 |

I.ii Example 2: A Convolutional Neural Network Model Using Intraprostatic Patterns of [F18]DCFPyL Uptake in PSMA PET Images for Prediction of Synchronous Metastases This example provides additional results of and expands upon an imaging study that demonstrates use of a CNN model in conjunction with intraprostatic PSMA imaging, described in Example 1, above.

In particular, [F18]DCFPyL (PyL™) (also referred to as Piflufolast F-18 DCFPyL) is a PSMA targeted imaging agent that provides whole-body staging of prostate cancer. This example demonstrates how image analysis of a primary tumor using machine learning techniques (e.g., deep learning algorithms) can offer additional insight into disease biology, including the presence of co-existing metastatic disease. Approaches using convolutional neural network (CNN) models using inputs from whole prostate PyL™ PET/CT images along with automatically segmented hotspots within a prostate were used to predict presence or absence of synchronous metastases and were compared against established models built from clinicopathologic information.

As described in further detail, veterans with de novo prostate cancer that had been imaged with PyL PET/CT for initial staging were included in the retrospective analysis described in this example. PyL PET/CT images of the prostate were analyzed using aPROMISE, which automatically segments, localizes, and quantifies disease on PSMA PET/CT images. Automatically segmented prostate volumes (determined via automated segmentation of CT images) were used to map PyL™ uptake within the prostate, as reflected in the PET image channel. aPROMISE was also used to automatically detect and segment 3D hotspots representing potential cancerous lesions within a subject. Both the entire prostate, as well as aPROMISE defined hotspots were used as inputs for the CNN model. As described in further detail herein (e.g., below) an attention map analysis indicates that the hotspot information facilitates the neural network in determining locations and extents of tumors within the prostate. The CNN model architecture in this example was based on SqueezeNet v2. In order to train the CNN models and evaluate their performance, the image dataset was randomly split into training, validation, and test sets. Receiver operating characteristic (ROC) curves were generated and area under the curve (AUC) metrics were computed to assess model performance in predicting presence of metastases, and test predictions were compared with ground truth (M1). Model training was repeated 50 times (50 experiments) and the best performing experiment (e.g., trained model) was identified. For purposes of comparison with previous techniques based on evaluation of clinicopathological data, prediction scores determined using the UCSF-CAPRA scoring system and UCLA PSMA risk calculator were determined and compared with CNN model performance.

Of the 90 veterans evaluated in the analysis presented in this example, 47 presented localized disease and 43 had metastatic prostate cancer. The CNN model operating on image data alone achieved a median AUC of 0.72 for prediction of metastatic disease (ICR 0.64 and 0.8). Adding clinicopathologic information to imaging data via a fused model improved the AUC to a median of 0.82. For comparison, AUCs from the UCSF-CAPRA score and UCLA-PSMA risk calculator (any upstaging on PET), which rely on clinicopathologic information, were 0.729 and 0.754 for the dataset used in this example, respectively.

Accordingly, results of this example show the ability of a CNN based model to predict presence of synchronous metastases in patients intraprostatic PyL uptake patterns alone. Predictive accuracies of the CNN model for this dataset were comparable to published prediction models based on clinicopathologic features (namely, UCSF-CAPRA scoring and UCLA-PSMA risk calculator).

Predictions from CNN image analysis models were also combined with other measurable imaging parameters and clinicopathologic data to develop a fused model that discriminates between prostate cancers with or without co-existing metastases with high fidelity.

Materials and Methods

Figure 8C:
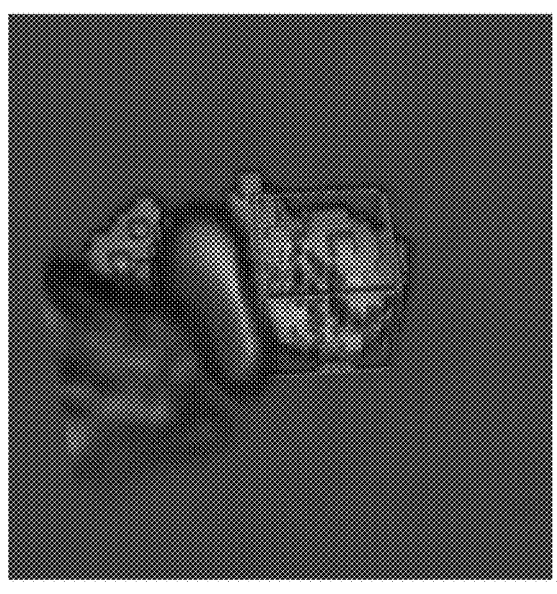
FIG. 8C is image showing the example PET image shown in FIG. 8A overlaid with the hotspot mask shown in FIG. 8B, according to an illustrative embodiment.
Figure 8B:
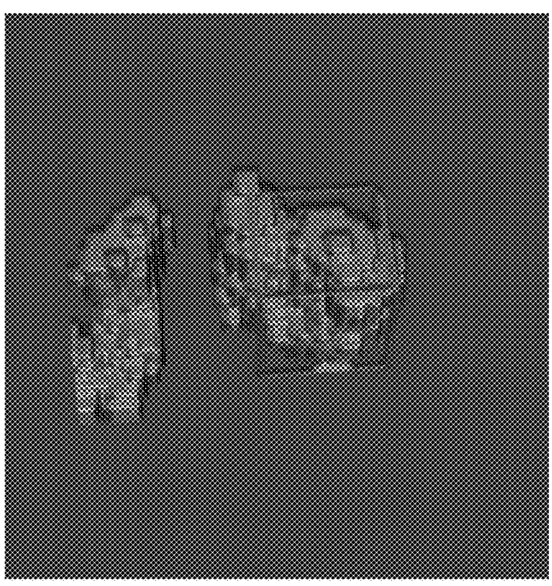
FIG. 8B is an example 3D hotspot mask, according to an illustrative embodiment.
Figure 8A:
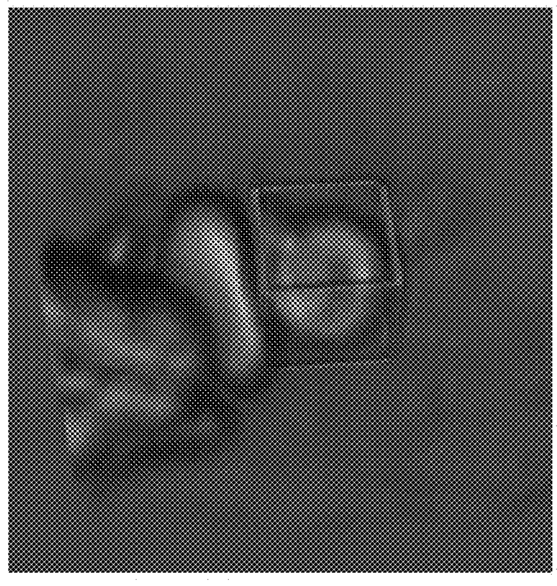
FIG. 8A is an example PET image of a prostate region, according to an illustrative embodiment.
Figure 9:
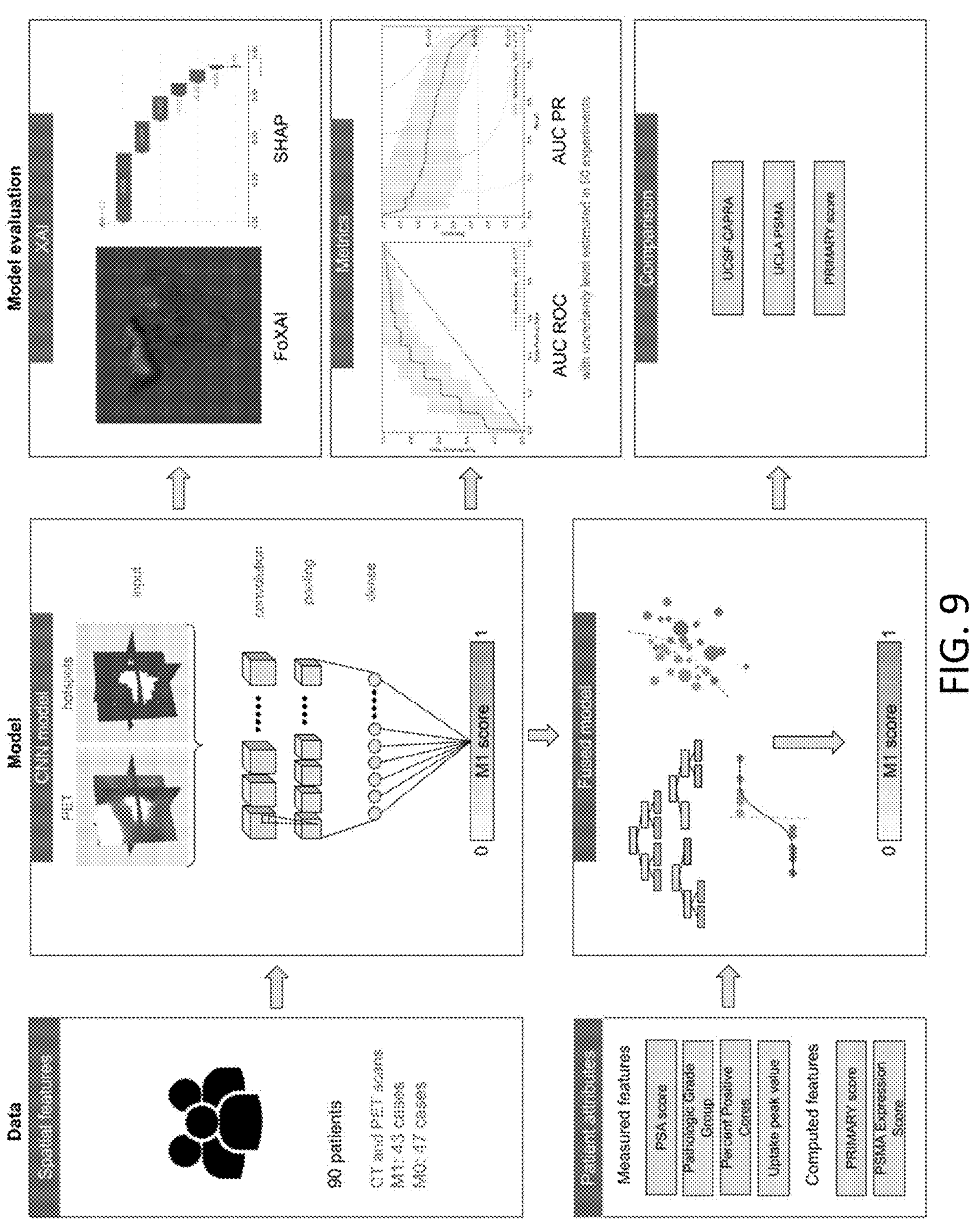
FIG. 9 is a schematic showing an example process for creation and evaluation of models for predicting metastases, according to an illustrative embodiment.

Dataset. Ninety (90) veterans with de novo prostate cancer were imaged with PyL PSMA PET/CT for initial staging (47 with localized disease and 43 with metastatic prostate cancer). Images of the prostate were analyzed using aPROMISE, which, among other things, segments the prostate gland and localizes and segments hotspots corresponding to regions of PET images determined to represent to potential intraprostatic lesions. The segmentation of the prostate was used to map PyL PET images of the prostate. Without wishing to be bound to any particular theory, neural networks are believed to exhibit performance improvements when provided with pragmatically extracted task-specific features, particularly when dealing with a limited number of cases. Accordingly, identifications of hotspots determined via aPROMISE were provided as input alongside PET prostate-region scans to CNN models to create a two-channel CNN model that leveraged information from prostate PET intensities and detected hotspots representing potential lesions. FIG. 9 shows an example system architecture, illustrating image-based inputs (PET image intensities and hotspots) to a CNN model, as well as a fused model that integrates the CNN-based image system with clinicopathologic data. FIGS. 8A-8C show example model inputs, with FIG. 8A showing a cuboid region surrounding a prostate in a PET image, FIG. 8B showing the same cuboid region overlaid on a 3D hotspot mask, and FIG. 8C showing an overlay of FIGS. 8A and 8B. Attention map analysis, described in further detail herein, indicates that the 3D hotspot mask, when used as input to a neural network, facilitated the network in identifying locations and extents of tumors.

CNN model architecture. Several different Convolutional Neural Network (CNN) architectures were evaluated. Since the limited number of training samples were believed to raise a high risk of model overfitting, only models with a relatively low number of parameters were considered in this example. In particular, modified version of the ResNet18, SqueezeNetv2, MobileNet, and ShuffleNet models were evaluated. These CNN architectures were originally designed for 2D image processing and, accordingly, were modified to make them suitable for 3D image analysis by substituting their original 2D convolutional and pooling layers with 3D convolution and pooling layers. Moreover, for the SqueezNetv2 architecture, the last network layers comprising dropout, convolution with kernel size 1, ReLU activation, and average 3D Pooling layers were substituted with adaptive max pooling 3D, dropout and fully connected layers. Models were trained using a weighted binary cross entropy loss function. The top-performing model (SqueezeNetv2) underwent further optimization through grid-search hyperparameter-tuning. Optimal values for group convolution, learning rate, regularization strength, and a set of augmentations (described in the paragraph below) were determined based on initial validation. The CNN model was trained for 300 epochs and the checkpoint for the best-performing epoch on the evaluation subset was retained and selected for testing.

Augmentations. To avoid overfitting, a randomly selected set of augmentations were applied to CNN inputs each epoch. In the present example, seven of the following fifteen augmentations were sampled and applied in random order: random rotation, random flip in left-right axes, random Gaussian noise, random standard deviation intensity shift, random contrast adjustment, random Gaussian smoothing, random Gaussian sharpening, random histogram shift, random Coarse shuffle, random 3D elastic distortion, random affine transformation, random Gibbs noise, random bias field, random K-space spike noise, and random Rician noise.

Multimodal model. To further improve metastases prediction performance, the top-performing CNN model (SqueezeNetv2), which utilized both the prostate intensities and hotspot identification input channels, was integrated into a fused model that also utilized various patient attributes, such as features derived from images and clinicopathologic data. These patient attributes included a measured PSA value, Pathologic Grade Group, Percent Positive Cores, a peak SUV prostate-located value, PRIMARY score, and PSMA Expression score (generated by PROMISEV2). A Naïve Bayes classifier was integrated to leverage the output from the CNN model in conjunction with other variable and categorical features to formulate the conclusive prediction of synchronous metastases. These categorical and variable features were integrated with the CNN model using fused model approaches, including a logistic regression, XGboost, and Naïve Bayes, resulting in a fused model.

Metrics. The dataset was split into training, validation, and test sets using stratified random sampling, in ratios of 0.5, 0.2, and 0.3 accordingly. Area under the receiver operating characteristic curve (AUC) was computed to evaluate performance of various models in predicting the presence of metastases and test predictions were compared with ground truth (M1). Training was repeated 50 times (50 experiments) and the best-performing experiment was identified. Prediction scores from UCSF-CAPRA and UCLA PSMA risk calculator were used as comparators.

Explainable artificial intelligence. This example also evaluates model performance using explainable artificial intelligence (AI). All deep learning models were explained using the FoXai library. Models on clinicopathologic data were explained using the SHAP library. In this manner, the set of input features could be selected based on their contribution to final model output, as measured using explainable AI techniques.

Results

Among the CNN model architectures tested, the SqueezeNetv2-based model provided the best performance, with an AUC of 0.7273. Results for all model architectures evaluated are shown in Table 4A, below. A fused model, which incorporated CNN model predictions along with patient attributes (e.g., clinicopathologic data), achieved state-of-the-art results in cancer metastasis diagnoses with a 0.82 AUC median, 0.75 and 0.87 AUCs in the $1^{st}$ and 3rd quartile, respectively.

TABLE 4A

Comparison of different CNN architecture performance. Metrics shown are a median of 50 experiments run with a stratified sampling of train, validation, and test set. Each neural network received two channels of input, a prostate volume and a hotspot mask.

| | SqueezeNet v2 | MobileNet | ResNet18 | ShuffleNet |
|---|---|---|---|---|
| AUC ROC | 0.7273 | 0.5818 | 0.6182 | 0.6727 |
| AUC PR | 0.6817 | 0.6131 | 0.6122 | 0.6561 |
| Accuracy | 0.6679 | 0.5389 | 0.5721 | 0.6216 |

Figure 10B:
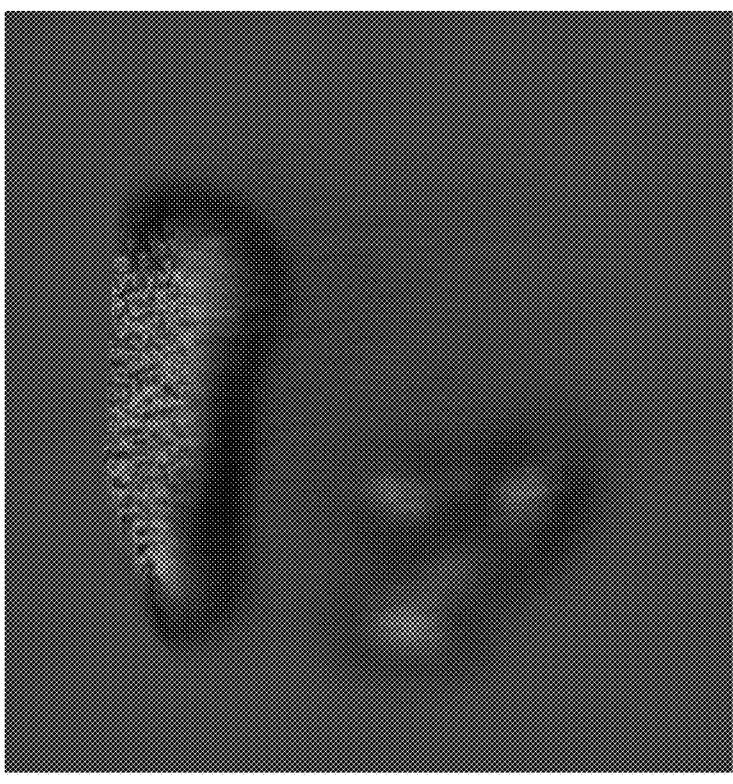
FIG. 10B is an image showing the attention map of FIG. 10A overlayed on an input PET image, according to an illustrative embodiment.
Figure 10A:
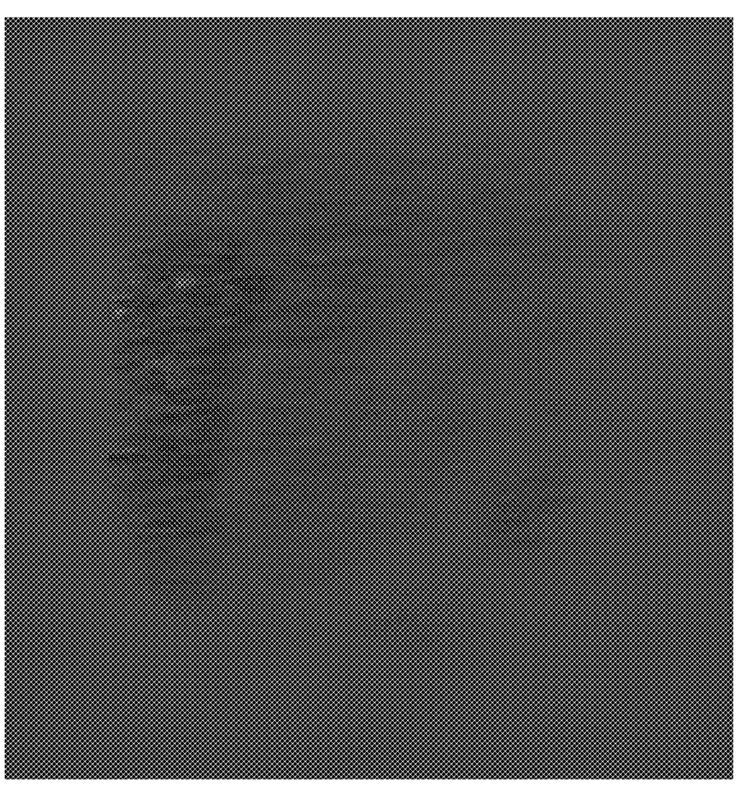
FIG. 10A is an image showing an attention map for an X gradient explainer computed for a CNN model that was trained on, and receives, as input, a single input channel comprising a prostate PET image, according to an illustrative embodiment.
Figure 11B:
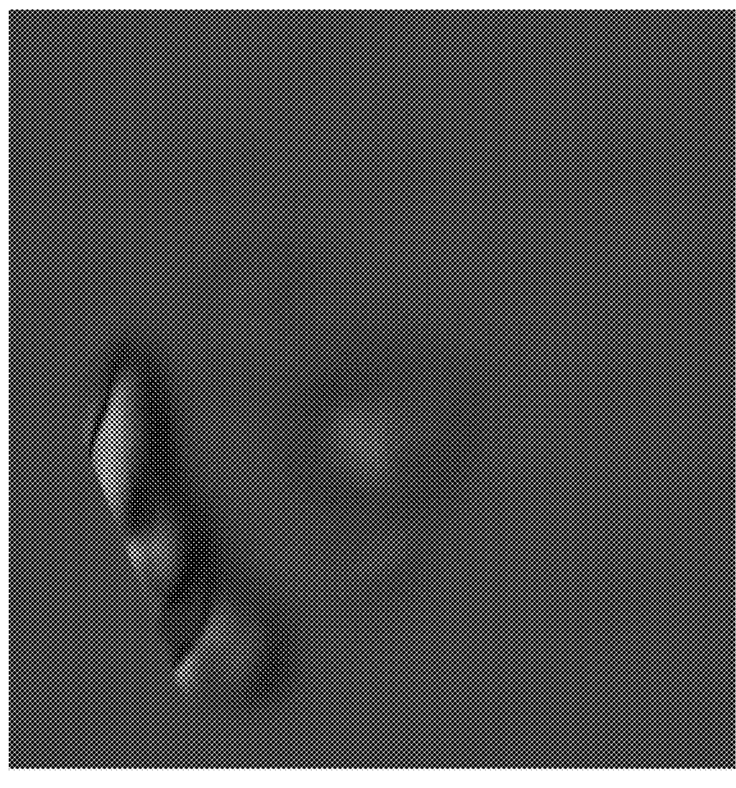
FIG. 11B is an image showing a prostate PET image portion used as input to a two-input-channel CNN model, according to an illustrative embodiment.
Figure 11A:
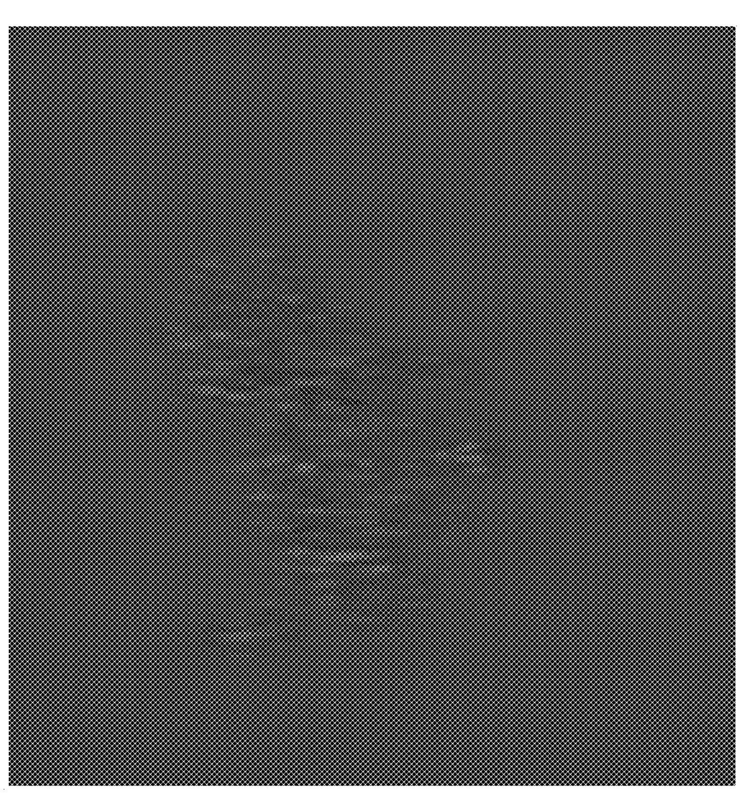
FIG. 11A is an image showing an attention map for an X gradient explainer computed for a CNN model that was trained on, and receives, as input, two input channels—one comprising a prostate PET image and a second comprising a hotspot mask, according to an illustrative embodiment.
Figure 11D:
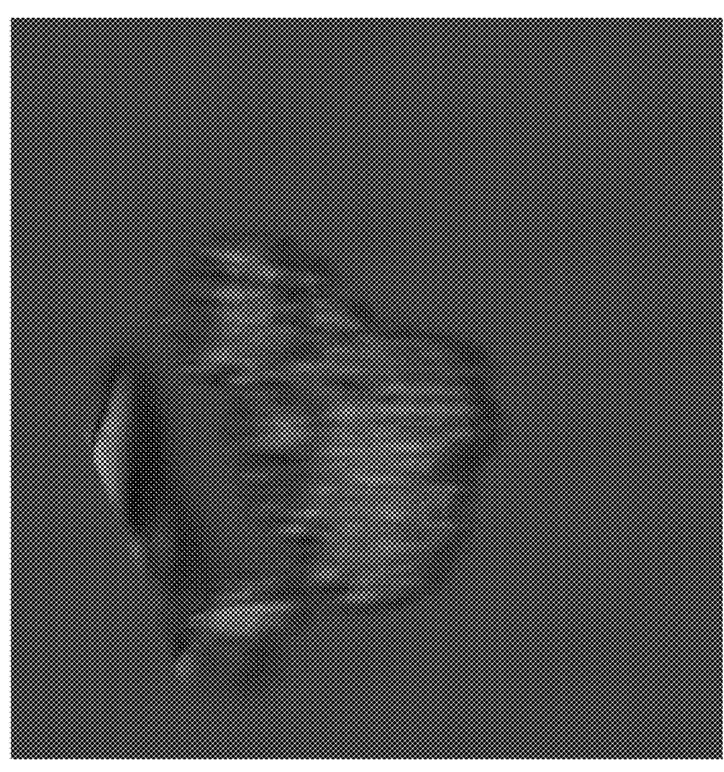
FIG. 11D is an image showing the attention map of FIG. 11A, the PET image of FIG. 11B, and the hotspot mask of FIG. 11C overlayed on each other, according to an illustrative embodiment.
Figure 11C:
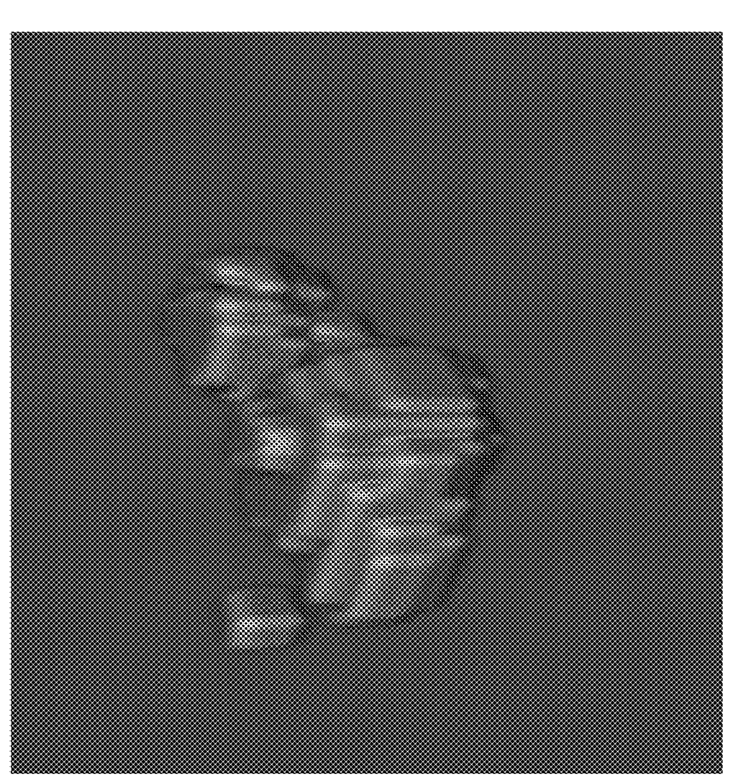
FIG. 11C is an image showing a hotspot mask used as input to a two-input-channel CNN model, according to an illustrative embodiment.

For the CNN models, incorporating hotspot identifications (e.g., a hotspot mask) as an input channel, in addition to the PyL PET prostate images, boosted model performance significantly. FIGS. 10A and 10B show attention maps for an X gradient explainer determined for a SqueezeNet v2-based CNN model trained on a single input channel comprising the PET image input alone (i.e., without a second, hotspot identification, channel), computed using the FoXai library (22). FIG. 10A shows attention map and FIG. 10B shows the attention map and PET image, overlaid. As shown, the attention maps indicate that the single input channel CNN model has difficulty focusing on hotspot areas. In particular, in comparison with a two-input channel CNN model, which incorporates both the PET image and hotspot identifications as input, the single channel model exhibits increased noise and reduced concentration of attention in the high intensity hotspot regions. FIG. 111A-D show attention map analysis for a two-input channel CNN model. As with the attention maps shown in FIGS. 10A and 10B, attention maps for an X gradient explainer were computed for a two input channel CNN model using the FoXai library (22). FIG. 11A shows the attention map for the CNN model alone. FIGS. 11B and 11C show the PET image and hotspot mask input channels, respectively. FIG. 11D shows an overlay of the two input channels and attention map (i.e., FIGS. 11A-C overlaid). As shown in FIGS. 11A-D, when provided with a hotspot mask, as a separate channel input to the CNN model, attention on the hotspot regions is increased. Transitioning from group convolution with a size of one to two further enhances the model's performance. Using a same kernel for the hotspot channel and PET channel again forces the model to focus more on the hotspot areas. Additionally, it was found that a group convolution of size 2 reduces a number of parameters in the model and therefore reduces model overfitting to the training data. This is demonstrated in Table 4B, below, which shows CNN model performance for different input channels and group convolution parameter values.

TABLE 4B

CNN model performance. Metrics shown are a median of 50 experiments, run with a stratified random sampling of train, validation, and test sets.

| | SqueezeNetv2 CT + PET group_conv = 1 | SqueezeNetv2 CT + PET group_conv = 2 | SqueezeNetv2 PET | SqueezeNetv2 PET + hotspots group_conv = 1 | SqueezeNetv2 PET + hotspots group_conv = 2 |
|---|---|---|---|---|---|
| AUC ROC | 0.5273 | 0.55 | 0.6333 | 0.6636 | 0.7273 |
| AUC PR | 0.5383 | 0.5579 | 0.6151 | 0.6468 | 0.6817 |
| Accuracy | 0.5238 | 0.5216 | 0.5909 | 0.6226 | 0.6679 |

Figure 12B:
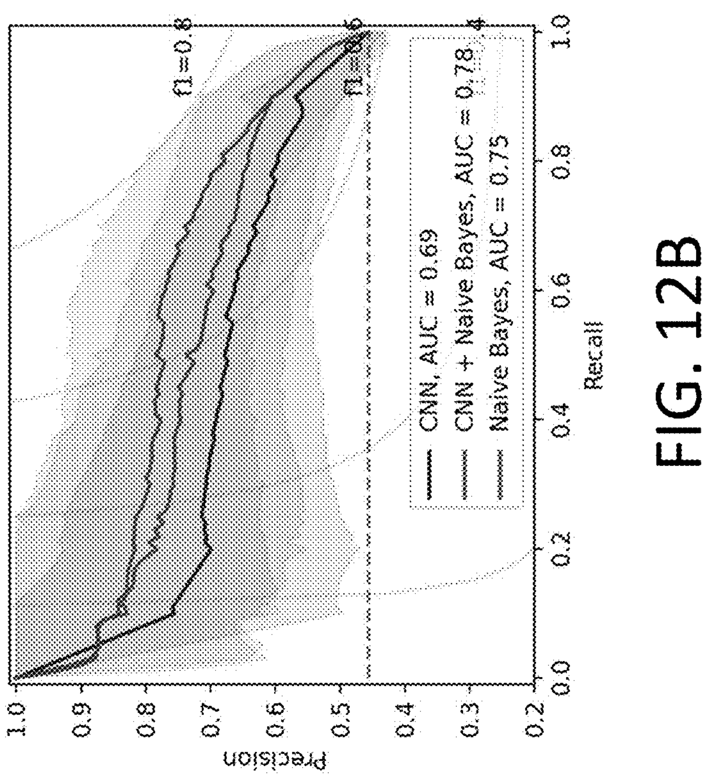
FIG. 12B is a plot showing precision-recall curves for three metastases prediction models, used in certain embodiments.
Figure 12A:
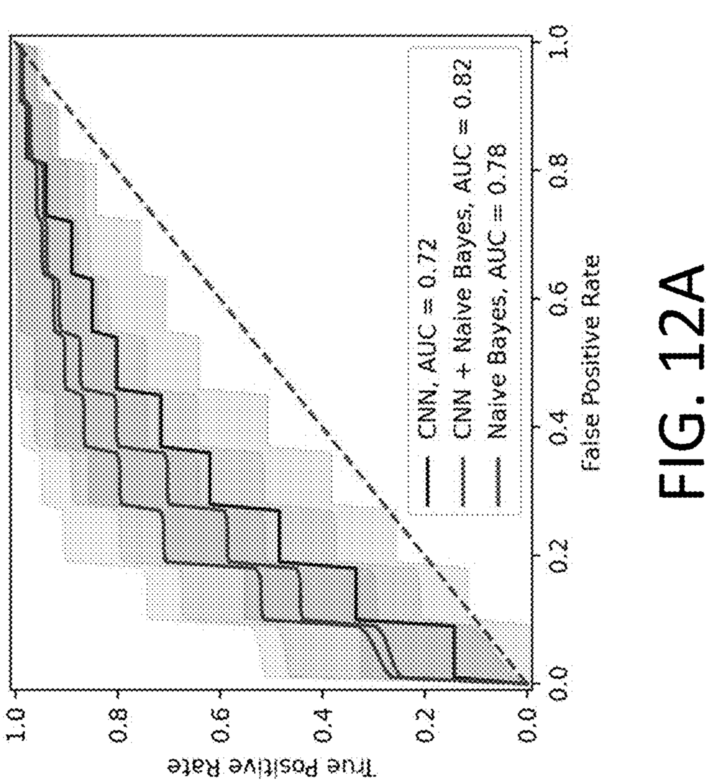
FIG. 12A is a plot showing receiver operating characteristic (ROC) curves for three metastases prediction models, used in certain embodiments.
Figure 12C:
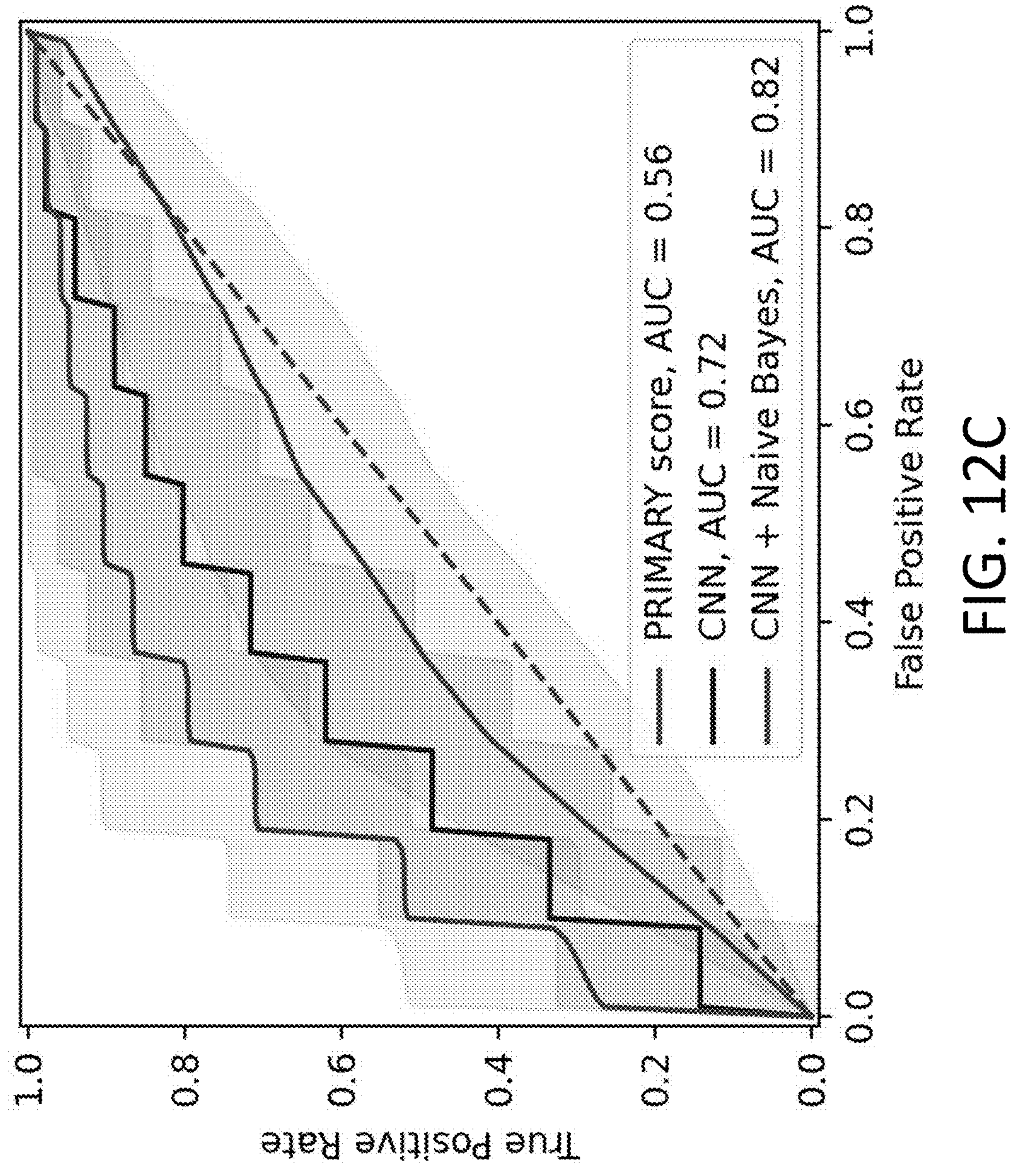
FIG. 12C is a plot showing receiver operating characteristic (ROC) curves for three metastases prediction models, used in certain embodiments.
Figure 13:
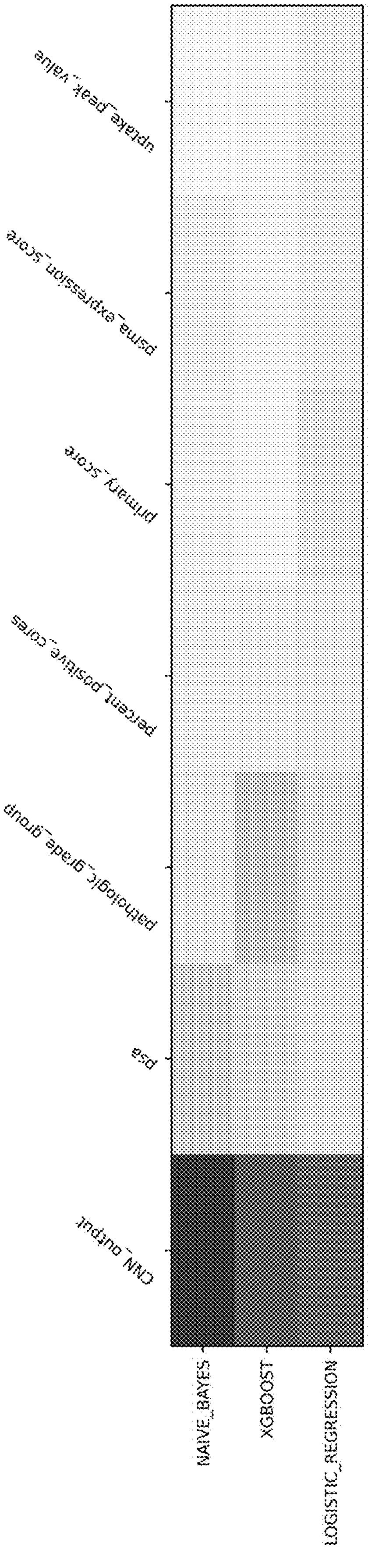
FIG. 13 is a matrix table showing predictive contributions of various input features, according to an illustrative embodiment.

FIGS. 12A and 12B show model performance metrics for (i) a CNN model alone, (ii) a Naïve Bayes classifier based on patient attributes (e.g., clinicopathologic data) alone, and (iii) a fused model, in which CNN model output was combined with clinicopathologic data via a Naïve Bayes classifier. FIG. 12C compares CNN model and fused model performance with PRIMARY score-based predictions. As shown in FIGS. 12A and 12B, the classifier model using only clinicopathologic data performed only slightly better than the CNN model alone, achieving a median AUC of 0.78 versus a median AUC of 0.72 for the CNN model alone. It appears that a combination of various patient attributes exhibits a slightly higher predictive power in comparison with the spatial, image-based input, features that are the sole input to the CNN model. To further elucidate the significance of individual input features, CNN model output and six patient attribute features (PSA value, Pathologic Grade, Percent Positive Cores, PRIMARY score, PSMA expression score, and uptake peak value) were analyzed individually to evaluate their individual contribution to model performance. FIG. 13 shows results of this analysis, performed via SHAP feature importance for Naïve Bayes, XGBoost, and logistic regression classifiers. In the figure, all features are sorted in descending order, from left to right, according to their contribution to model performance. As shown in FIG. 13, viewing each feature individually, the spatial feature analysis output from the CNN model are the most valuable. In particular, CNN model output provided the highest value, displaying a median AUC of 0.72, followed by the model based on PSA value alone at 0.71.

Performance of a Naïve Bayes patient attribute model (without CNN model input) and three fused models are shown in Table 4C, below.

TABLE 4C

Fused model performance. Presented metrics are the median of 50 experiments run with a stratified sampling of train, validation, and test set. CNN input to the fused mode is a 0-1 continuous output of SquezeNetv2, with PET + hotspots model input and group convolution of 2.

| | Naive Bayes PSA, Pathologic Grade, Percent Positive Cores, Primary Score, PSMA Expression Score, Uptake peak value | Naive Bayes CNN + PSA, Pathologic Grade, Percent Positive Cores, Primary Score, PSMA Expression Score, Uptake peak value | XGBoost CNN + PSA, Pathologic Grade, Percent Positive Cores, Primary Score, PSMA Expression Score, Uptake peak value | Logistic Regression CNN + PSA, Pathologic Grade, Percent Positive Cores, Primary Score, PSMA Expression Score, Uptake peak value |
|---|---|---|---|---|
| AUC ROC | 0.7773 | 0.821 | 0.7159 | 0.7369 |
| AUC PR | 0.7468 | 0.7814 | 0.6564 | 0.6942 |
| Accuracy | 0.6827 | 0.7411 | 0.6615 | 0.6786 |

Figure 14:
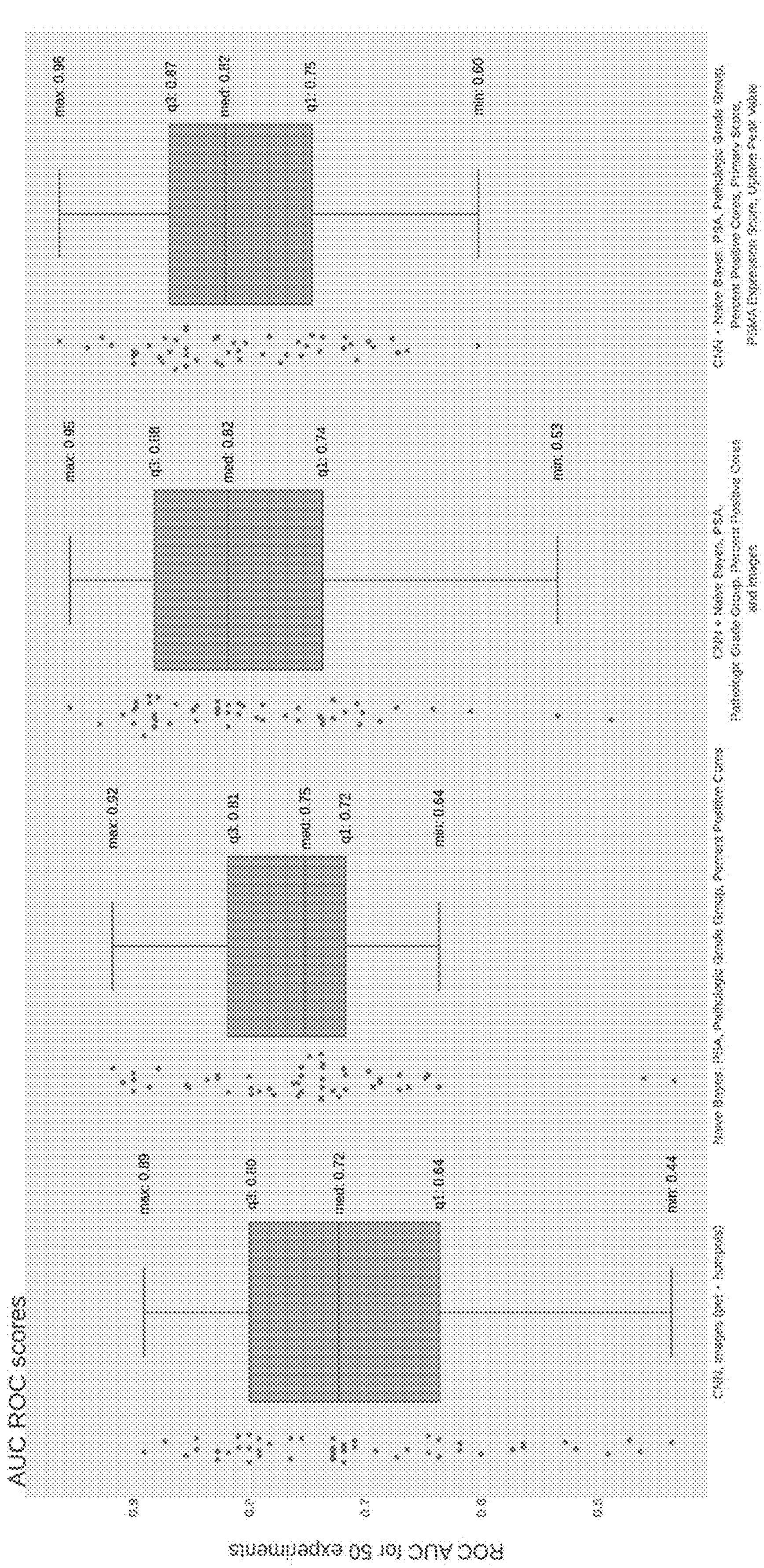
FIG. 14 is a box plot showing four box and whisker plots for certain metastases prediction models, according to certain embodiments.

FIG. 14 presents box and whisker plots for 50 experiments run for several predictive model setups, in particular, from left to right (i) CNN model (i.e., analysis of spatial image data) output alone, (ii) Naïve Bayes classifier based on patient attributes (e.g., clinicopathological data) alone (in particular, PSA score, Pathologic Grade, and Percent Positive Cores), and (iii) and (iv), two fused models, with CNN model output combined with different sets of patient attributes as shown in the figure [in particular, in (iii) CNN model output (based on prostate PET images and hotspot mask inputs) was combined with PSA score, Pathologic Grade, and Percent Positive Cores and in (iv) CNN model output (based on prostate PET images and hotspot mask inputs) was combined with PSA score. Pathologic Grade, and Percent Positive Cores, PSMA Expression score, uptake peak value and PRIMARY score]. P values for the four models shown in FIG. 14 are shown in Table 4D, below.

TABLE 4D p-values for various models.

| | 0 | 1 | 2 | 3 |
|---|---|---|---|---|
| 0 | 1 | 0.022019 | 0.000037 | 0.000001 |
| 1 | 0.022019 | 1 | 0.029922 | 0.003686 |
| 2 | 0.000037 | 0.029922 | 1 | 0.574106 |
| 3 | 0.000001 | 0.003686 | 0.574106 | 1 |

0: spatial data-only model,
1: clinico-pathologic data-only model,
2: fused spatial and clinico-pathologic models,
3: fused model along with more patient attributes (PSMA Expression score, PRIMARY score, and peak uptake SUV value). P-values are computed using a t-test.

I.iii Example 3: AI Models Analyze PSMA PET/CT Images of Primary Tumor to Prognosticate Metastatic Progression A subset of localized prostate cancers pose a high risk of metastatic progression to lethal disease requiring a more robust initial treatment approach, while others may follow a more indolent course where less aggressive treatment is desirable. Accurate prognostic information at the time of diagnosis, accordingly, allows patients and physicians to select a best treatment approach. In certain cases, clinicopathologic data may be used to assess the risk of metastatic progression. More recently, transcriptomic data and machine learning models that include data from digital histopathology (e.g., artera.ia) have been used to add further prognostic power. Previously, imaging scans have been used only to determine a clinical stage and assess the presence and localization of metastatic disease, but not for prognostic predictions—e.g., forecasting a likely course of disease, such as risk that disease currently presenting as localized cancer will, in the future, be found to have metastasized.

This example is based on and evaluates the insight that a machine learning approach may be used to extract otherwise inaccessible prognostic information from PyL™ PET images of primary prostate tumors. In particular, the present example demonstrates development and use of a model to prognosticate risk of metastatic progression after curative intent therapy for localized prostate cancer.

Limited availability of data at multiple time points—namely, images of patients at initial visits, where no metastases were apparent followed by diagnosis of metastatic progression at subsequent time points, after curative intent therapy—however, presented an obstacle to directly training a model on this particular outcome (PSMA PET/CT imaging had been initiated in late 2018). Accordingly, instead of relying on data representing disease progression over time for training, imaging data obtained at a single time point for patients having localized and/or metastatic disease was used to train a machine learning model to predict, based on image intensities and detected hotspots within a prostate volume, whether a patient had co-existing (i.e., synchronous) metastases. Once trained, this model was then used to analyze images of patients initially presenting with localized disease and predict whether they would or would not develop metastatic progression (radiographic progression) after curative intent therapy. Without wishing to be bound to any particular theory this approach—whereby models trained to predict co-existing, synchronous metastases that were observable in PyL PET/CT images could (also) be used to predict whether metastases would develop later, following therapy—leverages the insight that most early metastatic progression events occur consequent to growth of co-existing occult metastases at the time of curative intent therapy.

CNN and fused (multi-modal) models were developed and trained as described in Example 2, above, leveraging the above-described dataset of 90 veterans, who were imaged at initial staging, with imaging showing either unequivocal evidence for metastatic disease or no metastatic disease (non-metastatic N=47; metastatic N=43). As described herein (in Example 2, above), a CNN model was trained to predict presence of synchronous metastases using input channels of (i) prostate volume PET intensities and (ii) detected hotspots. A fused (also referred to as multimodal) model was developed by integrating clinicopathologic data with the CNN predictions via a Naïve Bayes approach, as described in Example 2 and illustrated in FIG. 9.

While the CNN and fused models were trained to use images of the primary tumor (i.e., within the prostate) and, in the case of the fused model, additionally clinicopathologic data, to determine whether a particular patient had (e.g., currently) synchronous metastases, the ability to predict whether a patient would have early metastatic progression after curative intent therapy is a particularly relevant and valuable clinical objective. Obtaining a sufficient amount of examples tracking metastatic progression events to train such a model directly was not possible in this case (and may be challenging in other prognostic applications), as described herein. Accordingly, the CNN and fused modes that were trained to predict for synchronous metastatic disease by evaluating the PSMA PET/CT data in the primary tumor region were evaluated for their ability to evaluate images of patients initially presenting with localized disease and discriminate between those that would and would not develop metastases following curative intent therapy. In training the model, the non-metastatic cases were purposefully selected to minimize contamination from scans of patients who had early metastatic progression events and the metastatic cases were purposefully selected to minimize the risk of false positives.

In particular, the CNN and fused models was applied to a cohort of veterans (N=23) who had no evidence of metastases at initial staging, underwent curative intent therapy (either radical prostatectomy or radiotherapy with androgen deprivation therapy), had at least four years of follow-up, and had either (1) no evidence of any progression up to four years (N=13), or (2) unequivocal metastatic progression identified on PSMA PET/CT within four years (N=10). The CNN model alone (with no contribution from clinicopathologic data and measurable imaging parameters) was able to discriminate between those who had a metastatic progression within 4 years versus those that did not with an AUC of 0.727, while the fused (multimodal) model was able to do so with an AUC of 0.855. Prediction scores from UCSF-CAPRA and UCLA PSMA risk calculators were also computed, for comparison purposes, with CAPRA and the UCLA PSMA risk calculator had AUCs of 0.768 and 0.702, respectively.

Accordingly, this example demonstrates that machine learning models may be trained to predict presence of co-existing (e.g., synchronous) metastases, and then used, at an inference stage, to predict whether patients initially presenting with localized disease will or will not develop metastases, for example following therapy.

EQUIVALENTS

It is to be understood that while the disclosure has been described in conjunction with the detailed description thereof, the foregoing description is intended to illustrate and not limit the scope of the claims. Other aspects, advantages, and modifications are within the scope of the claims.

This written description uses examples to disclose the invention, including the best mode, and also to enable any person skilled in the art to practice the present embodiments, including making and using any devices or systems and performing any incorporated methods. The patentable scope of the present embodiments is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for automatically processing one or more medical images of a subject and using the processed image(s) to automatically predict a presence and/or a risk of metastases, the method comprising:

(a) receiving, by a processor of a computing device, one or more medical images of a prostate of the subject, wherein the one or more medical image(s) comprise a 3D functional image acquired following administration to the subject of an imaging agent;

(b) automatically identifying, by the processor, within the 3D functional image, a prostate volume corresponding to the prostate of the subject;

(c) automatically identifying, by the processor, one or more hotspots within the prostate volume, said one or more hotspots corresponding to localized regions of high intensity relative to their surroundings and representing lesions or potential lesions within the subject; and (d) predicting, by the processor, using a neural network, (i) a presence of metastases in the subject, and/or (ii) a risk of metastases in the subject, said predicting based at least in part on the automatically identified prostate volume and the automatically identified one or more hotspot(s) within the prostate volume, wherein the neural network receives at least two channels of input, the at least two channels of input comprising:

(A) a prostate intensity channel comprising intensities of voxels located within the prostate volume; and (B) a hotspot mask channel comprising a mask identifying the one or more hotspots.

2. The method of claim 1, wherein the one or more medical images further comprise a 3D anatomical image.

3. The method of claim 1, wherein the one or more medical images comprise a PET image and/or a PET/CT image.

4. The method of claim 1, wherein the one or more medical images are obtained prior to treatment.

5. The method of claim 2, wherein the one or more medical images comprise a 3D anatomical image co-aligned with the 3D functional image, and wherein step (b) comprises identifying an anatomical volume of interest (VOI) representing a prostate within the 3D anatomical image and using the anatomical VOI to identify the prostate volume within the 3D functional image.

6. The method of claim 5, comprising using a first machine learning model to (i) identify the prostate volume within the 3D functional image and/or (ii) identify the anatomical VOI within the 3D anatomical image.

7. The method of claim 1, wherein step (c) comprises using a second machine learning model to automatically identify the one or more hotspots.

8. The method of claim 1, wherein the neural network does not receive, as input, intensities of voxels located outside the prostate volume of the image(s).

9. The method of claim 1, wherein the neural network generates, as output, a likelihood value representing a likelihood that the subject has or will develop metastases.

10. The method of claim 1, wherein step (d) comprises using one or more measured features to predict presence and/or risk of metastases in the subject.

11. The method of claim 1, wherein step (d) comprises using one or more computed features to predict presence and/or risk of metastases in the subject.

12. The method of claim 1, wherein the imaging agent is or comprises a PSMA binding agent.

13. The method of claim 1, wherein the one or more medical images do not include any graphical representation(s) of metastases outside the prostate volume.

14. The method of claim 1, comprising, at step (d), predicting the risk of metastases.

15. The method of claim 1, comprising, at step (d), predicting the presence of metastases.

16. The method of claim 1, wherein the neural network is a trained neural network, having been trained using a plurality of example images each obtained from a particular subject and comprising a graphical representation of suspect regions within a prostate region of the particular subject, said plurality of example images comprising:

(A) a plurality of positive example images obtained for subjects known to have metastases; and (B) a plurality of negative example images obtained for subjects having localized disease.

17. The method of claim 16, wherein the plurality of positive example images are images obtained for subjects having synchronous metastases and wherein step (d) comprises using the neural network to predict the risk of metastases for the subject.

18. The method of claim 1, wherein the subject is or has been determined to have localized prostate cancer, with observable lesions confined to a primary tumor volume comprising the prostate of the subject and wherein step (d) comprises predicting, as the risk of metastases, a likelihood that the subject will develop one or more observable lesions outside the primary tumor volume.

19. The method of claim 18, wherein step (c) comprises automatically identifying the one or more hotspot(s) within the prostate volume, but not identifying any hotspot(s) outside of the prostate volume and/or a surrounding buffer/margin.

20. The method of claim 18, wherein no hotspot(s) are identified outside of the prostate volume.

21. The method of claim 18, wherein step (d) comprises generating, by the neural network, a likelihood value representing a risk that lesions will spread outside the primary tumor region within a particular period of time.

22. The method of claim 1, wherein step (d) comprises predicting a risk that the subject will develop metachronous metastases.

23. A system for automatically processing one or more medical images of a subject and using the processed image(s) to automatically predict a presence and/or a risk of metastases, the system comprising:

a processor of a computing device; and memory having instructions stored thereon, wherein the instructions, when executed by the processor, cause the processor to:

(a) automatically identify, within a 3D functional image acquired following administration to the subject or an imaging agent, a prostate volume corresponding to a prostate of the subject;

(b) automatically identify one or more hotspots within the prostate volume, said one or more hotspots corresponding to localized regions of high intensity relative to their surroundings and representing lesions or potential lesions within the subject; and (c) predict, using a neural network, (i) a presence of metastases in the subject, and/or (ii) a risk of metastases in the subject, said predicting based at least in part on the automatically identified prostate volume and the automatically identified one or more hotspots within the prostate volume, wherein the neural network receives at least two channels of input, the at least two channels of input comprising:

(A) a prostate intensity channel comprising intensities of voxels located within the prostate volume; and (B) a hotspot mask channel comprising a mask identifying the one or more hotspots.

24. A method for automatically processing medical images of a subject presenting with localized prostate cancer and using the processed image(s) to automatically predict a risk that the subject will develop metastases, the method comprising:

(a) receiving, by a processor of a computing device, a medical image of the subject, comprising a graphical representation of a prostate of the subject;

(b) automatically identifying, by the processor, within the medical image, a prostate volume corresponding to a prostate of the subject;

(c) automatically identifying, by the processor, one or more hotspots within the prostate volume, said one or more hotspots corresponding to localized regions of high intensity relative to their surroundings and representing lesions or potential lesions within the subject; and (d) predicting, by the processor, using a neural network, a risk of metastases in the subject based at least in part on the prostate volume and the automatically identified one or more hotspots within the prostate volume, wherein the neural network is a trained neural network, having been trained using a plurality of example images each obtained from a particular individual and comprising a graphical representation of hotspots within a prostate region of the particular subject, said plurality of example images comprising:

(A) a plurality of positive example images obtained for individuals having synchronous metastases; and (B) a plurality of negative example images obtained for individuals having localized disease.

25. The method of claim 24, wherein the subject is or has been determined to have localized prostate cancer, with observable lesions confined to a primary tumor volume comprising and/or about the prostate of the subject and wherein step (d) comprises predicting, as the risk of metastases, a likelihood that the subject will develop one or more observable lesions outside the primary tumor volume.

26. The method of claim 24, wherein step (c) comprises automatically identifying the one or more hotspot(s) within the prostate volume, but not identifying any hotspot(s) outside of the prostate volume and/or a surrounding buffer/margin.

27. The method of claim 24, wherein no hotspot(s) are identified outside of the prostate volume.

28. The method of claim 24, wherein step (d) comprises generating, by the neural network, a likelihood value representing a risk that lesions will spread outside the prostate region within a particular period of time.

29. The method of claim 24, wherein the neural network receives at least two channels of input, the at least two channels of input comprising:

(A) a prostate intensity channel comprising intensities of voxels located within the prostate volume of the image (s) corresponding to the prostate; and (B) a hotspot mask channel comprising a mask identifying the one or more hotspot(s).

* * * * *